United States Patent

Morita et al.

[11] Patent Number: 6,077,814
[45] Date of Patent: Jun. 20, 2000

[54] 1-SUBSTITUTED 4-CARBAMOYL-1,2,4-TRIAZOL-5-ONE DERIVATIVES AND HERBICIDE

[75] Inventors: Ken Morita, Hiratsuka; Tsunehiro Kido, Hadano; Kazuo Hirayama, Isehara; Hiroyuki Okita, Atsugi; Toshiharu Ohno, Atsugi; Yoshihisa Watanabe, Atsugi; Masahide Onoe, Atsugi, all of Japan

[73] Assignee: Hokko Chemical Industry Co., Ltd., Tokyo, Japan

[21] Appl. No.: 09/367,822

[22] PCT Filed: Feb. 26, 1998

[86] PCT No.: PCT/JP98/00803

§ 371 Date: Aug. 23, 1999

§ 102(e) Date: Aug. 23, 1999

[87] PCT Pub. No.: WO98/38176

PCT Pub. Date: Sep. 3, 1998

[30] Foreign Application Priority Data

Feb. 26, 1997 [JP] Japan ..................................... 9-042743

[51] Int. Cl.[7] ........................ A01N 35/04; A01N 43/653; C07D 249/12
[52] U.S. Cl. .......................... 504/273; 504/274; 504/253; 546/272.4; 548/263.2
[58] Field of Search ..................... 504/273, 274, 504/253; 546/272.4; 548/263.2

[56] References Cited

FOREIGN PATENT DOCUMENTS

| 202929 | 11/1986 | European Pat. Off. . |
|---|---|---|
| 617026 | 9/1994 | European Pat. Off. . |
| 03106865 | 5/1991 | Japan . |
| 08311048 | 11/1996 | Japan . |

OTHER PUBLICATIONS

Chem. Abstracts, vol. 118, No. 118:54226b, pp. 286–287, 1993.

*Primary Examiner*—Joseph McKane
*Assistant Examiner*—Jane C. Osweecki
*Attorney, Agent, or Firm*—Larson & Taylor PLC

[57] ABSTRACT

A 1-phenyl, naphthyl or aralkyl-4-(N,N-di-substituted carbamoyl)-1,2,4-triazol-5-one derivative represented by the general formula (I)

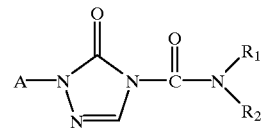

wherein A is an unsubstituted or substituted phenyl group, 1-naphthyl group, 5,6,7,8-tetrahydro-1-naphthyl group or an aralkyl group such as an unsubstituted or substituted benzyl group and so on, $R_1$ is a lower alkyl group and so on, and $R_2$ is an unsubstituted or substituted phenyl group and so on, was prepared as novel compounds. This 1-substituted-4-carbamoyl-1,2,4-triazol-5-one derivative does not substantially exhibit phytotoxicity to various agricultural crop plants and therefore is useful as a selective herbicide.

17 Claims, No Drawings

1-SUBSTITUTED 4-CARBAMOYL-1,2,4-TRIAZOL-5-ONE DERIVATIVES AND HERBICIDE

This application is a 371 of PCT/JP98/00803 filed Feb. 26, 1998.

TECHNICAL FIELD

This invention relates to a new 1-substituted-4-carbamoyl-1,2,4-triazol-5-one derivative useful as a herbicide, and also this invention relates to a herbicidal composition comprising said derivative as an active ingredient. This invention is therefore useful in the fields of chemical industry and agriculture, especially in the field of the art for the manufacture of agricultural chemicals.

BACKGROUND ART

Hitherto, it has already been known that certain 1,2,4-triazol-5-one derivatives and tetrazolinone derivatives have herbicidal and fungicidal activities, as described below.

For example, the known 1,2,4-triazol-5-one derivatives include such compounds as described in literatures (1) to (4) below.

(1) Japanese patent application first publication (Kokai) No. Hei-7-76578 describes a compound represented by the general formula (A)

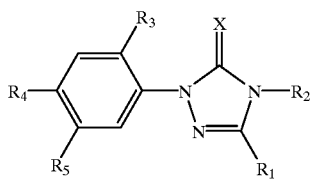

(A)

wherein X denotes oxygen atom or sulfur atom, $R_1$ denotes a haloalkyl group, $R_2$ denotes a cycloalkyl group, a cycloalkylalkyl group and so on, $R_3$ denotes hydrogen atom or a halogen atom, $R_4$ denotes nitrile group or nitro group and $R_5$ denotes a halogen atom or a heterocyclic alkoxy group and so on.

(2) Japanese patent application first publication (Kokai) No. Hei-3-106865 describes a compound represented by the general formula (B)

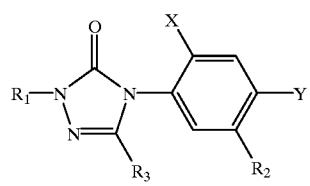

(B)

wherein $R_1$ denotes a cycloalkyl group, a phenylalkyl group, a halogen atom, an aminocarbonyl group substituted with a substituted phenyl group, and so on; $R_2$ denotes hydrogen atom or a lower alkyl group; and $R_3$ denotes a halogen atom, an alkyl group and so on.

(3) Japanese patent application first publication (Kokai) No. Sho-64-29368 describes a compound represented by the general formula (C)

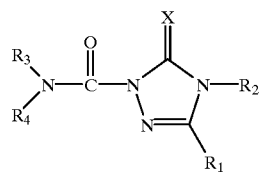

(C)

wherein X and Y denote oxygen atom or sulfur atom, $R_1$ denotes hydrogen atom and so on, $R_2$ denotes an unsubstituted or substituted phenyl group, an aralkyl group and so on, and $R_3$ and $R_4$ denote hydrogen atom, an alkyl group or an unsubstituted or substituted aryl group and so on.

(4) Japanese patent application first publication (Kokai) No. Hei-6-293744 describes a compound represented by the general formula (D)

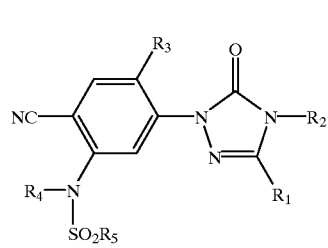

(D)

wherein $R_1$ denotes hydrogen atom and so on; $R_2$ denotes

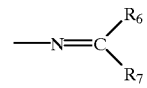

in which $R_6$ and $R_7$ denote an alkyl group, an alkenyl group, an alkynyl group, a cycloalkyl group, an aryl group and so on; $R_3$ denotes hydrogen atom, an alkyl group, a haloalkyl group and so on; $R_4$ denotes hydrogen atom and so on; and $R_5$ denotes amino group or hydroxy group and so on.

Furthermore, various 1,2,4-triazol-5-one derivatives have been described in the following literatures (5) to (24), namely (5) Japanese patent application first publication (Kokai) No. Sho-56-32403; (6) Japanese patent application first publication (Kokai) No. Sho-56-53663; (7) Japanese patent application first publication (Kokai) No. Sho-56-53662; (8) Japanese patent application first publication (Kokai) No. Sho-58-23680; (9) U.S. Pat. No. 4,705,557; (10) PCT international publication No. WO85/01637; (11) PCT international publication No. WO86/02642; (12) U.K. patent No. 2230261 specification; (13) Japanese patent application first publication (Kokai) No. Hei-3-106865; (14) German patent No. 4437049; (15) German patent No.4435476; (16) German patent No. 4431219; (17) U.S. Pat. No. 5,035,740 specification ; (18) Japanese patent application first publication (Kokai) No. Hei-3-181472; (19) German patent No. 3920414; (20) Japanese patent application first publication (Kokai) No. Hei-3-17070; (21) South African patent No. 8805308; (22) Japanese patent application first publication (Kokai) No. Sho-64-29368; (23) Japanese patent application first publication (Kokai) No. Sho-63-255271; and (24) Japanese patent application first publication (Kokai) No. Sho-52-118471.

However, the above-mentioned literatures (1) to (24) do not describe any 1,2,4-triazol-5-one derivatives having carbamoyl group at the 4-position thereof.

Furthermore, for the tetrazolinone derivatives there have been known such compounds as described in literatures (25) to (50) below.

(25) Japanese patent application first publication (Kokai) No. Sho-62-12767 describes a compound represented by the general formula (E)

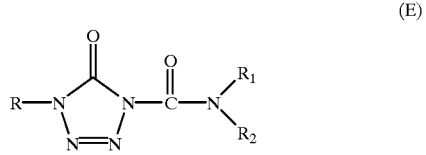

wherein R denotes a cycloalkyl group, phenyl group, naphthyl group and so on, $R_1$ and $R_2$ may be the same or different and each denote a $C_1$–$C_6$ alkyl group, a $C_5$–$C_6$ alkenyl group, a $C_5$–$C_6$ cycloalkyl group, a $C_7$–$C_9$ aralkyl group, or phenyl group which may be substituted with a $C_1$–$C_6$ alkyl group, a $C_1$–$C_6$ haloalkyl group or a $C_1$–$C_6$ alkoxy group and so on.

In addition, the known tetrazolinone derivatives include such compounds as described in (26) Japanese patent application first publication (Kokai) No. Sho-60-146879; (27) Japanese patent application first publication (Kokai) No. Hei-5-331154; (28) Japanese patent application first publication (Kokai) No. Hei-5-339249; (29) Japanese patent application first publication (Kokai) No. Hei-5-331153; (30) Japanese patent application first publication (Kokai) No. Hei-6-306061; (31) Japanese patent application first publication (Kokai) No. Hei-6-199818; (32) Japanese patent application first publication (Kokai) No. Hei-7-258230; (33) Japanese patent application first publication (Kokai) No. Hei-8-81459; (34) Japanese patent application first publication (Kokai) No. Hei-8-99975; (35) Japanese patent application first publication (Kokai) No. Hei-8-119947; (36) Japanese patent application first publication (Kokai) No. Hei-8-119948; (37) Japanese patent application first publication (Kokai) No. Hei-8-119950; (38) Japanese patent application first publication (Kokai) No. Hei-8-119951; (39) Japanese patent application first publication (Kokai) No. Hei-8-225547; (40) Japanese patent application first publication (Kokai) No. Hei-8-311048; (41) Japanese patent application first publication (Kokai) No. Hei-8-259549;

(42) U.S. Pat. No. 4,830,661 specification; (43) U.S. Pat. No. 4,956,469 specification; (44) U.S. Pat. No. 5,003,075 specification; (45) U.S. Pat. No. 5,019,152 specification; (46) Portuguese patent No. 101563 specification; (47) Japanese patent application first publication (Kokai) No. Hei-8-119949; (48) Japanese patent application first publication (Kokai) No. Hei-8-259548; (49) U.S. Pat. No. 5,136,868 specification; and (50) PCT international publication No. WO85/01939.

In the development of the herbicide, it is an important subject to create such new herbicidal compounds which exhibit a selective herbicidal activity owing to that some differences occur between the sensitivity of crop plants, namely useful cultivated plants and the sensitivity of weeds against a herbicide, and so on. However, when certain herbicidal compounds exhibit a phytotoxicity to the crop plants even if they have a high herbicidal activity, it is hard to say that such herbicidal compounds can be used satisfactorily as the herbicide in practice. Thus, it is now demanded to develop such new herbicidal compounds which is free from the drawbacks mentioned above. In this view, the above-mentioned 1,2,4-triazol-5-one and tetrazolinone derivatives which are known compounds are not necessarily a satisfactory herbicide. Accordingly, it is an object of this invention to provide, in place of the above-mentioned known herbicidal compounds, such new 1-substituted-4-carbamoyl-1,2,4-triazol-5-one derivatives which have an excellent herbicidal activity and show very low phytotoxicity to the crop plants and hence have a safety to the crop plants when used as the herbicide. It is another object of this invention to provide a herbicide comprising such new 1-substituted-4-carbamoyl-1,2,4-triazol-5-one derivatives as an active ingredient.

DISCLOSURE OF INVENTION

In order to achieve the above-mentioned objects of this invention, we, the present inventors, have eagerly studied on 1,2,4-triazol-5-one derivatives. As a result, the present inventors have now succeeded in synthesizing a number of new 1-substituted-4-carbamoyl-1,2,4-triazol-5-one derivatives which have hitherto been unknown. Furthermore, the present inventors have eagerly researched herbicidal activity and utilities of said new 1-substituted-4-carbamoyl-1,2,4-triazol-5-one derivatives so synthesized. As a result, the present inventors have surprisingly found that a new 1-substituted-4-carbamoyl-1,2,4-triazol-5-one derivative represented by the general formula (I) given below does not show any phytotoxicity to the useful cultivated plants, namely crop plants and does exhibit an excellent herbicidal activity against them even at a low application rate thereof. According to such our findings, the present inventors have now completed the present inventions.

According to a first aspect of this invention, therefore, there is provided a 1-substituted-4-carbamoyl-1,2,4-triazol-5-one derivative represented by the general formula (I)

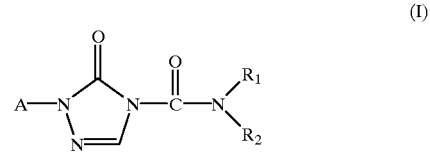

wherein:

(i) A is an unsubstituted or substituted phenyl group represented by the formula

in which X may be the same or different and is a halogen atom, a lower alkyl group, a lower haloalkyl group, a lower alkoxy group, a lower haloalkoxy group, cyano group, nitro group, methylthio group, methylsulfinyl group, methylsulfonyl group, phenoxy group, acetylamino group or trifluoroacetylamino group, and n is 0 or an integer of 1 to 5, or (ii) A is 1-naphthyl group of the formula

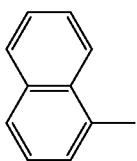

or 5,6,7,8-tetrahydro-1-naphthyl group of the formula

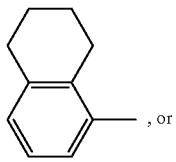, or (iii) A is an unsubstituted or substituted benzyl group or phenethyl group represented by the formula

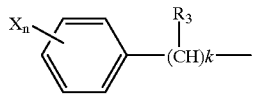

in which X and n have the same meanings as defined above, $R_3$ is hydrogen atom or methyl group and k denotes an integer of 1 to 2;

$R_1$ is a lower alkyl group, a lower alkenyl group, a lower alkynyl group or a lower cycloalkyl group; and $R_2$ is a lower alkyl group, a lower cycloalkyl group or an unsubstituted or substituted phenyl group having the formula

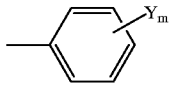

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with a halogen atom; or $R_2$ is an unsubstituted or substituted pyridyl group having the formula

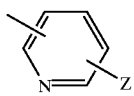

in which Z is hydrogen atom or chlorine atom.

The new 1,2,4-triazol-5-one derivative represented by the general formula (I) according to the first aspect of this invention has a characteristic chemical structure in that the 1-position of the 1,2,4-triazol-5-one ring is substituted by an unsubstituted or substituted phenyl group, 1-naphthyl group or an aralkyl group and also that the 4-position of said ring is substituted by an N,N-di-substituted carbamoyl group.

With the derivative of the general formula (I) above, the term "a lower alkyl group" used for the definitions of $R_1$, $R_2$, X and Y means a straight-chain or branched-chain alkyl group having 1 to 6 carbon atoms, such as methyl, ethyl, n-propyl, isopropyl, n-butyl, isobutyl, s-butyl, t-butyl, n-pentyl, isopentyl, 2-methylbutyl, neopentyl, n-hexyl, 4-methylpentyl, 3-methylpentyl, 2-methylpentyl, 3,3-dimethylbutyl, 1,1-dimethylbutyl, 1,3-dimethylbutyl, 2,3-dimethylbutyl, 1-ethylbutyl, 1-ethyl-2-methyl-propyl, 1-methyl-1-ethypropyl, 1-methyl-2-ethylpropyl, 2-methyl-1-ethylpropyl or 2-methyl-2-ethylpropyl group.

The term "a lower alkenyl group" used for the definition of $R_1$ given in the general formula (I) means a straight-chain or branched-chain alkynyl group having 3 to 6 carbon atoms, such as vinyl, 1-propenyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 2-pentenyl, 3-pentenyl, 4-pentenyl, 2-hexenyl, 3-hexenyl or 4-hexenyl group.

The term "a lower alkynyl group" used for the definition of $R_1$ given in the general formula (I) means a straight-chain or branched-chain alkenyl group having 3 to 6 carbon atoms, such as 2-propynyl, 1-methyl-2-propynyl, 2-butynyl, 1-methyl-2-butynyl, 1-ethyl-2-butynyl, 3-butynyl, 2-methyl-3-butynyl, 2-pentynyl, 4-pentynyl, 2-hexynyl, 3-hexynyl, 4-hexynyl or 5-hexynyl group.

The term "a cycloalkyl group" used for the definitions of $R_1$ and $R_2$ given in the general formula (I) means a cycloalkyl group having 3 to 7 carbon atoms which may have a branched-chain and which maybe, for example, cyclopropyl, cyclobutyl, cyclopentyl, cyclohexyl, 2-methylcyclopropyl, 2-methylcyclopentyl or 2-methylcyclohexyl group.

The halogen atom set forth in the definitions of X and Y given in the general formula (I) means chlorine, bromine, fluorine or iodine atom.

The term "a lower haloalkyl group" used for the definitions of X and Y given in the general formula (I) means a lower alkyl group having as substituent(s) one or more of halogen atoms such as chlorine, bromine, fluorine or iodine atom, which maybe, for example, trifluoromethyl, chloromethyl, bromomethyl, dichloromethyl, difluoromethyl, trichloromethyl, 2-chloroethyl, 2-bromoethyl, 1,1-difluorethyl, 2,2,2-trifluoroethyl, 3-chloropropyl or 3-iodopropyl group.

The term "a lower alkoxy group" used for the definitions of X and Y given in the general formula (I) means a straight-chain or branched-chain alkoxy group having 1 to 6 carbon atoms, such as methoxy, ethoxy, n-propoxy, isopropoxy, n-butoxy, isobutoxy, s-butoxy, t-butoxy, n-pentyloxy, isopentyloxy or n-hexyloxy group.

The term "a lower haloalkoxy group" used for the definitions of X and Y given in the general formula (I) means a haloalkoxy group having 1 to 6 carbon atoms, such as difluoromethoxy, trifluoromethoxy and 2,2,2-trifluoroethoxy group.

The term "benzyl group of which benzene ring may be substituted with a halogen atom", which is used for the definition of $R_2$ given in the general formula (I), means benzyl group, or a halo-benzyl group such as 2-chlorobenzyl group, 3-chlorobenzyl group, 4-chlorobenzyl group, 2-fluorobenzyl group, 3-fluorobenzyl group or 4-fluorobenzyl group.

The term "unsubstituted or substituted pyridyl group" used for the definition of $R_2$ given in the general formula (I) means, for example, 2-pyridyl group, 4-pyridyl group, 5-chloro-2-pyridyl group and others.

The 1-substituted-4-carbamoyl-1,2,4-triazol-5-one derivative represented by the general formula (I) may preferably be such a 1-substituted-4-carbamoyl-1,2,4-triazol-5-one derivative of the general formula (I) wherein $R_1$ is a lower alkyl group, $R_2$ is a mono-halo or di-halo-substituted phenyl group, X is a halogen atom, a lower alkyl group or a lower haloalkyl group and n is 0 or an integer of 1 to 2. Also, said derivative may preferably be such a 1-substituted-4-carbamoyl-1,2,4-triazol-5-one derivative of the general formula (I) wherein $R_1$ is a lower alkyl group, $R_2$ is a lower cycloalkyl group, X is a halogen atom, a lower alkyl group or a lower haloalkyl group and n is 0 or an integer of 1 to 2.

Further, the derivative of the formula (I) may preferably be such a 1-substituted-4-carbamoyl-1,2,4-triazol-5-one derivative of the general formula (I) wherein $R_1$ is isopropyl group, $R_2$ is a mono-halo-substituted or difluoro-substituted phenyl group, X is a halogen atom or a lower alkyl group and n is 0 or an integer of 1 to 2.

The 1-substituted-4-carbamoyl-1,2,4-triazol-5-one derivative represented by the general formula (I) according to the first aspect of this invention may be classified broadly into the following three classes of the derivatives, namely the derivatives having the following general formulae (Ia), (Ib) and (Ic), respectively.

(1) A 1-phenyl-4-(N,N-di-substituted carbamoyl)-1,2,4-triazol-5-one derivative represented by the general formula (Ia)

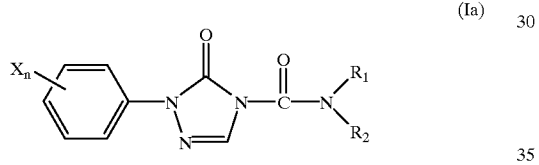

wherein:
X has the same meaning as defined in the general formula (I), namely X may be the same or different and is a halogen atom, a lower alkyl group, a lower haloalkyl group, a lower alkoxy group, a lower haloalkoxy group, cyano group, nitro group, methylthio group, methylsulfinyl group, methylsulfonyl group, phenoxy group, acetylamino group or trifluoroacetylamino group;
n is 0 or an integer of 1 to 5; and
$R_1$ and $R_2$ have the same meanings as defined in the general formula (I), namely $R_1$ is a lower alkyl group, a lower alkenyl group, a lower alkynyl group or a lower cycloalkyl group, and $R_2$ is a lower alkyl group, a lower cycloalkyl group or an unsubstituted or substituted phenyl group having the formula

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with halogen atom(s); or $R_2$ is an unsubstituted or substituted pyridyl group having the formula

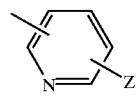

in which Z is a hydrogen atom or chlorine atom;

(2) A 1-naphthyl-4-(N,N-di-substituted carbamoyl)-1,2,4-triazol-5-one derivative represented by the general formula (Ib)

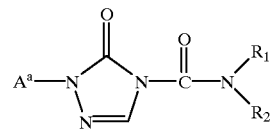

in which:
$A^a$ is 1-naphthyl group of the formula

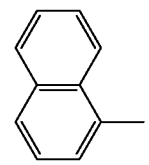

or 5,6,7,8-tetrahydrol-naphthyl group of the formula

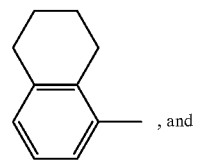

,and $R_1$ and $R_2$ have the same meanings as defined in the general formula (I), namely $R_1$ is a lower alkyl group, a lower alkenyl group, a lower alkynyl group or a lower cycloalkyl group, and $R_2$ is a lower alkyl group, a lower cycloalkyl group or an unsubstituted or substituted phenyl group having the formula

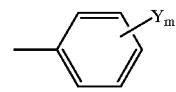

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with a halogen atom; or $R_2$ is an unsubstituted or substituted pyridyl group having the formula

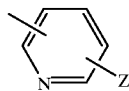

in which Z is a hydrogen atom or chlorine atom; and (3) A 1-aralkyl-4-(N,N-disubstituted carbamoyl)-1,2,4-triazol-5-one derivative represented by the general formula (Ic)

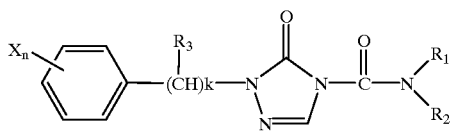

in which:

X has the same meaning as defined in the general formula (I), namely X may be the same or different and is a halogen atom, a lower alkyl group, a lower haloalkyl group, a lower alkoxy group, a lower haloalkoxy group, cyano group, nitro group, methylthio group, methylsulfinyl group, methylsulfonyl group, phenoxy group, acetylamino group or trifluoroacetylamino group;

n is 0 or an integer of 1 to 5;

$R_1$ and $R_2$ have the same meanings as defined in the general formula (I), namely $R_1$ is a lower alkyl group, a lower alkenyl group, a lower alkynyl group or a lower cycloalkyl group, and $R_2$ is a lower alkyl group, a lower cycloalkyl group or an unsubstituted or substituted phenyl group having the formula

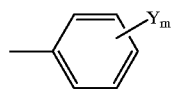

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with halogen atom(s); or $R_2$ is an unsubstituted or substituted pyridyl group having the formula

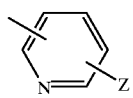

in which Z is a hydrogen atom or chlorine atom;

$R_3$ is a hydrogen atom or methyl group; and k is an integer of 1 or 2.

The derivative of the general formula (Ia) above may preferably be such a 1-phenyl-4-(N,N-di-substituted carbamoyl)-1,2,4-triazol-5-one derivative represented by the general formula (Ia-1)

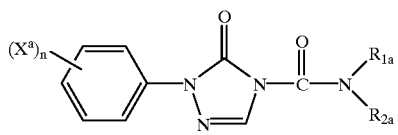

where $R_{1a}$ is a lower alkyl group, $R_{2a}$ is a mono-halo- or di-halo-substituted phenyl group, $X^a$ is a halogen atom, a lower alkyl group or a lower haloalkyl group, and n is 0 or an integer of 1 to 2.

In addition, the derivative of the general formula (Ia) may preferably be such a 1-phenyl-4-(N,N-di-substituted carbamoyl) -1,2,4-triazol-5-one derivative represented by the general formula (Ia-1-1)

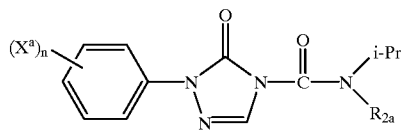

where i-Pr means isopropyl group, $R_{2a}$ is a mono-halo- or di-halo-substituted phenyl group, $X^a$ is a halogen atom, a lower alkyl group or a lower haloalkyl group, and n is 0 or an integer of 1 to 2.

Furthermore, the derivative of the general formula (Ia-1-1) may be a 1-phenyl-4-(N,N-di-substituted carbamoyl)-1,2,4-triazol-5-one derivative represented by the general formula (Ia-1-2)

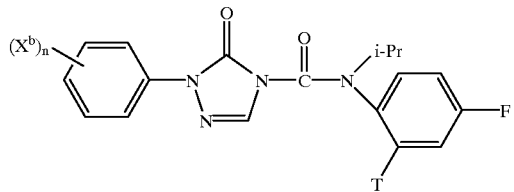

where i-Pr means isopropyl group, T is hydrogen atom or fluorine atom, $X^b$ may be the same or different and is chlorine atom, bromine atom, fluorine atom, methyl group, ethyl group or trifluoromethyl group, and n is 0 or an integer of 1 to 2.

Representative particular examples of the 1-phenyl-4-(N,N-di-substituted carbamoyl) -1,2, 4-triazol-5-one derivative of the general formula (Ia-1-2), which is embraced in the derivative of the general formula (I) according to the first aspect of this invention, are particular compounds shown in Table 1a given hereinafter. Some of the preferred exemplary compounds include a class of compounds listed below:

(1) 1-phenyl-(N-isopropyl-N-4-fluoro or 2,4-difluorophenyl-carbamoyl)-1,2,4-triazol-5-one (Compound No.4 or No.8 in Table 1a given hereinafter), (2) 1-(2-chlorophenyl)-4-(N-isopropyl-N-4-fluoro or 2,4-difluorophenyl-carbamoyl)-1,2,4-triazol-5-one (Compound No.38 or No.35 in Table 1a given hereinafter), (3) 1-(3-chlorophenyl)-4-(N-isopropyl-N-4-fluoro or 2,4-difluorophenyl-carbamoyl)-1,2,4-triazol-5-one (Compound No.75 or No.76 in Table 1a given hereinafter), (4) 1-(2-fluorophenyl)-4-(N-isopropyl-N-4-fluoro or 2,4-difluorophenyl-carbamoyl)-1,2,4-triazol-5-one (Compound No.165 or No.166 in Table 1a given hereinafter), (5) 1-(2,4-difluorophenyl)-4-(N-isopropyl-N-4-fluoro or 2,4-difluorophenyl-carbamoyl)-1,2,4-triazol-5-one (Compound No.184 or No.181 in Table 1a given hereinafter), (6) 1-(2-fluoro-4-chlorophenyl)-4-(N-isopropyl-N-4-fluoro or 2,4-difluorophenyl-carbamoyl)-1,2,4-triazol-5-one (Compound No.322 in Table 1a given hereinafter), (7) 1-(2-methylphenyl)-4-(N-isopropyl-N-4-fluoro or 2,4-difluorophenyl-carbamoyl)-1,2,4-triazol-5-one (Compound No.332 or No.331 in Table 1a given hereinafter), (8) 1-(2,3-dimethylphenyl)-4-(N-isopropyl-N-4-fluoro or 2,4-difluorophenyl-carbamoyl)-1,2,4-triazol-5-one (Compound No.581 or No.582 in Table 1a given hereinafter), or (9) 1-(2-chloro-4-methylphenyl)-4-(N-isopropyl-N-4-fluoro or 2,4-difluorophenyl-carbamoyl)-1,2,4-triazol-5-one (Compound No.634 or No.633 in Table 1a given hereinafter).

In addition, further examples of the preferred compounds include also compounds of Compound Nos.231, 234, 369, 270, 281, 284, 576, 577, 587, 591, 592, 596, 597, 635, 636, 637, 638, 639 and 640 shown in the following Table 1a.

Furthermore, the 1-phenyl-4-(N,N-di-substituted carbamoyl)-1,2,4-triazol-5-one derivative of the general formula (Ia) may preferably be such a 1-phenyl-4-(N,N-di-substituted carbamoyl)-1,2,4-triazol-5-one derivative represented by the general formula (Ia-2)

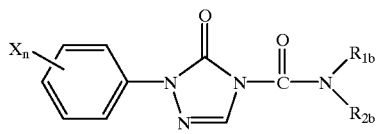

(Ia-2)

where X and n have the same meanings as defined in the general formula (I) or (Ia), $R_{1b}$ is a lower alkyl group, and $R_{2b}$ is a lower cycloalkyl group.

In particular, the derivative of the general formula (Ia-2) may preferably be a 1-phenyl-4-(N,N-di-substituted carbamoyl)-1,2,4-triazol-5-one derivative of the above general formula (Ia-2) where X is chlorine atom, fluorine atom, methyl group, ethyl group, trifluoromethyl group or trifluoromethyloxy group, n is 0 or an integer of 1 to 2, $R_{1b}$ is methyl group, ethyl group, n-propyl group or isopropyl group, and $R_{2b}$ is cyclopropyl group , cyclopentyl group or cyclohexyl group.

The 1-naphthyl-4-(N,N-di-substituted carbamoyl)-1,2,4-triazol-5-one derivative of the general formula (Ib) given hereinbefore is preferably such derivative of the general formula (Ib) where $R_1$ is a lower alkyl group, particularly isopropyl group, and $R_2$ is monohalo or dihalo-substituted phenyl group, particularly 4-fluoro or 2,4-difluorophenyl group, and n is 0 or an integer of 1 to 2.

Representative particular examples of the derivative of the general formula (Ib) include compounds of Compound Nos.649 to 652 shown in Table 1b given hereinafter. Particularly preferred compound is 1-(5,6,7,8-tetrahydro-1-naphthyl)-4-(N-isopropyl-N-2,4-difluorophenyl-carbamoyl)-1,2,4-triazol-5-one (Compound No.650).

The 1-aralkyl-4-(N,N-di-substituted carbamoyl)-1,2,4-triazol-5-one derivative of the general formula (Ic) shown hereinbefore according to the first aspect of this invention may preferably be a 1-aralkyl-4-(N,N-di-substituted carbamoyl) -1,2,4-triazol-5-one derivative represented by the general formula (Ic-1)

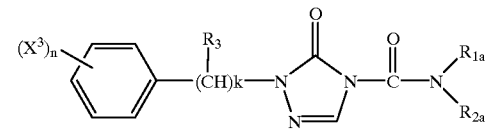

(Ic-1)

where $R_{1a}$ is a lower alkyl group, $R_{2a}$ is a mono-halo- or di-halo-substituted phenyl group, $X^a$ is a halogen atom, a lower alkyl group or a lower haloalkyl group, n is 0 or an integer of 1 to 2 and k is an integer of 1 or 2.

Particularly preferred derivative of the general formula (Ic-1) is a 1-aralkyl-4-(N,N-di-substituted carbamoyl)-1,2,4-triazol-5-one derivative represented by the general formula (Ic-1-1)

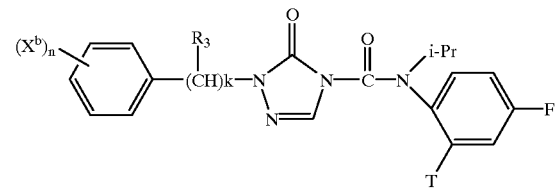

(Ic-1-1)

in which i-Pr means isopropyl group, T is hydrogen atom or fluorine atom, $X^b$ may be the same or different and is chlorine atom, bromine atom, fluorine atom, methyl group, ethyl group or trifluoromethyl group, n is 0 or an integer of 1 to 2, $R_3$ is hydrogen atom or methyl group and k is an integer of 1 or 2.

Representative examples of the 1-aralkyl-4-(N,N-di-substituted carbamoyl)-1,2,4-triazol-5-one derivative of the general formula (Ic) include compounds of Compound Nos.653 to 684 shown in Table 1c given hereinafter. Particularly preferred compounds among them are 1-(2,3-dichlorobenzyl)-4-(N-isopropyl-N-2,4-difluorophenyl-carbamoyl)-1,2,4-triazol-5-one (Compound No.662) and 1-(2-chloro-a-methylbenzyl)-4-(N-isopropyl-N-2,4-difluorophenyl-carbamoyl)-1,2,4-triazol-5-one (Compound No.675).

According to a second aspect of this invention, there is provided a herbicidal composition comprising as an active ingredient the 1-substituted-4-carbamoyl-1,2,4-triazol-5-one derivative represented by the general formula (I)

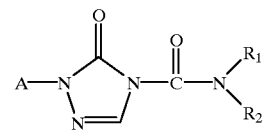

(I)

wherein A, $R_1$ and $R_2$ have the same meanings as defined above.

The herbicidal composition of the second aspect of this invention may contain as the active ingredient the 1-phenyl-4-carbamoyl-1,2,4-triazol-5-one derivative of the general formula (Ia) as defined above. Furthermore, the herbicidal composition also may contain as the active ingredient the 1-naphthyl-4-carbamoyl-1,2,4-triazol-5-one derivative of the general formula (Ib) as defined above.

Besides, the herbicidal composition of the second aspect of this invention also may contain as the active ingredient the 1-aralkyl-4-carbamoyl-1,2,4-triazol-5-one derivative of the general formula (Ic) as defined above.

BEST MODE FOR CARRYING OUT THE INVENTION

Next, representative particular examples of the 1-substituted-4-carbamoyl-1,2,4-triazol-5-one derivative of the general formula (Ia) according to the first aspect of this invention are shown in Table 1a given hereinafter. In addition, representative particular examples of the 1-naphthyl-4-(N,N-disubstituted carbamoyl)-1,2,4-triazol-5-one derivative of the general formula (Ib) are shown in Table 1b given hereinafter, and representative examples of the 1-aralkyl-4-(N,N-disubstituted carbamoyl)-1,2,4-triazol-5-one derivative of the general formula (Ic) are shown in Table 1c given hereinafter.

Compound Nos. given in these Table 1a, Table 1b and Table 1c are referred to also in Examples and Test Examples given after.

In Table 1a, such compounds where $X_n$ is shown as H indicate that the phenyl group exhibited in the formula (I) does not have the substituent (X), namely such compounds where n=0. Furthermore, in Table 1a to Table 1c, Me denotes methyl group, Et denotes ethyl group, Pr denotes propyl group and Bu denotes butyl group. For instance, i-Pr denotes isopropyl group, n-Pr denotes n-propyl group, i-Bu denotes i-butyl group, n-Bu denotes n-butyl group and sec-Bu denotes secondary butyl group.

TABLE 1a

General formula (Ia)

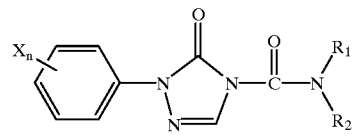

| Compound No. | $X_n$ | $R_1$ | $R_2$ | Physical data |
|---|---|---|---|---|
| 1 | H | i-Pr | ⌬ (phenyl) | mp 144–145° C. |
| 2 | H | i-Pr | 2-F-phenyl | |
| 3 | H | i-Pr | 3-F-phenyl | |
| 4 | H | i-Pr | 4-F-phenyl | mp 142–143° C. |
| 5 | H | i-Pr | 2-Cl-phenyl | |
| 6 | H | i-Pr | 3-Cl-phenyl | |

TABLE 1a-continued
General formula (Ia)
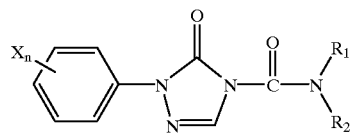
| Compound No. | $X_n$ | $R_1$ | $R_2$ | Physical data |
|---|---|---|---|---|
| 7 | H | i-Pr | ![4-chlorophenyl] | |
| 8 | H | i-Pr | ![2,4-difluorophenyl] | mp 104–106° C. |
| 9 | H | i-Pr | ![2,4-dichlorophenyl] | |
| 10 | H | i-Pr | ![4-methylphenyl] | |
| 11 | H | i-Pr | ![4-trifluoromethylphenyl] | |
| 12 | H | i-Pr | ![4-methoxyphenyl] | |
| 13 | H | i-Pr | i-Pr | mp 174–175° C. |
| 14 | H | i-Pr | ![cyclohexyl] | mp 136–137° C. |
| 15 | H | Et | Et | |
| 16 | H | Et | ![cyclohexyl] | mp 123–124° C. |
| 17 | H | n-Pr | ![cyclopentyl] | mp 79–80° C. |
| 18 | H | —CH$_2$CH=CH$_2$ | ![cyclohexyl] | mp 101–102° C. |

TABLE 1a-continued
General formula (Ia)
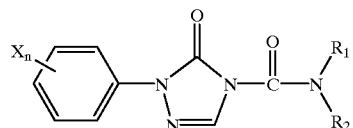
| Compound No. | $X_n$ | $R_1$ | $R_2$ | Physical data |
|---|---|---|---|---|
| 19 | H | —CH$_2$C≡CH | 2,4-difluorophenyl | |
| 20 | H | i-Bu | 2,4-difluorophenyl | |
| 21 | H | i-Pr | —CH$_2$-phenyl | |
| 22 | H | i-Pr | —CH$_2$-(4-F-phenyl) | |
| 23 | H | i-Pr | 2-pyridyl | |
| 24 | H | i-Pr | 5-Cl-2-pyridyl | |
| 25 | 2-Cl | Me | 2,4-difluorophenyl | mp 141–143° C. |
| 26 | 2-Cl | Et | 2,4-difluorophenyl | mp 110–111° C. |
| 27 | 2-Cl | n-Pr | 2,4-difluorophenyl | mp 94–95° C. |
| 28 | 2-Cl | n-Bu | 2,4-difluorophenyl | mp 90–91° C. |

TABLE 1a-continued
General formula (Ia)
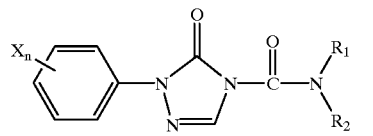
| Compound No. | $X_n$ | $R_1$ | $R_2$ | Physical data |
| --- | --- | --- | --- | --- |
| 29 | 2-Cl | i-Bu | 2,4-difluorophenyl | mp 112–114° C. |
| 30 | 2-Cl | sec-Bu | 2,4-difluorophenyl | mp 88–89° C. |
| 31 | 2-Cl | cyclopentyl | 2,4-difluorophenyl | mp 90–91° C. |
| 32 | 2-Cl | —CH$_2$CH=CH$_2$ | 2,4-difluorophenyl | mp 105–106° C. |
| 33 | 2-Cl | —CH$_2$C≡CH | 2,4-difluorophenyl | mp 97–99° C. |
| 34 | 2-Cl | i-Pr | phenyl | mp 132–134° C. |
| 35 | 2-Cl | i-Pr | 2,4-difluorophenyl | mp 146–147° C. |
| 36 | 2-Cl | i-Pr | 2-fluorophenyl | mp 106–168° C. |
| 37 | 2-Cl | i-Pr | 3-fluorophenyl | |

TABLE 1a-continued
General formula (Ia)
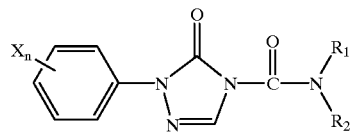
| Compound No. | X<sub>n</sub> | R₁ | R₂ | Physical data |
|---|---|---|---|---|
| 38 | 2-Cl | i-Pr | 4-F-phenyl | mp 118–120° C. |
| 39 | 2-Cl | i-Pr | 2-Cl-phenyl | mp 125–127° C. |
| 40 | 2-Cl | i-Pr | 3-Cl-phenyl | mp 134–135° C. |
| 41 | 2-Cl | i-Pr | 4-Cl-phenyl | mp 154–156° C. |
| 42 | 2-Cl | i-Pr | 2,4-diCl-phenyl | mp 187–189° C. |
| 43 | 2-Cl | i-Pr | 2-Cl-4-F-phenyl | |
| 44 | 2-Cl | i-Pr | 2-F-4-Cl-phenyl | mp 164–166° C. |
| 45 | 2-Cl | i-Pr | 2,3,4-triF-phenyl | mp 80–82° C. |
| 46 | 2-Cl | i-Pr | 2,4,5-triF-phenyl | |

TABLE 1a-continued

General formula (Ia)

| Compound No. | $X_n$ | $R_1$ | $R_2$ | Physical data |
|---|---|---|---|---|
| 47 | 2-Cl | i-Pr | 2-methylphenyl | |
| 48 | 2-Cl | i-Pr | 3-methylphenyl | |
| 49 | 2-Cl | i-Pr | 4-methylphenyl | |
| 50 | 2-Cl | i-Pr | 4-OMe-phenyl | |
| 51 | 2-Cl | i-Pr | 4-OCF$_3$-phenyl | |
| 52 | 2-Cl | i-Pr | 4-CF$_3$-phenyl | |
| 53 | 2-Cl | i-Pr | 4-CN-phenyl | |
| 54 | 2-Cl | i-Pr | 3,5-dichlorophenyl | mp 114–116° C. |
| 55 | 2-Cl | i-Pr | 4-Br-phenyl | |
| 56 | 2-Cl | i-Pr | 4-I-phenyl | |

TABLE 1a-continued

General formula (Ia)

| Compound No. | $X_n$ | $R_1$ | $R_2$ | Physical data |
|---|---|---|---|---|
| 57 | 2-Cl | i-Pr | 2,5-dimethylphenyl | |
| 58 | 2-Cl | i-Pr | 4-ethylphenyl | |
| 59 | 2-Cl | i-Pr | 2-methyl-4-chlorophenyl | |
| 60 | 2-Cl | i-Pr | 2-trifluoromethyl-4-chlorophenyl | |
| 61 | 2-Cl | i-Pr | 4-OCHF$_2$-phenyl | |
| 62 | 2-Cl | n-Pr | cyclopentyl | $n_D^{18}$1.5556 |
| 63 | 2-Cl | —CH$_2$C(Me)=CH$_2$ | Et | $n_D^{18}$1.5558 |
| 64 | 2-Cl | cyclopropylmethyl | 2,4-difluorophenyl | |
| 65 | 2-Cl | Et | Et | mp 71–72° C. |
| 66 | 2-Cl | Et | cyclohexyl | mp 105–106° C. |
| 67 | 2-Cl | —CH$_2$CH=CH$_2$ | Et | |
| 68 | 2-Cl | —CH$_2$C≡CH | Et | |
| 69 | 2-Cl | —CH$_2$CH=CH$_2$ | cyclohexyl | mp 83–85° C. |

TABLE 1a-continued
General formula (Ia)
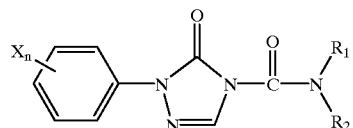
| Compound No. | $X_n$ | $R_1$ | $R_2$ | Physical data |
|---|---|---|---|---|
| 70 | 2-Cl | —CH$_2$C≡CH | cyclohexyl-CH$_2$— | |
| 71 | 2-Cl | i-Pr | i-Pr | mp 150–151° C. |
| 72 | 2-Cl | i-Pr | —CH$_2$-(4-F-C$_6$H$_4$) | $n_D^{18}$ 1.5669 |
| 73 | 2-Cl | i-Pr | (2-Cl-pyridin-3-yl)methyl | mp 125–127° C. |
| 74 | 2-Cl | i-Pr | (5-Cl-pyridin-2-yl)methyl | mp 131–133° C. |
| 75 | 3-Cl | i-Pr | —CH$_2$-(4-F-C$_6$H$_4$) | mp 154–155° C. |
| 76 | 3-Cl | i-Pr | —CH$_2$-(2,4-F$_2$-C$_6$H$_3$) | mp 173–174° C. |
| 77 | 4-Cl | n-Pr | —CH$_2$-(2,4-F$_2$-C$_6$H$_3$) | |
| 78 | 4-Cl | n-Bu | —CH$_2$-(2,4-F$_2$-C$_6$H$_3$) | |
| 79 | 4-Cl | i-Bu | —CH$_2$-(2,4-F$_2$-C$_6$H$_3$) | |
| 80 | 4-Cl | sec-Bu | —CH$_2$-(2,4-F$_2$-C$_6$H$_3$) | |

TABLE 1a-continued
General formula (Ia)
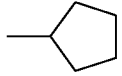
| Compound No. | $X_n$ | $R_1$ | $R_2$ | Physical data |
|---|---|---|---|---|
| 81 | 4-Cl | 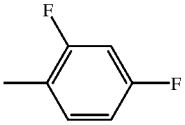 | 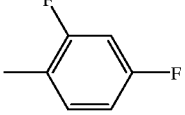 | |
| 82 | 4-Cl | —CH$_2$CH═CH$_2$ | | |
| 83 | 4-Cl | —CH$_2$C≡CH | | |
| 84 | 4-Cl | i-Pr | 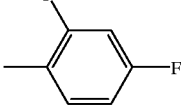 | |
| 85 | 4-Cl | i-Pr | 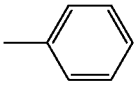 | mp 206–208° C. |
| 86 | 4-Cl | i-Pr | 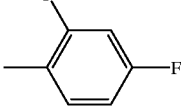 | |
| 87 | 4-Cl | i-Pr | 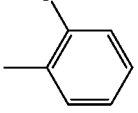 | |
| 88 | 4-Cl | i-Pr | 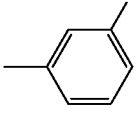 | mp 181–183° C. |
| 89 | 4-Cl | i-Pr |  | |

TABLE 1a-continued
General formula (Ia)
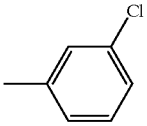
| Compound No. | $X_n$ | $R_1$ | $R_2$ | Physical data |
|---|---|---|---|---|
| 90 | 4-Cl | i-Pr | 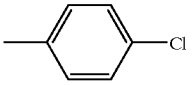 | |
| 91 | 4-Cl | i-Pr | 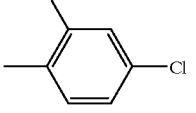 | |
| 92 | 4-Cl | i-Pr | 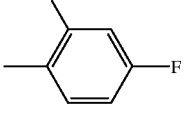 | |
| 93 | 4-Cl | i-Pr | 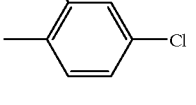 | |
| 94 | 4-Cl | i-Pr | 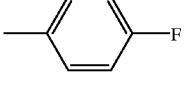 | |
| 95 | 4-Cl | i-Pr | 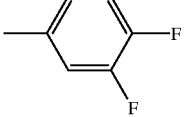 | |
| 96 | 4-Cl | i-Pr | 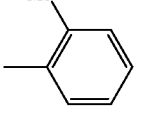 | |
| 97 | 4-Cl | i-Pr | 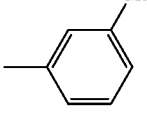 | |
| 98 | 4-Cl | i-Pr |  | |

TABLE 1a-continued
General formula (Ia)
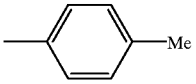
| Compound No. | $X_n$ | $R_1$ | $R_2$ | Physical data |
|---|---|---|---|---|
| 99 | 4-Cl | i-Pr | 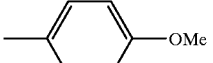 | |
| 100 | 4-Cl | i-Pr | 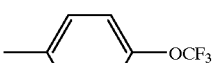 | |
| 101 | 4-Cl | i-Pr | 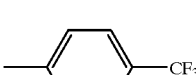 | |
| 102 | 4-Cl | i-Pr | 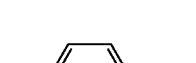 | |
| 103 | 4-Cl | i-Pr | 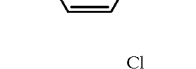 | |
| 104 | 4-Cl | i-Pr | 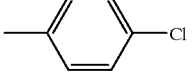 | |
| 105 | 4-Cl | i-Pr | 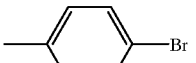 | |
| 106 | 4-Cl | i-Pr | 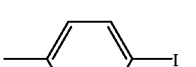 | |
| 107 | 4-Cl | i-Pr |  | |
| 108 | 4-Cl | i-Pr | 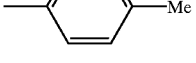 | |
| 109 | 4-Cl | i-Pr | | |

TABLE 1a-continued
General formula (Ia)
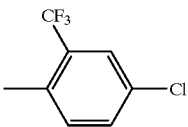
| Compound No. | X$_n$ | R$_1$ | R$_2$ | Physical data |
|---|---|---|---|---|
| 110 | 4-Cl | i-Pr | 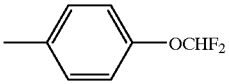 | |
| 111 | 4-Cl | i-Pr |  | |
| 112 | 4-Cl | 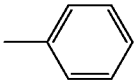 |  | |
| 113 | 4-Cl | 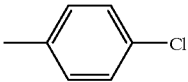 |  | |
| 114 | 4-Cl | 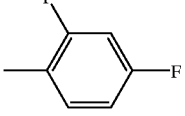 | 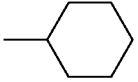 | |
| 115 | 4-Cl | Et | Et | |
| 116 | 4-Cl | Et | 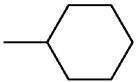 | |
| 117 | 4-Cl | —CH$_2$CH=CH$_2$ | Et | |
| 118 | 4-Cl | —CH$_2$C≡CH | Et | |
| 119 | 4-Cl | —CH$_2$CH=CH$_2$ | 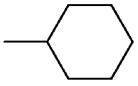 | |
| 120 | 4-Cl | —CH$_2$C≡CH | 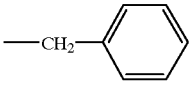 | |
| 121 | 4-Cl | i-Pr | 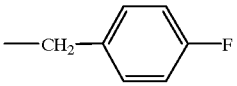 | |
| 122 | 4-Cl | i-Pr |  | |

TABLE 1a-continued

General formula (Ia)

| Compound No. | X$_n$ | R$_1$ | R$_2$ | Physical data |
|---|---|---|---|---|
| 123 | 4-Cl | i-Pr | 2-pyridylmethyl | |
| 124 | 4-Cl | i-Pr | (5-chloropyridin-2-yl)methyl | |
| 125 | 2-Br | Me | 2,4-difluorobenzyl | |
| 126 | 2-Br | Et | 2,4-difluorobenzyl | |
| 127 | 2-Br | n-Pr | 2,4-difluorobenzyl | |
| 128 | 2-Br | n-Bu | 2,4-difluorobenzyl | |
| 129 | 2-Br | i-Bu | 2,4-difluorobenzyl | |
| 130 | 2-Br | sec-Bu | 2,4-difluorobenzyl | |
| 131 | 2-Br | cyclopentylmethyl | 2,4-difluorobenzyl | |

TABLE 1a-continued
General formula (Ia)
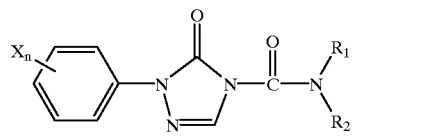
| Compound No. | $X_n$ | $R_1$ | $R_2$ | Physical data |
|---|---|---|---|---|
| 132 | 2-Br | —CH$_2$CH=CH$_2$ | 2,4-difluorophenyl | |
| 133 | 2-Br | —CH$_2$C≡CH | 2,4-difluorophenyl | |
| 134 | 2-Br | i-Pr | phenyl | |
| 135 | 2-Br | i-Pr | 2,4-difluorophenyl | mp 146–147° C. |
| 136 | 2-Br | i-Pr | 2-fluorophenyl | |
| 137 | 2-Br | i-Pr | 3-fluorophenyl | |
| 138 | 2-Br | i-Pr | 4-fluorophenyl | mp 104–105° C. |
| 139 | 2-Br | i-Pr | 2-chlorophenyl | |
| 140 | 2-Br | i-Pr | 3-chlorophenyl | |
| 141 | 2-Br | i-Pr | 4-chlorophenyl | |

TABLE 1a-continued
General formula (Ia)
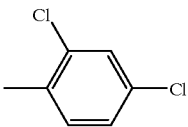
| Compound No. | $X_n$ | $R_1$ | $R_2$ | Physical data |
|---|---|---|---|---|
| 142 | 2-Br | i-Pr | 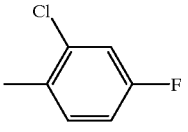 | |
| 143 | 2-Br | i-Pr | 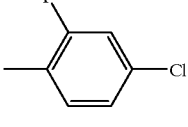 | |
| 144 | 2-Br | i-Pr | 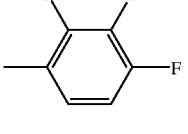 | |
| 145 | 2-Br | i-Pr | 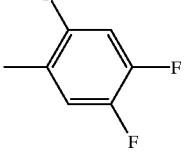 | |
| 146 | 2-Br | i-Pr | 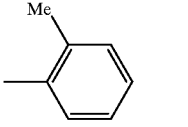 | |
| 147 | 2-Br | i-Pr | 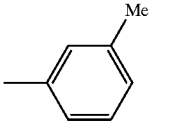 | |
| 148 | 2-Br | i-Pr | 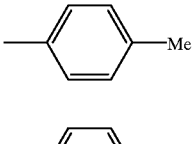 | |
| 149 | 2-Br | i-Pr | 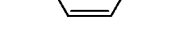 | |
| 150 | 2-Br | i-Pr | | |

TABLE 1a-continued

General formula (Ia)

| Compound No. | $X_n$ | $R_1$ | $R_2$ | Physical data |
|---|---|---|---|---|
| 151 | 2-Br | i-Pr | 4-OCF₃-C₆H₄ | |
| 152 | 2-Br | i-Pr | 4-CF₃-C₆H₄ | |
| 153 | 2-Br | i-Pr | 4-CN-C₆H₄ | |
| 154 | 2-Br | i-Pr | 3,4-Cl₂-C₆H₃ | |
| 155 | 2-Br | i-Pr | 4-Br-C₆H₄ | |
| 156 | 2-Br | i-Pr | 4-I-C₆H₄ | |
| 157 | 2-Br | i-Pr | 2,4-Me₂-C₆H₃ | |
| 158 | 2-Br | i-Pr | 4-Et-C₆H₄ | |
| 159 | 2-Br | i-Pr | 2-Me-4-Cl-C₆H₃ | |
| 160 | 2-Br | i-Pr | 2-CF₃-4-Cl-C₆H₃ | |
| 161 | 2-Br | i-Pr | 4-OCHF₂-C₆H₄ | |

TABLE 1a-continued
General formula (Ia)
| Compound No. | $X_n$ | $R_1$ | $R_2$ | Physical data |
|---|---|---|---|---|
| 162 | 2-Br | 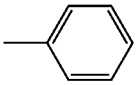 |  | |
| 163 | 2-Br |  | 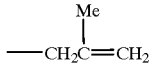 | |
| 164 | 2-F | $-CH_2\underset{\underset{Me}{\mid}}{C}=CH_2$ | Et | $n_D^{18}$ 1.5414 |
| 165 | 2-F | i-Pr |  | mp 126–127° C. |
| 166 | 2-F | i-Pr | 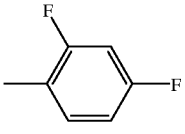 | mp 135–136° C. |
| 167 | 3-F | i-Pr |  | mp 134–136° C. |
| 168 | 3-F | i-Pr | 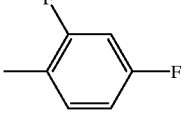 | mp 140–141° C. |
| 169 | 4-F | i-Pr |  | mp 120–121° C. |
| 170 | 4-F | i-Pr | 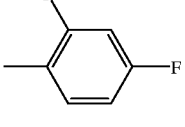 | mp 151–152° C. |
| 171 | 2,4-$F_2$ | Me | 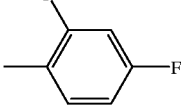 | |

TABLE 1a-continued
General formula (Ia)
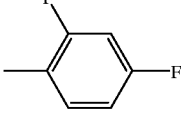
| Compound No. | $X_n$ | $R_1$ | $R_2$ | Physical data |
|---|---|---|---|---|
| 172 | 2,4-$F_2$ | Et | 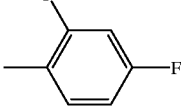 | |
| 173 | 2,4-$F_2$ | n-Pr | 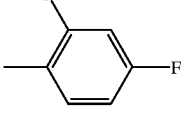 | |
| 174 | 2,4-$F_2$ | n-Bu | 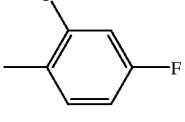 | |
| 175 | 2,4-$F_2$ | i-Bu | 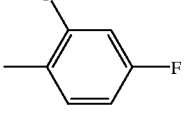 | |
| 176 | 2,4-$F_2$ | sec-Bu | 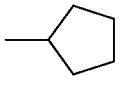 | |
| 177 | 2,4-$F_2$ | 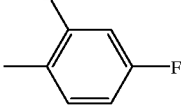 | 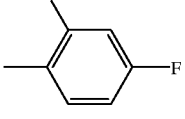 | |
| 178 | 2,4-$F_2$ | —$CH_2CH$=$CH_2$ | 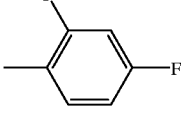 | |
| 179 | 2,4-$F_2$ | —$CH_2C$≡$CH$ | 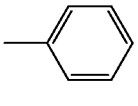 | |
| 180 | 2,4-$F_2$ | i-Pr | | |

TABLE 1a-continued
General formula (Ia)
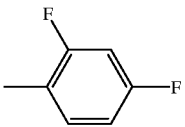
| Compound No. | $X_n$ | $R_1$ | $R_2$ | Physical data |
|---|---|---|---|---|
| 181 | 2,4-$F_2$ | i-Pr | 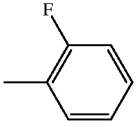 | mp 166–167° C. |
| 182 | 2,4-$F_2$ | i-Pr | 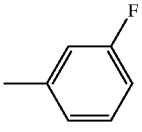 | |
| 183 | 2,4-$F_2$ | i-Pr | 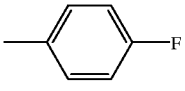 | |
| 184 | 2,4-$F_2$ | i-Pr | 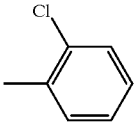 | mp 142–143° C. |
| 185 | 2,4-$F_2$ | i-Pr | 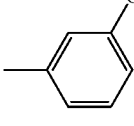 | |
| 186 | 2,4-$F_2$ | i-Pr | 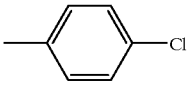 | |
| 187 | 2,4-$F_2$ | i-Pr | 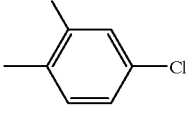 | |
| 188 | 2,4-$F_2$ | i-Pr | 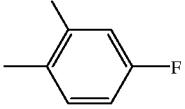 | |
| 189 | 2,4-$F_2$ | i-Pr |  | |

TABLE 1a-continued
General formula (Ia)
| Compound No. | $X_n$ | $R_1$ | $R_2$ | Physical data |
|---|---|---|---|---|
| 190 | 2,4-$F_2$ | i-Pr | 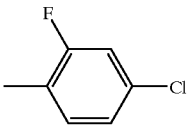 | |
| 191 | 2,4-$F_2$ | i-Pr | 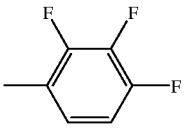 | |
| 192 | 2,4-$F_2$ | i-Pr | 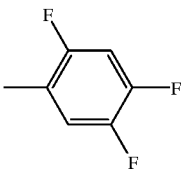 | |
| 193 | 2,4-$F_2$ | i-Pr | 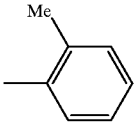 | |
| 194 | 2,4-$F_2$ | i-Pr | 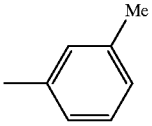 | |
| 195 | 2,4-$F_2$ | i-Pr | 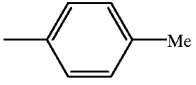 | |
| 196 | 2,4-$F_2$ | i-Pr | 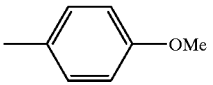 | |
| 197 | 2,4-$F_2$ | i-Pr | 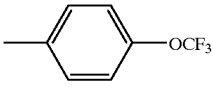 | |
| 198 | 2,4-$F_2$ | i-Pr | 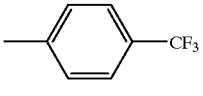 | |
| 199 | 2,5-$F_2$ | i-Pr | 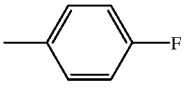 | mp 105–107° C. |

TABLE 1a-continued
General formula (Ia)
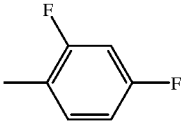
| Compound No. | $X_n$ | $R_1$ | $R_2$ | Physical data |
|---|---|---|---|---|
| 200 | 2,5-$F_2$ | i-Pr | 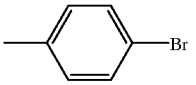 2,4-difluorophenyl | mp 126–127° C. |
| 201 | 2,4-$F_2$ | i-Pr |  4-Br-phenyl | |
| 202 | 2,4-$F_2$ | i-Pr | 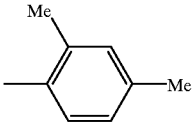 4-I-phenyl | |
| 203 | 2,4-$F_2$ | i-Pr | 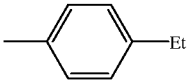 2,4-diMe-phenyl | |
| 204 | 2,4-$F_2$ | i-Pr | 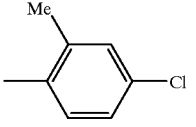 4-Et-phenyl | |
| 205 | 2,4-$F_2$ | i-Pr | 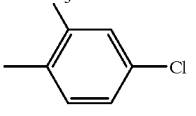 2-Me-4-Cl-phenyl | |
| 206 | 2,4-$F_2$ | i-Pr | 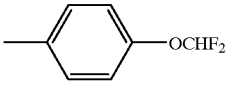 2-$CF_3$-4-Cl-phenyl | |
| 207 | 2,4-$F_2$ | i-Pr |  4-$OCHF_2$-phenyl | |
| 208 | 2,4-$F_2$ | 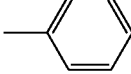 cyclopropyl |  phenyl | |
| 209 | 2,4-$F_2$ | cyclopropyl | 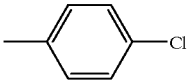 4-Cl-phenyl | |

TABLE 1a-continued

General formula (Ia)

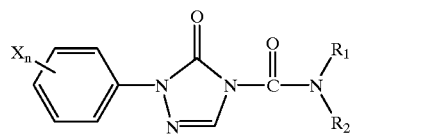

| Compound No. | $X_n$ | $R_1$ | $R_2$ | Physical data |
|---|---|---|---|---|
| 210 | 2,4-$F_2$ | cyclopropyl | 2,4-difluorophenyl | |
| 211 | 2,4-$F_2$ | Et | Et | |
| 212 | 2,4-$F_2$ | Et | cyclohexyl | |
| 213 | 2,4-$F_2$ | —$CH_2CH=CH_2$ | Et | |
| 214 | 2,4-$F_2$ | —$CH_2C\equiv CH$ | Et | |
| 215 | 2,4-$F_2$ | —$CH_2CH=CH_2$ | cyclohexyl | |
| 216 | 2,4-$F_2$ | —$CH_2C\equiv CH$ | cyclohexyl | |
| 217 | 2,4-$F_2$ | i-Pr | —$CH_2$-phenyl | |
| 218 | 2,4-$F_2$ | i-Pr | —$CH_2$-(4-fluorophenyl) | |
| 219 | 2,4-$F_2$ | i-Pr | 2-pyridyl | |
| 220 | 2,4-$F_2$ | i-Pr | 5-chloro-2-pyridyl | |
| 221 | 2,3-$Cl_2$ | i-Pr | 4-fluorophenyl | mp 107–108° C. |
| 222 | 2,3-$Cl_2$ | i-Pr | 2,4-difluorophenyl | mp 103–104° C. |

TABLE 1a-continued
General formula (Ia)
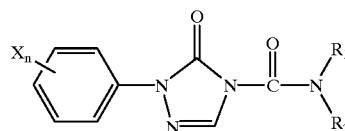
| Compound No. | $X_n$ | $R_1$ | $R_2$ | Physical data |
|---|---|---|---|---|
| 223 | 2,4-Cl$_2$ | n-Pr | 2,4-F$_2$-C$_6$H$_3$ | |
| 224 | 2,4-Cl$_2$ | n-Bu | 2,4-F$_2$-C$_6$H$_3$ | |
| 225 | 2,4-Cl$_2$ | i-Bu | 2,4-F$_2$-C$_6$H$_3$ | |
| 226 | 2,4-Cl$_2$ | sec-Bu | 2,4-F$_2$-C$_6$H$_3$ | |
| 227 | 2,4-Cl$_2$ | cyclopentyl | 2,4-F$_2$-C$_6$H$_3$ | |
| 228 | 2,4-Cl$_2$ | —CH$_2$CH=CH$_2$ | 2,4-F$_2$-C$_6$H$_3$ | |
| 229 | 2,4-Cl$_2$ | —CH$_2$C≡CH | 2,4-F$_2$-C$_6$H$_3$ | |
| 230 | 2,4-Cl$_2$ | i-Pr | C$_6$H$_5$ | |
| 231 | 2,4-Cl$_2$ | i-Pr | 2,4-F$_2$-C$_6$H$_3$ | mp 129–131° C. |

TABLE 1a-continued

General formula (Ia)

| Compound No. | Xₙ | R₁ | R₂ | Physical data |
|---|---|---|---|---|
| 232 | 2,4-Cl₂ | i-Pr | 2-F-phenyl | |
| 233 | 2,4-Cl₂ | i-Pr | 3-F-phenyl | |
| 234 | 2,4-Cl₂ | i-Pr | 4-F-phenyl | mp 170–172° C. |
| 235 | 2,4-Cl₂ | i-Pr | 2-Cl-phenyl | |
| 236 | 2,4-Cl₂ | i-Pr | 3-Cl-phenyl | |
| 237 | 2,4-Cl₂ | i-Pr | 4-Cl-phenyl | |
| 238 | 2,4-Cl₂ | i-Pr | 2,4-Cl₂-phenyl | |
| 239 | 2,4-Cl₂ | i-Pr | 2-Cl-4-F-phenyl | |
| 240 | 2,4-Cl₂ | i-Pr | 2-F-4-Cl-phenyl | |

TABLE 1a-continued
General formula (Ia)
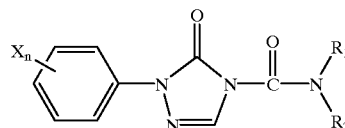
| Compound No. | $X_n$ | $R_1$ | $R_2$ | Physical data |
|---|---|---|---|---|
| 241 | 2,4-Cl$_2$ | i-Pr | 2,3,4-trifluorophenyl | |
| 242 | 2,4-Cl$_2$ | i-Pr | 2,4,5-trifluorophenyl | |
| 243 | 2,4-Cl$_2$ | i-Pr | 2-methylphenyl | |
| 244 | 2,4-Cl$_2$ | i-Pr | 3-methylphenyl | |
| 245 | 2,4-Cl$_2$ | i-Pr | 4-methylphenyl | |
| 246 | 2,4-Cl$_2$ | i-Pr | 4-methoxyphenyl | |
| 247 | 2,4-Cl$_2$ | i-Pr | 4-OCF$_3$-phenyl | |
| 248 | 2,4-Cl$_2$ | i-Pr | 4-CF$_3$-phenyl | |
| 249 | 2,4-Cl$_2$ | i-Pr | 4-CN-phenyl | |
| 250 | 2,4-Cl$_2$ | i-Pr | 3,4-dichlorophenyl | |

TABLE 1a-continued
General formula (Ia)
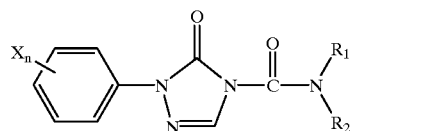
| Compound No. | $X_n$ | $R_1$ | $R_2$ | Physical data |
|---|---|---|---|---|
| 251 | 2,4-Cl$_2$ | i-Pr | 4-Br-C$_6$H$_4$ | |
| 252 | 2,4-Cl$_2$ | i-Pr | 4-I-C$_6$H$_4$ | |
| 253 | 2,4-Cl$_2$ | i-Pr | 2,5-Me$_2$-C$_6$H$_3$ | |
| 254 | 2,4-Cl$_2$ | i-Pr | 4-Et-C$_6$H$_4$ | |
| 255 | 2,4-Cl$_2$ | i-Pr | 2-Me-4-Cl-C$_6$H$_3$ | |
| 256 | 2,4-Cl$_2$ | i-Pr | 2-CF$_3$-4-Cl-C$_6$H$_3$ | |
| 257 | 2,4-Cl$_2$ | i-Pr | 4-OCHF$_2$-C$_6$H$_4$ | |
| 258 | 2,4-Cl$_2$ | cyclopropyl | C$_6$H$_5$ | |
| 259 | 2,4-Cl$_2$ | cyclopropyl | 4-Cl-C$_6$H$_4$ | |
| 260 | 2,4-Cl$_2$ | cyclopropyl | 2,4-F$_2$-C$_6$H$_3$ | |
| 261 | 2,4-Cl$_2$ | Et | Et | |

TABLE 1a-continued
General formula (Ia)
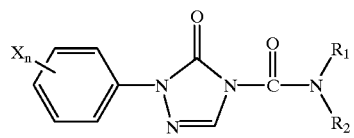
| Compound No. | $X_n$ | $R_1$ | $R_2$ | Physical data |
|---|---|---|---|---|
| 262 | 2,4-$Cl_2$ | Et | cyclohexyl | |
| 263 | 2,4-$Cl_2$ | —$CH_2CH=CH_2$ | Et | |
| 264 | 2,4-$Cl_2$ | —$CH_2C\equiv CH$ | Et | |
| 265 | 2,4-$Cl_2$ | —$CH_2CH=CH_2$ | cyclohexyl | |
| 266 | 2,4-$Cl_2$ | —$CH_2C\equiv CH$ | cyclohexyl | |
| 267 | 2,4-$Cl_2$ | i-Pr | —$CH_2$-phenyl | |
| 268 | 2,4-$Cl_2$ | i-Pr | —$CH_2$-(4-F-phenyl) | |
| 269 | 2,5-$Cl_2$ | i-Pr | 4-F-phenyl | mp 163–164° C. |
| 270 | 2,5-$Cl_2$ | i-Pr | 2,4-F$_2$-phenyl | mp 149–150° C. |
| 271 | 2,6-$Cl_2$ | Me | 2,4-F$_2$-phenyl | |
| 272 | 2,6-$Cl_2$ | Et | 2,4-F$_2$-phenyl | |
| 273 | 2,6-$Cl_2$ | n-Pr | 2,4-F$_2$-phenyl | |

TABLE 1a-continued
General formula (Ia)
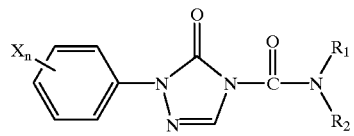
| Compound No. | $X_n$ | $R_1$ | $R_2$ | Physical data |
|---|---|---|---|---|
| 274 | 2,6-Cl$_2$ | n-Bu | 2,4-F$_2$-C$_6$H$_3$ | |
| 275 | 2,6-Cl$_2$ | i-Bu | 2,4-F$_2$-C$_6$H$_3$ | |
| 276 | 2,6-Cl$_2$ | sec-Bu | 2,4-F$_2$-C$_6$H$_3$ | |
| 277 | 2,6-Cl$_2$ | cyclopentyl | 2,4-F$_2$-C$_6$H$_3$ | |
| 278 | 2,6-Cl$_2$ | —CH$_2$CH=CH$_2$ | 2,4-F$_2$-C$_6$H$_3$ | |
| 279 | 2,6-Cl$_2$ | —CH$_2$C≡CH | 2,4-F$_2$-C$_6$H$_3$ | |
| 280 | 2.6-Cl$_2$ | i-Pr | C$_6$H$_5$ | |
| 281 | 2,6-Cl$_2$ | i-Pr | 2,4-F$_2$-C$_6$H$_3$ | mp 129–131° C. |
| 282 | 2,6-Cl$_2$ | i-Pr | 2-F-C$_6$H$_4$ | |

TABLE 1a-continued

General formula (Ia)

| Compound No. | $X_n$ | $R_1$ | $R_2$ | Physical data |
|---|---|---|---|---|
| 283 | 2,6-Cl$_2$ | i-Pr | 3-F-phenyl | |
| 284 | 2,6-Cl$_2$ | i-Pr | 4-F-phenyl | mp 223–225° C. |
| 285 | 2,6-Cl$_2$ | i-Pr | 2-Cl-phenyl | |
| 286 | 2,6-Cl$_2$ | i-Pr | 3-Cl-phenyl | |
| 287 | 2,6-Cl$_2$ | i-Pr | 4-Cl-phenyl | |
| 288 | 2,6-Cl$_2$ | i-Pr | 2,4-Cl$_2$-phenyl | |
| 289 | 2,6-Cl$_2$ | i-Pr | 2-Cl-4-F-phenyl | |
| 290 | 2,6-Cl$_2$ | i-Pr | 2-F-4-Cl-phenyl | |
| 291 | 2,6-Cl$_2$ | i-Pr | 2,3,4-F$_3$-phenyl | |

TABLE 1a-continued
General formula (Ia)
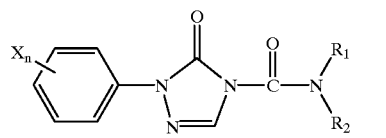
| Compound No. | X_n | R_1 | R_2 | Physical data |
|---|---|---|---|---|
| 292 | 2,6-Cl$_2$ | i-Pr | 2,4,5-trifluorophenyl | |
| 293 | 2,6-Cl$_2$ | i-Pr | 2-methylphenyl | |
| 294 | 2,6-Cl$_2$ | i-Pr | 3-methylphenyl | |
| 295 | 2,6-Cl$_2$ | i-Pr | 4-methylphenyl | |
| 296 | 2,6-Cl$_2$ | i-Pr | 4-OMe-phenyl | |
| 297 | 2,6-Cl$_2$ | i-Pr | 4-OCF$_3$-phenyl | |
| 298 | 2,6-Cl$_2$ | i-Pr | 4-CF$_3$-phenyl | |
| 299 | 2,6-Cl$_2$ | i-Pr | 4-CN-phenyl | |
| 300 | 2,6-Cl$_2$ | i-Pr | 3,4-dichlorophenyl | |
| 301 | 2,6-Cl$_2$ | i-Pr | 4-Br-phenyl | |

TABLE 1a-continued

General formula (Ia)

| Compound No. | $X_n$ | $R_1$ | $R_2$ | Physical data |
|---|---|---|---|---|
| 302 | 2,6-Cl$_2$ | i-Pr | 4-I-C$_6$H$_4$ | |
| 303 | 2,6-Cl$_2$ | i-Pr | 2,4,5-tri-Me-C$_6$H$_2$ | |
| 304 | 2,6-Cl$_2$ | i-Pr | 4-Et-C$_6$H$_4$ | |
| 305 | 2,6-Cl$_2$ | i-Pr | 2-Me-4-Cl-C$_6$H$_3$ | |
| 306 | 2,6-Cl$_2$ | i-Pr | 2-CF$_3$-4-Cl-C$_6$H$_3$ | |
| 307 | 2,6-Cl$_2$ | i-Pr | 4-OCHF$_2$-C$_6$H$_4$ | |
| 308 | 2,6-Cl$_2$ | cyclopropyl | C$_6$H$_5$ | |
| 309 | 2,6-Cl$_2$ | cyclopropyl | 4-Cl-C$_6$H$_4$ | |
| 310 | 2,6-Cl$_2$ | cyclopropyl | 2,4-F$_2$-C$_6$H$_3$ | |
| 311 | 2,6-Cl$_2$ | Et | Et | |
| 312 | 2,6-Cl$_2$ | Et | cyclohexyl | |
| 313 | 2,6-Cl$_2$ | —CH$_2$CH=CH$_2$ | Et | |
| 314 | 2,6-Cl$_2$ | —CH$_2$C≡CH | Et | |

TABLE 1a-continued

General formula (Ia)

| Compound No. | $X_n$ | $R_1$ | $R_2$ | Physical data |
|---|---|---|---|---|
| 315 | 2,6-Cl$_2$ | —CH$_2$CH=CH$_2$ | cyclohexyl | |
| 316 | 2,6-Cl$_2$ | —CH$_2$C≡CH | cyclohexyl | |
| 317 | 3,5-Cl$_2$ | i-Pr | 4-F-phenyl | mp 179–181° C. |
| 318 | 3,5-Cl$_2$ | i-Pr | 2,4-F$_2$-phenyl | mp 124–126° C. |
| 319 | 3,4-Cl$_2$ | i-Pr | 4-F-phenyl | mp 146–147° C. |
| 320 | 3,4-Cl$_2$ | i-Pr | 2,4-F$_2$-phenyl | mp 176–177° C. |
| 321 | 2-F, 4-Cl | i-Pr | 4-F-phenyl | mp 171–172° C. |
| 322 | 2-F, 4-Cl | i-Pr | 2,4-F$_2$-phenyl | mp 199–200° C. |
| 323 | 2-Cl, 4-F | i-Pr | 4-F-phenyl | mp 121–122° C. |
| 324 | 2-Cl, 4-F | i-Pr | 2,4-F$_2$-phenyl | mp 122–124° C. |

TABLE 1a-continued
General formula (Ia)
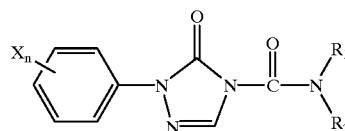
| Compound No. | X_n | R_1 | R_2 | Physical data |
|---|---|---|---|---|
| 325 | 2-Me | i-Bu | 2,4-difluorophenyl | |
| 326 | 2-Me | sec-Bu | 2,4-difluorophenyl | |
| 327 | 2-Me | cyclopentyl | 2,4-difluorophenyl | |
| 328 | 2-Me | —CH$_2$CH=CH$_2$ | 2,4-difluorophenyl | |
| 329 | 2-Me | —CH$_2$C≡CH | 2,4-difluorophenyl | |
| 330 | 2-Me | i-Pr | phenyl | |
| 331 | 2-Me | i-Pr | 2,4-difluorophenyl | mp 106–107° C. |
| 332 | 2-Me | i-Pr | 2-fluorophenyl | mp 96–98° C. |
| 333 | 2-Me | i-Pr | 3-fluorophenyl | |

TABLE 1a-continued
General formula (Ia)
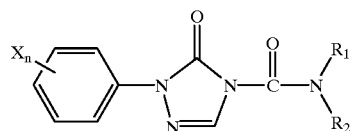
| Compound No. | $X_n$ | $R_1$ | $R_2$ | Physical data |
|---|---|---|---|---|
| 334 | 2-Me | i-Pr | 4-F-C6H4-CH2- | mp 94–95° C. |
| 335 | 2-Me | i-Pr | 2-Cl-C6H4-CH2- | |
| 336 | 2-Me | i-Pr | 3-Cl-C6H4-CH2- | |
| 337 | 2-Me | i-Pr | 4-Cl-C6H4-CH2- | |
| 338 | 2-Me | i-Pr | 2,4-Cl2-C6H3-CH2- | |
| 339 | 2-Me | i-Pr | 2-Cl-4-F-C6H3-CH2- | |
| 340 | 2-Me | i-Pr | 2-F-4-Cl-C6H3-CH2- | |
| 341 | 2-Me | i-Pr | 2,3,4-F3-C6H2-CH2- | |
| 342 | 2-Me | i-Pr | 2,4,5-F3-C6H2-CH2- | |

TABLE 1a-continued
General formula (Ia)
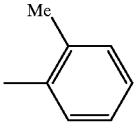
| Compound No. | X_n | R_1 | R_2 | Physical data |
|---|---|---|---|---|
| 343 | 2-Me | i-Pr | 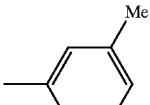 2-Me-phenyl | |
| 344 | 2-Me | i-Pr | 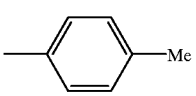 3-Me-phenyl | |
| 345 | 2-Me | i-Pr | 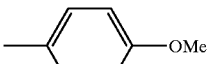 4-Me-phenyl | |
| 346 | 2-Me | i-Pr | 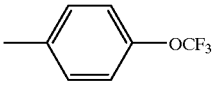 4-OMe-phenyl | |
| 347 | 2-Me | i-Pr | 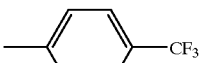 4-OCF_3-phenyl | |
| 348 | 2-Me | i-Pr | 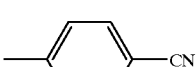 4-CF_3-phenyl | |
| 349 | 2-Me | i-Pr | 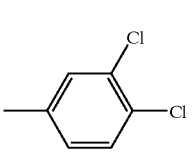 4-CN-phenyl | |
| 350 | 2-Me | i-Pr | 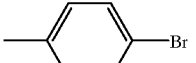 3,4-diCl-phenyl | |
| 351 | 2-Me | i-Pr | 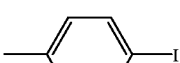 4-Br-phenyl | |
| 352 | 2-Me | i-Pr | 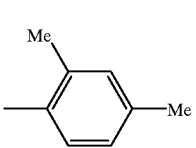 4-I-phenyl | |
| 353 | 2-Me | i-Pr | 2,5-diMe-phenyl | |

TABLE 1a-continued
General formula (Ia)
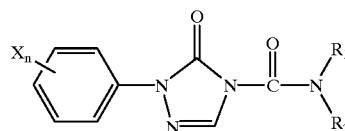
| Compound No. | $X_n$ | $R_1$ | $R_2$ | Physical data |
|---|---|---|---|---|
| 354 | 2-Me | i-Pr | 4-Et-C6H4 | |
| 355 | 2-Me | i-Pr | 2-Me-5-Cl-C6H3 | |
| 356 | 2-Me | i-Pr | 2-CF3-5-Cl-C6H3 | |
| 357 | 2-Me | i-Pr | 4-OCHF2-C6H4 | |
| 358 | 2-Me | cyclopropyl | C6H5 | |
| 359 | 2-Me | cyclopropyl | 4-Cl-C6H4 | |
| 360 | 2-Me | n-Pr | cyclopentyl | $n_D^{18}$ 1.5511 |
| 361 | 2-Me | Et | Et | |
| 362 | 2-Me | i-Pr | cyclohexyl | mp 116–117° C. |
| 363 | 2-Me | —CH2CH=CH2 | Et | |
| 364 | 2-Me | —CH2C≡CH | Et | |
| 365 | 2-Me | —CH2CH=CH2 | cyclohexyl | mp 72–74° C. |
| 366 | 2-Me | —CH2C≡CH | cyclohexyl | |

TABLE 1a-continued
General formula (Ia)
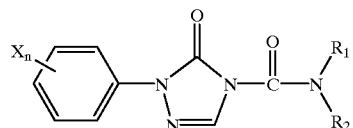
| Compound No. | $X_n$ | $R_1$ | $R_2$ | Physical data |
|---|---|---|---|---|
| 367 | 2-Me | i-Pr | —CH$_2$—C$_6$H$_5$ | |
| 368 | 2-Me | i-Pr | —CH$_2$—(4-F-C$_6$H$_4$) | |
| 369 | 2-Me | i-Pr | 2-pyridyl-methyl | |
| 370 | 2-Me | i-Pr | (5-Cl-2-pyridyl)-methyl | |
| 371 | 3-Me | Me | 2,4-F$_2$-C$_6$H$_3$ | |
| 372 | 3-Me | Et | 2,4-F$_2$-C$_6$H$_3$ | |
| 373 | 3-Me | n-Pr | 2,4-F$_2$-C$_6$H$_3$ | |
| 374 | 3-Me | n-Bu | 2,4-F$_2$-C$_6$H$_3$ | |
| 375 | 3-Me | i-Bu | 2,4-F$_2$-C$_6$H$_3$ | |
| 376 | 3-Me | sec-Bu | 2,4-F$_2$-C$_6$H$_3$ | |

TABLE 1a-continued
General formula (Ia)
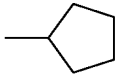
| Compound No. | $X_n$ | $R_1$ | $R_2$ | Physical data |
|---|---|---|---|---|
| 377 | 3-Me | 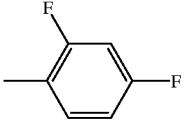 | 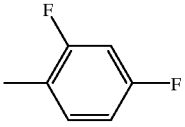 | |
| 378 | 3-Me | —CH$_2$CH=CH$_2$ | 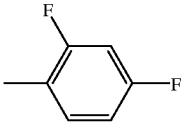 | |
| 379 | 3-Me | —CH$_2$C≡CH | 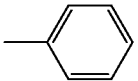 | |
| 380 | 3-Me | i-Pr | 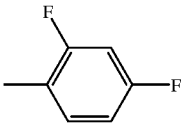 | |
| 381 | 3-Me | i-Pr | 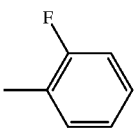 | mp 133–134° C. |
| 382 | 3-Me | i-Pr | 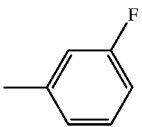 | |
| 383 | 3-Me | i-Pr |  | |
| 384 | 3-Me | i-Pr | 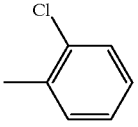 | mp 150–151° C. |
| 385 | 3-Me | i-Pr |  | |

TABLE 1a-continued
General formula (Ia)
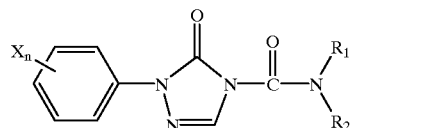
| Compound No. | $X_n$ | $R_1$ | $R_2$ | Physical data |
|---|---|---|---|---|
| 386 | 3-Me | i-Pr | 3-chlorophenyl | |
| 387 | 3-Me | i-Pr | 4-chlorophenyl | |
| 388 | 3-Me | i-Pr | 2,4-dichlorophenyl | |
| 389 | 3-Me | i-Pr | 2-chloro-4-fluorophenyl | |
| 390 | 3-Me | i-Pr | 2-fluoro-4-chlorophenyl | |
| 391 | 3-Me | i-Pr | 2,3,4-trifluorophenyl | |
| 392 | 3-Me | i-Pr | 2,4,5-trifluorophenyl | |
| 393 | 3-Me | i-Pr | 2-methylphenyl | |
| 394 | 3-Me | i-Pr | 3-methylphenyl | |

TABLE 1a-continued

General formula (Ia)

| Compound No. | $X_n$ | $R_1$ | $R_2$ | Physical data |
|---|---|---|---|---|
| 395 | 3-Me | i-Pr | 4-Me-C6H4 | |
| 396 | 3-Me | i-Pr | 4-OMe-C6H4 | |
| 397 | 3-Me | i-Pr | 4-OCF3-C6H4 | |
| 398 | 3-Me | i-Pr | 4-CF3-C6H4 | |
| 399 | 3-Me | i-Pr | 4-CN-C6H4 | |
| 400 | 3-Me | i-Pr | 3,4-Cl2-C6H3 | |
| 401 | 3-Me | i-Pr | 4-Br-C6H4 | |
| 402 | 3-Me | i-Pr | 4-I-C6H4 | |
| 403 | 3-Me | i-Pr | 2,4-Me2-C6H3 | |
| 404 | 3-Me | i-Pr | 4-Et-C6H4 | |
| 405 | 3-Me | i-Pr | 2-Me-4-Cl-C6H3 | |

TABLE 1a-continued
General formula (Ia)
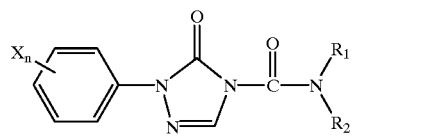
| Compound No. | $X_n$ | $R_1$ | $R_2$ | Physical data |
|---|---|---|---|---|
| 406 | 3-Me | i-Pr | 2-CF$_3$-4-Cl-phenyl | |
| 407 | 3-Me | i-Pr | 4-OCHF$_2$-phenyl | |
| 408 | 3-Me | cyclopropyl | phenyl | |
| 409 | 3-Me | cyclopropyl | 4-Cl-phenyl | |
| 410 | 3-Me | cyclopropyl | 2,4-diF-phenyl | |
| 411 | 3-Me | Et | Et | |
| 412 | 3-Me | Et | cyclohexyl | |
| 413 | 3-Me | —CH$_2$CH=CH$_2$ | Et | |
| 414 | 3-Me | —CH$_2$C≡CH | Et | |
| 415 | 3-Me | —CH$_2$CH=CH$_2$ | cyclohexyl | |
| 416 | 3-Me | —CH$_2$C≡CH | cyclohexyl | |
| 417 | 3-Me | i-Pr | —CH$_2$-phenyl | |
| 418 | 3-Me | i-Pr | —CH$_2$-(4-F-phenyl) | |

TABLE 1a-continued
General formula (Ia)
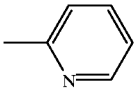
| Compound No. | $X_n$ | $R_1$ | $R_2$ | Physical data |
|---|---|---|---|---|
| 419 | 3-Me | i-Pr | 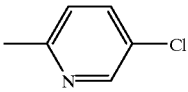 | |
| 420 | 3-Me | i-Pr | 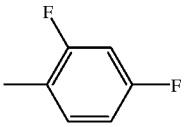 | |
| 421 | 4-Me | Me | 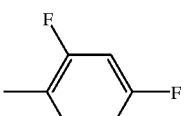 | |
| 422 | 4-Me | Et | 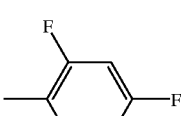 | |
| 423 | 4-Me | n-Pr | 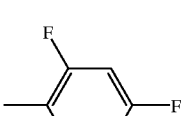 | |
| 424 | 4-Me | n-Bu | 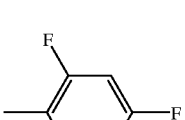 | |
| 425 | 4-Me | i-Bu | 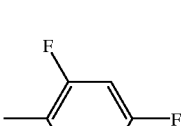 | |
| 426 | 4-Me | sec-Bu | 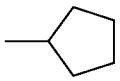 | |
| 427 | 4-Me | 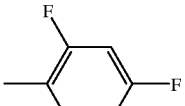 | | |

TABLE 1a-continued
General formula (Ia)
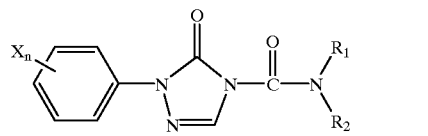
| Compound No. | $X_n$ | $R_1$ | $R_2$ | Physical data |
|---|---|---|---|---|
| 428 | 4-Me | —CH$_2$CH=CH$_2$ | 2,4-difluorophenyl | |
| 429 | 4-Me | —CH$_2$C≡CH | 2,4-difluorophenyl | |
| 430 | 4-Me | i-Pr | phenyl | |
| 431 | 4-Me | i-Pr | 2,4-difluorophenyl | mp 164–165° C. |
| 432 | 4-Me | i-Pr | 2-fluorophenyl | |
| 433 | 4-Me | i-Pr | 3-fluorophenyl | |
| 434 | 4-Me | i-Pr | 4-fluorophenyl | mp 153–155° C. |
| 435 | 4-Me | i-Pr | 2-chlorophenyl | |
| 436 | 4-Me | i-Pr | 3-chlorophenyl | |
| 437 | 4-Me | i-Pr | 4-chlorophenyl | |

TABLE 1a-continued
General formula (Ia)
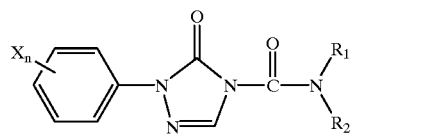
| Compound No. | $X_n$ | $R_1$ | $R_2$ | Physical data |
|---|---|---|---|---|
| 438 | 4-Me | i-Pr | 2,4-dichlorophenyl | |
| 439 | 4-Me | i-Pr | 2-chloro-4-fluorophenyl | |
| 440 | 4-Me | i-Pr | 2-fluoro-4-chlorophenyl | |
| 441 | 4-Me | i-Pr | 2,3,4-trifluorophenyl | |
| 442 | 4-Me | i-Pr | 2,4,5-trifluorophenyl | |
| 443 | 4-Me | i-Pr | 2-methylphenyl | |
| 444 | 4-Me | i-Pr | 3-methylphenyl | |
| 445 | 4-Me | i-Pr | 4-methylphenyl | |
| 446 | 4-Me | i-Pr | 4-methoxyphenyl | |

TABLE 1a-continued
General formula (Ia)
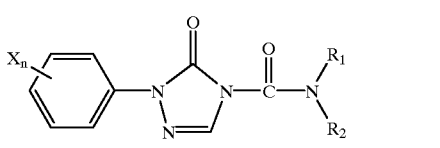
| Compound No. | X$_n$ | R$_1$ | R$_2$ | Physical data |
|---|---|---|---|---|
| 447 | 4-Me | i-Pr | 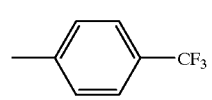 | |
| 448 | 4-Me | i-Pr | 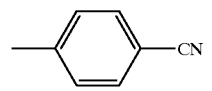 | |
| 449 | 4-Me | i-Pr | 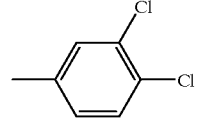 | |
| 450 | 4-Me | i-Pr | 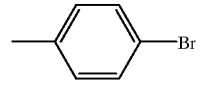 | |
| 451 | 4-Me | i-Pr | 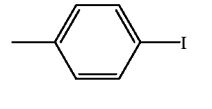 | |
| 452 | 4-Me | i-Pr | 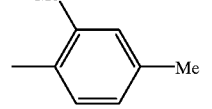 | |
| 453 | 4-Me | i-Pr | 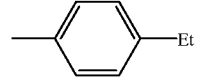 | |
| 454 | 4-Me | i-Pr | 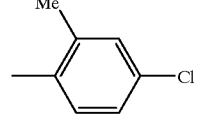 | |
| 455 | 4-Me | i-Pr | 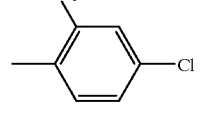 | |
| 456 | 4-Me | i-Pr | 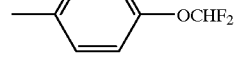 | |
| 457 | 4-Me | i-Pr |  | |

TABLE 1a-continued
General formula (Ia)
| Compound No. | $X_n$ | $R_1$ | $R_2$ | Physical data |
|---|---|---|---|---|
| 458 | 4-Me | cyclopropyl | phenyl | |
| 459 | 4-Me | cyclopropyl | 4-Cl-phenyl | |
| 460 | 4-Me | cyclopropyl | 2,4-diF-phenyl | |
| 461 | 4-Me | Et | Et | |
| 462 | 4-Me | Et | cyclohexyl | |
| 463 | 4-Me | —CH$_2$CH=CH$_2$ | Et | |
| 464 | 4-Me | —CH$_2$C≡CH | Et | |
| 465 | 4-Me | —CH$_2$CH=CH$_2$ | cyclohexyl | |
| 466 | 4-Me | —CH$_2$C≡CH | cyclohexyl | |
| 467 | 4-Me | i-Pr | —CH$_2$-phenyl | |
| 468 | 4-Me | i-Pr | —CH$_2$-(4-F-phenyl) | |
| 469 | 4-Me | i-Pr | 2-pyridyl | |
| 470 | 4-Me | i-Pr | 5-Cl-2-pyridyl | |

TABLE 1a-continued
General formula (Ia)
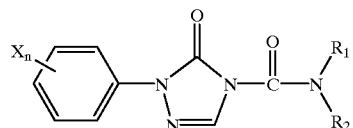
| Compound No. | X<sub>n</sub> | R₁ | R₂ | Physical data |
|---|---|---|---|---|
| 471 | 2-Et | Me | 2,4-difluorophenyl | |
| 472 | 2-Et | Et | 2,4-difluorophenyl | |
| 473 | 2-Et | n-Pr | 2,4-difluorophenyl | |
| 474 | 2-Et | n-Bu | 2,4-difluorophenyl | |
| 475 | 2-Et | i-Bu | 2,4-difluorophenyl | |
| 476 | 2-Et | sec-Bu | 2,4-difluorophenyl | |
| 477 | 2-Et | cyclopentyl | 2,4-difluorophenyl | |
| 478 | 2-Et | —CH₂CH=CH₂ | 2,4-difluorophenyl | |
| 479 | 2-Et | —CH₂C≡CH | 2,4-difluorophenyl | |

TABLE 1a-continued
General formula (Ia)
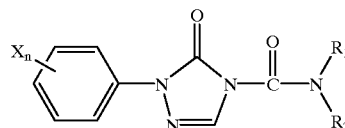
| Compound No. | $X_n$ | $R_1$ | $R_2$ | Physical data |
|---|---|---|---|---|
| 480 | 2-Et | i-Pr | phenyl | |
| 481 | 2-Et | i-Pr | 2,4-difluorophenyl | mp 66–68° C. |
| 482 | 2-Et | i-Pr | 2-fluorophenyl | |
| 483 | 2-Et | i-Pr | 3-fluorophenyl | |
| 484 | 2-Et | i-Pr | 4-fluorophenyl | $n_D^{18}$ 1.5483 |
| 485 | 2-Et | i-Pr | 2-chlorophenyl | |
| 486 | 2-Et | i-Pr | 3-chlorophenyl | |
| 487 | 2-Et | i-Pr | 4-chlorophenyl | |
| 488 | 2-Et | i-Pr | 2,4-dichlorophenyl | |
| 489 | 2-Et | i-Pr | 2-chloro-4-fluorophenyl | |

TABLE 1a-continued
General formula (Ia)
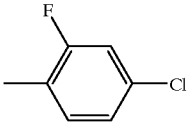
| Compound No. | $X_n$ | $R_1$ | $R_2$ | Physical data |
|---|---|---|---|---|
| 490 | 2-Et | i-Pr | 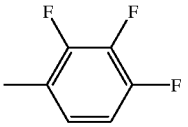 | |
| 491 | 2-Et | i-Pr | 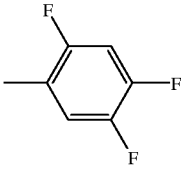 | |
| 492 | 2-Et | i-Pr | 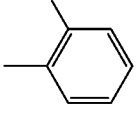 | |
| 493 | 2-Et | i-Pr | 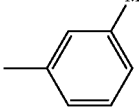 | |
| 494 | 2-Et | i-Pr | 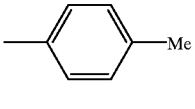 | |
| 495 | 2-Et | i-Pr | 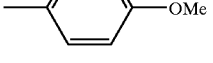 | |
| 496 | 2-Et | i-Pr | 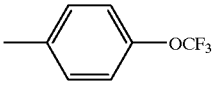 | |
| 497 | 2-Et | i-Pr | 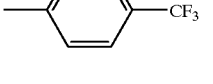 | |
| 498 | 2-Et | i-Pr | 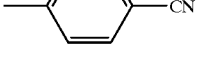 | |
| 499 | 2-Et | i-Pr | | |

TABLE 1a-continued
General formula (Ia)
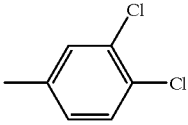
| Compound No. | $X_n$ | $R_1$ | $R_2$ | Physical data |
|---|---|---|---|---|
| 500 | 2-Et | i-Pr | 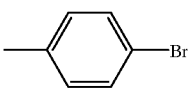 3,4-di-Cl-phenyl | |
| 501 | 2-Et | i-Pr |  4-Br-phenyl | |
| 502 | 2-Et | i-Pr | 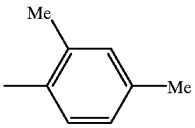 4-I-phenyl | |
| 503 | 2-Et | i-Pr | 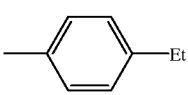 2,4-di-Me-phenyl | |
| 504 | 2-Et | i-Pr | 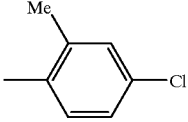 4-Et-phenyl | |
| 505 | 2-Et | i-Pr | 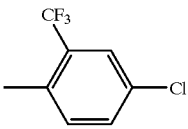 2-Me-4-Cl-phenyl | |
| 506 | 2-Et | i-Pr | 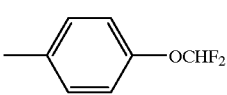 2-CF3-4-Cl-phenyl | |
| 507 | 2-Et | i-Pr |  4-OCHF2-phenyl | |
| 508 | 2-Et | cyclopropyl | 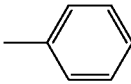 phenyl | |
| 509 | 2-Et | cyclopropyl |  4-Cl-phenyl | |

TABLE 1a-continued

General formula (Ia)

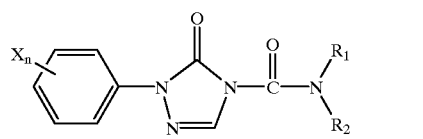

| Compound No. | $X_n$ | $R_1$ | $R_2$ | Physical data |
|---|---|---|---|---|
| 510 | 2-Et | cyclopropyl | 2,4-difluorophenyl | |
| 511 | 2-Et | Et | Et | |
| 512 | 2-Et | Et | cyclohexyl | |
| 513 | 2-Et | —CH$_2$CH=CH$_2$ | Et | |
| 514 | 2-Et | —CH$_2$C≡CH | Et | |
| 515 | 2-Et | —CH$_2$CH=CH$_2$ | cyclohexyl | |
| 516 | 2-Et | —CH$_2$C≡CH | cyclohexyl | |
| 517 | 2-n-Pr | i-Pr | 4-fluorophenyl | mp 100–101° C. |
| 518 | 2-n-Pr | i-Pr | 2,4-difluorophenyl | mp 57–59° C. |
| 519 | 2-i-Pr | i-Pr | 4-fluorophenyl | mp 139–140° C. |
| 520 | 2-i-Pr | i-Pr | 2,4-difluorophenyl | mp 92–93° C. |
| 521 | 2-MeO | i-Pr | 4-fluorophenyl | mp 107–109° C. |
| 522 | 2-MeO | i-Pr | 2,4-difluorophenyl | mp 113–115° C. |

TABLE 1a-continued
General formula (Ia)
| Compound No. | $X_n$ | $R_1$ | $R_2$ | Physical data |
|---|---|---|---|---|
| 523 | 3-MeO | i-Pr | 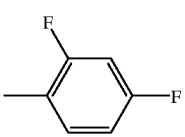 | |
| 524 | 3-MeO | i-Pr | 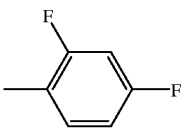 | mp 150–151° C. |
| 525 | 4-MeO | i-Bu | 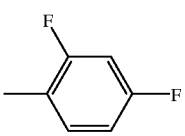 | |
| 526 | 4-MeO | sec-Bu | 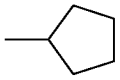 | |
| 527 | 4-MeO | 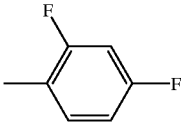 | 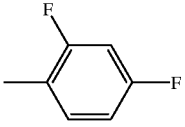 | |
| 528 | 4-MeO | —CH$_2$CH=CH$_2$ | 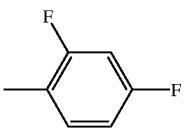 | |
| 529 | 4-MeO | —CH$_2$C≡CH | 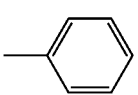 | |
| 530 | 4-MeO | i-Pr | 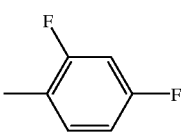 | |
| 531 | 4-MeO | i-Pr | | mp 148–149° C. |

TABLE 1a-continued
General formula (Ia)
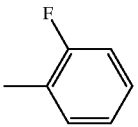
| Compound No. | $X_n$ | $R_1$ | $R_2$ | Physical data |
|---|---|---|---|---|
| 532 | 4-MeO | i-Pr | 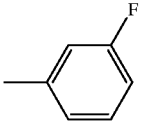 | |
| 533 | 4-MeO | i-Pr |  | |
| 534 | 4-MeO | i-Pr | 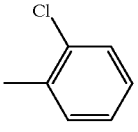 | mp 125–126° C. |
| 535 | 4-MeO | i-Pr | 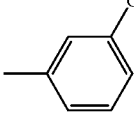 | |
| 536 | 4-MeO | i-Pr |  | |
| 537 | 4-MeO | i-Pr | 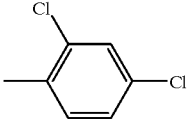 | |
| 538 | 4-MeO | i-Pr | 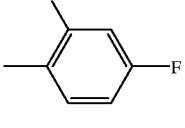 | |
| 539 | 4-MeO | i-Pr | 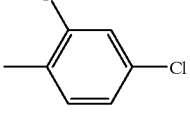 | |
| 540 | 4-MeO | i-Pr | | |

TABLE 1a-continued
General formula (Ia)
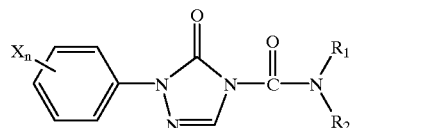
| Compound No. | X_n | R_1 | R_2 | Physical data |
|---|---|---|---|---|
| 541 | 4-MeO | i-Pr | 2,3,4-trifluorophenyl | |
| 542 | 4-MeO | i-Pr | 2,4,5-trifluorophenyl | |
| 543 | 4-MeO | i-Pr | 2-methylphenyl | |
| 544 | 4-MeO | i-Pr | 3-methylphenyl | |
| 545 | 4-MeO | i-Pr | 4-methylphenyl | |
| 546 | 4-MeO | i-Pr | 4-OMe-phenyl | |
| 547 | 4-MeO | i-Pr | 4-OCF$_3$-phenyl | |
| 548 | 4-MeO | i-Pr | 4-CF$_3$-phenyl | |
| 549 | 4-MeO | i-Pr | 4-CN-phenyl | |
| 550 | 4-MeO | i-Pr | 3,4-dichlorophenyl | |

TABLE 1a-continued
General formula (Ia)
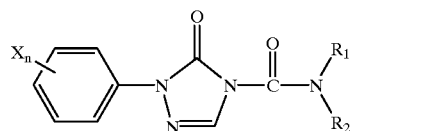
| Compound No. | X$_n$ | R$_1$ | R$_2$ | Physical data |
|---|---|---|---|---|
| 551 | 4-MeO | i-Pr | 4-Br-C$_6$H$_4$ | |
| 552 | 4-MeO | i-Pr | 4-I-C$_6$H$_4$ | |
| 553 | 4-MeO | i-Pr | 2,4-Me$_2$-C$_6$H$_3$ | |
| 554 | 4-MeO | i-Pr | 4-Et-C$_6$H$_4$ | |
| 555 | 4-MeO | i-Pr | 2-Me-4-Cl-C$_6$H$_3$ | |
| 556 | 4-MeO | i-Pr | 2-CF$_3$-4-Cl-C$_6$H$_3$ | |
| 557 | 4-MeO | i-Pr | 4-OCHF$_2$-C$_6$H$_4$ | |
| 558 | 4-MeO | c-Pr | C$_6$H$_5$ | |
| 559 | 4-MeO | c-Pr | 4-Cl-C$_6$H$_4$ | |
| 560 | 4-MeO | c-Pr | 2,4-F$_2$-C$_6$H$_3$ | |
| 561 | 4-MeO | Et | Et | |

TABLE 1a-continued
General formula (Ia)
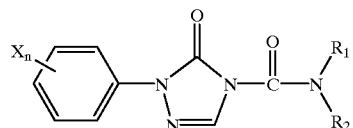
| Compound No. | $X_n$ | $R_1$ | $R_2$ | Physical data |
|---|---|---|---|---|
| 562 | 4-MeO | Et | cyclohexyl | |
| 563 | 4-MeO | —CH$_2$CH=CH$_2$ | Et | |
| 564 | 4-MeO | —CH$_2$C≡CH | Et | |
| 565 | 4-MeO | —CH$_2$CH=CH$_2$ | cyclohexyl | |
| 566 | 4-MeO | —CH$_2$C≡CH | cyclohexyl | |
| 567 | 4-MeO | i-Pr | —CH$_2$-phenyl | |
| 568 | 4-MeO | i-Pr | —CH$_2$-(4-F-phenyl) | |
| 569 | 3,5-(MeO)$_2$ | i-Pr | 4-F-phenyl | |
| 570 | 3,5-(MeO)$_2$ | i-Pr | 2,4-F$_2$-phenyl | mp 99–100° C. |
| 571 | 2-Cl, 6-Me | i-Pr | 4-F-phenyl | mp 204–205° C. |
| 572 | 2-Cl, 6-Me | i-Pr | 2,4-F$_2$-phenyl | mp 94–96° C. |
| 573 | 2-Cl, 6-Me | i-Pr | 4-Cl-phenyl | |
| 574 | 2-Cl, 6-Me | Et | cyclohexyl | |

TABLE 1a-continued
General formula (Ia)
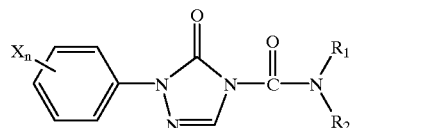
| Compound No. | $X_n$ | $R_1$ | $R_2$ | Physical data |
|---|---|---|---|---|
| 575 | 2-Cl, 6-Me | Et | Et | |
| 576 | 2,6-(Me)$_2$ | i-Pr | 4-F-C$_6$H$_4$ | mp 190–191° C. |
| 577 | 2,6-(Me)$_2$ | i-Pr | 2,4-F$_2$-C$_6$H$_3$ | mp 101–102° C. |
| 578 | 2,6-(Me)$_2$ | i-Pr | 4-Cl-C$_6$H$_4$ | |
| 579 | 2,6-(Me)$_2$ | Et | cyclohexyl | |
| 580 | 2,6-(Me)$_2$ | Et | Et | |
| 581 | 2,4-(Me)$_2$ | i-Pr | 4-F-C$_6$H$_4$ | mp 133–134° C. |
| 582 | 2,4-(Me)$_2$ | i-Pr | 2,4-F$_2$-C$_6$H$_3$ | mp 91–93° C. |
| 583 | 2,4-(Me)$_2$ | i-Pr | 4-Cl-C$_6$H$_4$ | |
| 584 | 2,4-(Me)$_2$ | Et | cyclohexyl | |
| 585 | 2,4-(Me)$_2$ | Et | Et | |
| 586 | 2,5-(Me)$_2$ | i-Pr | 4-F-C$_6$H$_4$ | mp 125–127° C. |
| 587 | 2,5-(Me)$_2$ | i-Pr | 2,4-F$_2$-C$_6$H$_3$ | mp 86–88° C. |

TABLE 1a-continued

General formula (Ia)

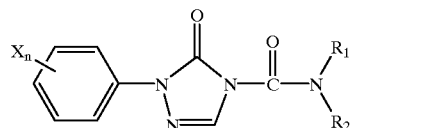

| Compound No. | $X_n$ | $R_1$ | $R_2$ | Physical data |
|---|---|---|---|---|
| 588 | 2,5-(Me)$_2$ | i-Pr | 4-Cl-C$_6$H$_4$-CH$_2$- | |
| 589 | 2,5-(Me)$_2$ | Et | cyclohexyl-CH$_2$- | |
| 590 | 2,5-(Me)$_2$ | Et | Et | |
| 591 | 2,3-(Me)$_2$ | i-Pr | 4-F-C$_6$H$_4$-CH$_2$- | mp 122–124° C. |
| 592 | 2,3-(Me)$_2$ | i-Pr | 2,4-F$_2$-C$_6$H$_3$-CH$_2$- | mp 109–110° C. |
| 593 | 2,3-(Me)$_2$ | i-Pr | 4-Cl-C$_6$H$_4$-CH$_2$- | |
| 594 | 2-Et, 6-Me | i-Pr | 4-F-C$_6$H$_4$-CH$_2$- | mp 115–117° C. |
| 595 | 2-Et, 6-Me | i-Pr | 2,4-F$_2$-C$_6$H$_3$-CH$_2$- | mp 97–99° C. |
| 596 | 2-CF$_3$ | i-Pr | 4-F-C$_6$H$_4$-CH$_2$- | mp 129–130° C. |
| 597 | 2-CF$_3$ | i-Pr | 2,4-F$_2$-C$_6$H$_3$-CH$_2$- | mp 106–107° C. |
| 598 | 2-CF$_3$ | i-Pr | 4-Cl-C$_6$H$_4$-CH$_2$- | |
| 599 | 3-CF$_3$ | i-Pr | 4-F-C$_6$H$_4$-CH$_2$- | mp 171–172° C. |

TABLE 1a-continued
General formula (Ia)
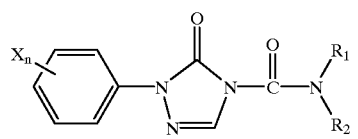
| Compound No. | $X_n$ | $R_1$ | $R_2$ | Physical data |
| --- | --- | --- | --- | --- |
| 600 | 3-$CF_3$ | i-Pr | 2,4-difluorophenyl | mp 188–189° C. |
| 601 | 4-$CF_3$ | i-Pr | 4-fluorophenyl | mp 161–162° C. |
| 602 | 4-$CF_3$ | i-Pr | 2,4-difluorophenyl | mp 192–193° C. |
| 603 | 4-$CF_3$ | i-Pr | 4-chlorophenyl | |
| 604 | 4-$CF_3$ | Et | cyclohexyl | |
| 605 | 4-$CF_3$ | Et | Et | |
| 606 | 2-$CHF_2O$ | i-Pr | 4-fluorophenyl | |
| 607 | 2-$CHF_2O$ | i-Pr | 2,4-difluorophenyl | |
| 608 | 2-$CHF_2O$ | i-Pr | 4-chlorophenyl | |
| 609 | 2-$CHF_2O$ | Et | cyclohexyl | |
| 610 | 2-$CHF_2O$ | Et | Et | |
| 611 | 2-$CF_3O$ | i-Pr | 4-fluorophenyl | mp 91–92° C. |

TABLE 1a-continued
General formula (Ia)
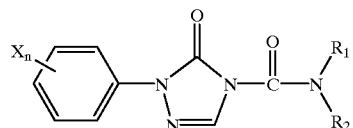
| Compound No. | $X_n$ | $R_1$ | $R_2$ | Physical data |
|---|---|---|---|---|
| 612 | 2-CF$_3$O | i-Pr | 2,4-difluorophenyl | mp 80–82° C. |
| 613 | 2-CF$_3$O | i-Pr | 4-chlorophenyl | |
| 614 | 2-CF$_3$O | Et | cyclohexyl | |
| 615 | 2-CF$_3$O | Et | Et | |
| 616 | 2,4,6-(Me)$_3$ | i-Pr | 4-fluorophenyl | |
| 617 | 2,4,6-(Me)$_3$ | i-Pr | 2,4-difluorophenyl | mp 141–143° C. |
| 618 | 2,4,6-(Me)$_3$ | i-Pr | 4-chlorophenyl | |
| 619 | 2,4,6-(Me)$_3$ | Et | cyclohexyl | |
| 620 | 2,4,6-(Me)$_3$ | Et | Et | |
| 621 | 2,4,6-Cl$_3$ | i-Pr | 2,4-difluorophenyl | mp 183–185° C. |
| 622 | 2,4,6-Cl$_3$ | i-Pr | 4-fluorophenyl | |
| 623 | 2-(phenoxy) | i-Pr | 2,4-difluorophenyl | mp 121–122° C. |

TABLE 1a-continued
General formula (Ia)
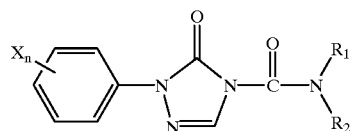
| Compound No. | X_n | R_1 | R_2 | Physical data |
|---|---|---|---|---|
| 624 | 2-(phenoxy) | i-Pr | 4-F-phenyl | mp 132–133° C. |
| 625 | 2-MeS | i-Pr | 2,4-F_2-phenyl | mp 112–114° C. |
| 626 | 2-MeS | i-Pr | 4-F-phenyl | mp 98–100° C. |
| 627 | 2-MeSO | i-Pr | 2,4-F_2-phenyl | mp 111–112° C. |
| 628 | 2-MeSO | i-Pr | 4-F-phenyl | |
| 629 | 2-MeSO_2 | i-Pr | 2,4-F_2-phenyl | mp 176–177° C. |
| 630 | 2-MeSO_2 | i-Pr | 4-F-phenyl | |
| 631 | 2-CF_3, 4-Cl | i-Pr | 2,4-F_2-phenyl | mp 124–125° C. |
| 632 | 2-CF_3, 4-Cl | i-Pr | 4-F-phenyl | mp 154–155° C. |
| 633 | 2-Cl, 4-Me | i-Pr | 2,4-F_2-phenyl | mp 139–140° C. |

TABLE 1a-continued
General formula (Ia)
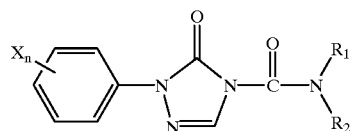
| Compound No. | X_n | R_1 | R_2 | Physical data |
|---|---|---|---|---|
| 634 | 2-Cl, 4-Me | i-Pr | 4-F-C6H4 | mp 178–179° C. |
| 635 | 2-Me, 4-Cl | i-Pr | 2,4-F2-C6H3 | mp 136–137° C. |
| 636 | 2-Me, 4-Cl | i-Pr | 4-F-C6H4 | mp 142–143° C. |
| 637 | 2-Me, 3-Cl | i-Pr | 2,4-F2-C6H3 | mp 111–112° C. |
| 638 | 2-Me, 3-Cl | i-Pr | 4-F-C6H4 | mp 121–122° C. |
| 639 | 2-Me, 5-Cl | i-Pr | 2,4-F2-C6H3 | mp 136–137° C. |
| 640 | 2-Me, 5-Cl | i-Pr | 4-F-C6H4 | mp 146–147° C. |
| 641 | 2-CN | i-Pr | 2,4-F2-C6H3 | mp 115–117° C. |
| 642 | 2-CN | i-Pr | 4-F-C6H4 | mp 126–127° C. |
| 643 | 2-NO_2 | i-Pr | 2,4-F2-C6H3 | mp 131–132° C. |

TABLE 1a-continued
General formula (Ia)
| Compound No. | $X_n$ | $R_1$ | $R_2$ | Physical data |
|---|---|---|---|---|
| 644 | 2-NO$_2$ | i-Pr | 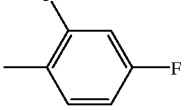 | mp 135–136° C. |
| 645 | 2-NHCOMe | i-Pr |  | mp 105–107° C. |
| 646 | 2-NHCOMe | i-Pr | 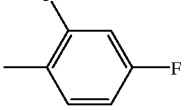 | $n_D^{18}$1.5576 |
| 647 | 2-NHCOCF$_3$ | i-Pr | 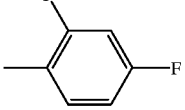 | mp 132–133° C. |
| 648 | 2-NHCOCF$_3$ | i-Pr |  | mp 143–144° C. |

TABLE 1b
General formula (Ib):
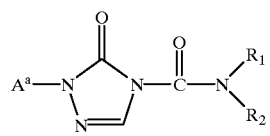
where $A^a$ means 1-naphthyl group
or 5,6,7,8-tetrahydro-1-naphthyl group
| Compound No. | $A^a$— | $R_1$ | $R_2$ | Physical data |
|---|---|---|---|---|
| 649 | 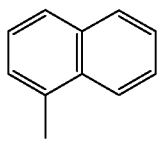 | i-Pr | ![4-F-phenyl] | mp 90–92° C. |
| 650 | 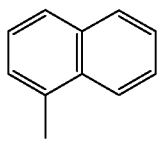 | i-Pr | ![2,4-diF-phenyl] | mp 95–96° C. |
| 651 | 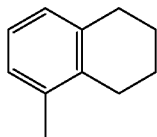 | i-Pr | ![4-F-phenyl] | mp 130–131° C. |
| 652 | 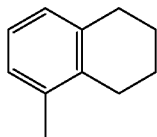 | i-Pr | ![2,4-diF-phenyl] | mp 77–78° C. |

TABLE 1c
General formula (Ic):
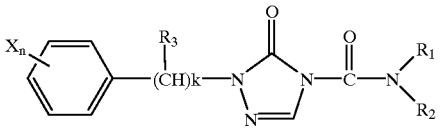
| Compound No. | 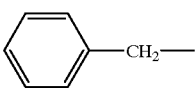 | R₁ | R₂ | Physical data |
|---|---|---|---|---|
| 653 | 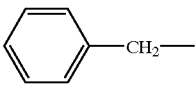 | Et | Et | |
| 654 | 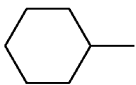 | Et | 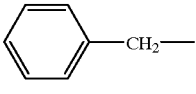 | mp 75–76° C. |
| 655 | 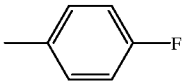 | i-Pr | 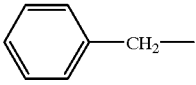 | mp 96–97° C. |
| 656 | 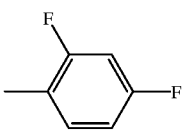 | i-Pr | 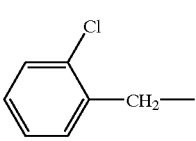 | mp 109–111° C. |
| 657 | 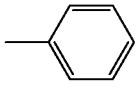 | i-Pr | 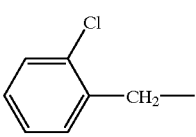 | |
| 658 | 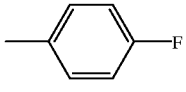 | i-Pr | 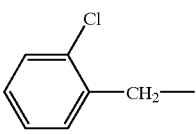 | mp 104–105° C. |
| 659 | 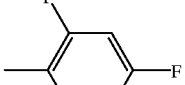 | i-Pr | 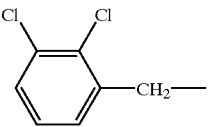 | mp 99–101° C. |
| 660 | 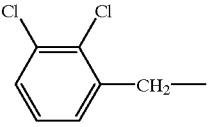 | Et | Et | $n_D^{18}$ 1.5511 |
| 661 | 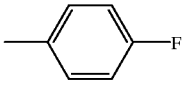 | i-Pr | | mp 90–92° C. |

TABLE 1c-continued
General formula (Ic):
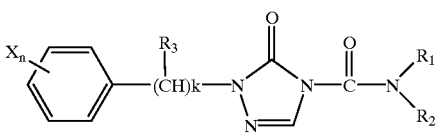
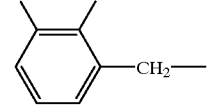
| Compound No. | | $R_1$ | $R_2$ | Physical data |
|---|---|---|---|---|
| 662 | 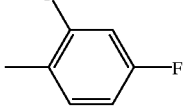 | i-Pr | 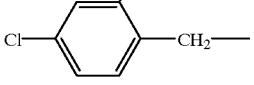 | mp 91–92° C. |
| 663 | 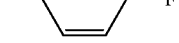 | i-Pr | 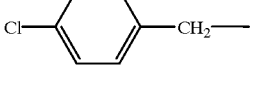 | |
| 664 | 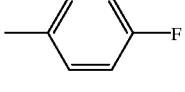 | i-Pr | 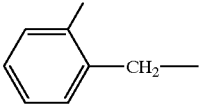 | |
| 665 |  | i-Pr | 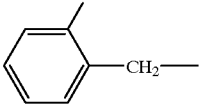 | mp 87–89° C. |
| 666 | 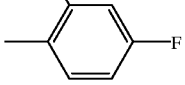 | i-Pr | 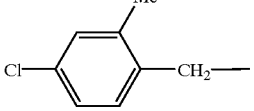 | mp 93–94° C. |
| 667 |  | i-Pr | 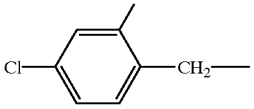 | |
| 668 | 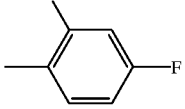 | i-Pr | 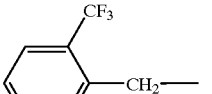 | |
| 669 | 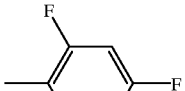 | i-Pr | 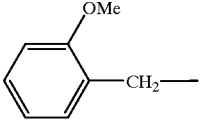 | |
| 670 | 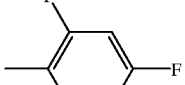 | i-Pr | | |

TABLE 1c-continued

General formula (Ic):

| Compound No. | | R₁ | R₂ | Physical data |
|---|---|---|---|---|
| 671 | 2-(OCF₃)C₆H₄-CH₂- | i-Pr | 2,4-F₂C₆H₃- | |
| 672 | C₆H₅-CH(Me)- | i-Pr | 4-F-C₆H₄- | |
| 673 | C₆H₅-CH(Me)- | i-Pr | 2,4-F₂C₆H₃- | |
| 674 | 2-Cl-C₆H₄-CH(Me)- | i-Pr | 4-F-C₆H₄- | |
| 675 | 2-Cl-C₆H₄-CH(Me)- | i-Pr | 2,4-F₂C₆H₃- | mp 160–161° C. |
| 676 | 2,4-Cl₂-C₆H₃-CH(Me)- | i-Pr | 2,4-F₂C₆H₃- | |
| 677 | 2-Me-C₆H₄-CH(Me)- | i-Pr | 2,4-F₂C₆H₃- | mp 164–165° C. |
| 678 | C₆H₅-CH₂CH₂- | i-Pr | 2,4-F₂C₆H₃- | mp 128–130° C. |
| 679 | C₆H₅-CH₂CH₂- | i-Pr | 4-F-C₆H₄- | |

TABLE 1c-continued

General formula (Ic):

$$\text{X}_n\text{-Ph-(CH)}_k\text{-N-N=CH-N(C=O)-C(=O)-N(R}_1\text{)(R}_2\text{)}$$

| Compound No. | (Xn-Ph-(CH)k-) group | R₁ | R₂ | Physical data |
|---|---|---|---|---|
| 680 | 2-Cl-C₆H₄-CH₂CH₂- | i-Pr | 2,4-F₂-C₆H₃- | |
| 681 | 2-Me-C₆H₄-CH₂CH₂- | i-Pr | 2,4-F₂-C₆H₃- | |
| 682 | 2,4-Cl₂-C₆H₃-CH₂CH₂- | i-Pr | 2,4-F₂-C₆H₃- | |
| 683 | 2-Cl-4-Me-C₆H₃-CH₂CH₂- | i-Pr | 4-F-C₆H₄- | |
| 684 | 2-CF₃-C₆H₄-CH₂CH₂- | i-Pr | 2,4-F₂-C₆H₃- | |

Next, a process for the production of a 1-substituted-4-carbamoyl-1,2,4-triazol-5-one derivative of the general formula (I) according to the first aspect of this invention will be explained.

Generally, the compound of the general formula (I) may be prepared by a process which comprises reacting a 1-substituted-1,2,4-triazol-5-one derivative of the general formula (II) given below with a carbamoyl chloride of the general formula (III) given below.

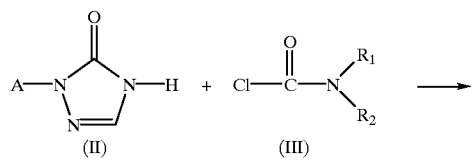

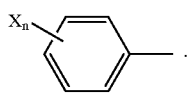

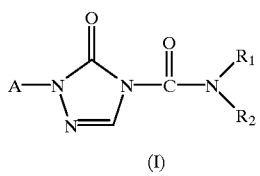

(I)

In the above reaction equation, A means an unsubstituted or substituted phenyl group of the following formula:

where X and n have the same meanings as defined above, or A means 1-naphtyl group, 5,6,7,8-tetrahydro-1-naphtyl group or an aralkyl group of the formula:

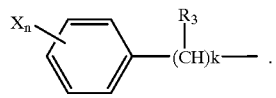

where X, n, R$_3$ and k have the same meanings as defined above and R$_1$ and R$_2$ have the same meanings as defined above (the same definitions as above are used likewise hereinafter).

The reaction in the above-mentioned process can be achieved by contacting the 1-substituted-1,2,4-triazol-5-one derivative of the general formula (II) with the carbamoyl chloride of the general formula (III) in an organic solvent in the presence of a dehydrochlorinating agent.

As the dehydrochlorinating agent used in the above-mentioned reaction, there may be mentioned a base, for example, an organic tertiary amine such as triethylamine, tributylamine, diethylisopropylamine, 4-dimethylaminopyridine and pyridine, or an alkali metal carbonate such as sodium carbonate or potassium carbonate, or an alkali metal hydroxide such as sodium hydroxide and potassium hydroxide. Preferred bases are pyridine and potassium carbonate. Preferably, said base is used in an amount of about one equivalent proportion when sodium carbonate is used. However, when pyridine is used as the base, pyridine is used in an excess amount since it acts also as a solvent.

As the solvent usable in the reaction, there may be mentioned an aromatic hydrocarbon such as benzene, toluene and xylene; a halogenated hydrocarbon such as dichloromethane, chloroform, carbon tetrachloride, dichloroethane, trichloroethane and tetrachloroethane; a nitrile such as acetonitrile and propionitrile; an ester such as ethyl acetate and ethyl propionate; an ether such as diethyl ether and tetrahydrofuran; a ketone such as acetone and methyl ethyl ketone; and pyridine and so on. A mixture of these solvents may also be used. Acetone and pyridine are preferred.

The reaction is carried out usually at a temperature ranging from room temperature to 150° C., but preferably at 20 to 80° C. The reaction is completed usually in a time of between 30 minutes and 24 hours, depending upon the reaction temperature and reactants used.

The compound of the general formula (I) which is a target reaction product may be recovered from the resulting reaction solution by subjecting the reaction solution to usual post-treatments. For example, said target compound can be harvested by adding water to the reaction solution, washing the solution with water and then distillating off the solvent. The resulting target product may further be purified by an operation such as column chromatography or recrystallization, if necessary.

Examples of the production of the compound of the general formula (I) of this invention according to the above-mentioned process are illustrated with reference to Examples 1 to 9 given hereinafter.

By the way, the 1-substituted-1,2,4-triazol-5-one derivatives of the general formula (II) used as the starting material in the above-mentioned process are either a novel compound or a known compound. For example, they can easily be synthesized according to the method as described in the "SYNTHETIC COMMUNICATIONS", Vol.16 (2), pages 163 to 167 (1986). The production of them are illustrated with reference to Referential Production Examples 1 to 4 given hereinafter.

Also, the carbamoyl chlorides of the general formula (III) used as the reactant in the process above are well known in the field of an organic chemistry and can easily be synthesized according to the method as described in the "Chemische Berichte", Vol.88, page 301 (1955).

Furthermore, a herbicidal composition according to the second aspect of this invention will now be described concretely.

The compound of the general formula (I) according to this invention has an excellent herbicidal activity as shown in Test Examples hereinafter and can be used as a herbicide for combatting weeds. The compound of this invention can be used as a selective herbicide since the compound may exhibit a selective herbicidal activity between weeds and crop plants as shown below.

As unwanted grass weeds, there may be mentioned water foxtail (Alopecurus), wild oat (Avena), rescue grass (Bromus), iris sedge (Cyperus), southern crabgrass (Digitaria), barnyard grass (Echinochloa), water chestnut (Eleocharis), goose grass (Eleusine), pickerelweed (Monochoria), fall panicum (Panicum), dallisgrass (Paspalum), timothy (Phleum), annual bluegrass (Poa), arrowhead (Sagittaria), Japanese bulrush (Scirpus), green foxtail (Setaria), Johnson glass (Sorghum) and the like.

As unwanted broad-leaved weeds, there may be mentioned vervetleaf (Abutilon), livid amaranth (Amaranthus), ragweed (Ambrosia), hairy beggarticks (Bidens), lamb's quarters (Chenopodium), cleaver (Galium), bindweed (Ipomoea), common false pimpernel (Lindernia), smartweed (Persicaria), common purslane (Portulaca), Indian toothcup (Rotala), common chickweed (Stellaria), violet (Viola), heartleaf cocklebur (Xanthium) and the like.

As useful cultivative crops plants of Gramineae grown in the field where the compound of this invention may be applied, there may be mentioned barley (Hordeum), rice (Oryzae), sugar cane (Saccharum), wheat (Triticum), maize (Zea) and the like. As broad-leaved crops, there may be mentioned peanut (Arachis), sugar beet (Beta), rape (Brassica), soy bean (Glycine), cotton (Gossypium), tomato (Lyncopersicon) and the like.

It is needless to say that the use of the compound of the general formula (I) as herbicide is not limited to the above-mentioned unwanted weeds and the fields for the above-mentioned crop plants.

In the preparation of the herbicidal composition according to the second aspect of this invention, the 1-substituted-4-carbamoyl-1,2,4-triazol-5-one derivative according to the first aspect of this invention may be formulated into a composition wherein said compound is incorporated as an active ingredient in combination with a carrier. When formulating into such a herbicidal composition, it is possible to formulate into various appropriate forms usually usable in the field of pesticide, for example, granules, fine granules, wettable powder, granular wettable powder, emulsifiable concentrate, aqueous solution, flowable preparation, tablet, powder and so on, by mixing the compound of the general formula (I) as the active ingredient with a carrier or diluent, and, if desired, also with at least one of additives and auxiliary agents, in a conventional manner.

Also, it is possible to use the compound of this invention in association with other pesticides such as fungicide, insecticide, herbicide, acaricide, plant growth regulating agent, fertilizer, soil conditioner and the like. Particularly, by using the compound of this invention in association with other herbicide, it is possible not only to reduce the applied amount of the compound of this invention and to gain a labour-saving, but also it can be expected to obtain a spreading of the herbicidal spectrum due to the cooperative action of both the agents, as well as enhanced herbicidal effect due to synergistic action. Then, it is also possible to combine the compound of this invention with two or more known herbicides.

The carrier which may be used in the above-mentioned formulation of the herbicidal composition includes such ones which are conventionally employed in the preparations of agricultural utility, and which may be either solid or liquid. The available carrier is not limited to specific one. For example, the solid carrier may include mineral powders such as kaolin, bentonite, clay, montmorilonite, talc, diatomaceous earth, mica, vermiculite, quartz, calcium carbonate, phosphorite, white carbon, slaked lime, silicious sand, ammonium sulfate and urea; vegetable powders such as soya bean flour, wheat flour, wood meal, tobaco powder, starch and crystalline cellulose; macromolecular compounds such as petroleum resin, polyvinyl chloride and ketone resin; alumina, silicates, sugar polymers, high-dispersible silicic acid and waxes.

The usable liquid carrier may include water; alcohols such as methanol, ethanol, n-propanol, iso-propanol, butanol, ethylene glycol and benzyl alcohol; aromatic hydrocarbons such as toluene, benzene, xylene, ethylbenzene and methylnaphthalene; halogenated hydrocarbons such as chloroform, carbon tetrachloride, dichloromethane, chloroethylene, monochlorobenzene, trichlorofluoromethane and dichlorofluoromethane; ethers such as ethyl ether, ethylene oxide, dioxane and tetrahydrofuran; ketones such as acetone, methyl ethyl ketone, cyclohexanone, methyl isobutyl ketone and isophorone; esters such as ethyl acetate, butyl acetate, ethylene glycol acetate and amyl acetate; acid amides such as dimethylformamide and dimethylacetamide; nitriles such as acetonitrile, propionitrile and acrylonitrile; sulfoxides such as dimethylsulfoxide; alcohol ethers such as ethylene glycol monomethylether and ethylene glycol monoethylether; aliphatic and cycloaliphatic hydrocarbons such as n-hexane and cyclohexane; industrial gasoline such as petroleum ether and solvent naphtha; and petroleum fractions such as paraffins, kerosene and gas oil.

When the herbicidal composition is prepared in the form of emulsifiable concentrate, wettable powder, flowable preparation and the like, various kinds of surface active agents may be added in the composition for the purpose of emulsification, dispersion, solubilization, wetting, foaming, lubrication, spreading or the like. These surface active agents may be a surface active agent of non-ionic type such as polyoxyethylene alkylethers, polyoxyethylene alkylesters and polyoxyethylene sorbitan alkylesters; a surface active agent of anionic type such as alkylbenzene sulfonates, alkylsulfosuccinate, alkyl sulphates, polyoxyethylene alkylsulfate and aryl sulfonate; and a surface active agent of cationic type such as alkylamines (laurylamine, stearyl trimethyl ammonium chloride and the like) and polyoxyethylene alkylamine; as well as a surface active agent of amphoteric type such as carboxylic acid of betaine type and salts of sulfuric esters. Of course, the surface active agents usable for this invention are not limited to these surface active agents as exemplified above.

In addition to the additives mentioned above, the herbicidal composition may further contain a variety of adjuvants, for example, polyvinyl alcohol (PVA), carboxymethylcellulose (CMC), gum arabic, polyvinyl acetate, sodium alginate, gelatine, casein and traganth gum.

When the herbicidal composition of the second aspect of this invention is formulated in any various forms as exemplified above, the compound of the general formula (I) according to this invention may be incorporated in the composition in an amount of 0.001% to 95% by weight, preferably, 0.01% to 75% by weight of the composition. Unless otherwise stated hereinafter, the % value is given on the weight basis hereinafter. For example, the content of the compound of the formula (I) may usually be 0.01% to 10% in the composition in the form of powder; or 1% to 75% in the composition in the form of a wettable powder, flowable preparation, solution or emulsifiable concentrate; or 0.01% to 5% in the composition in the form of powder, driftless powder or fine powder.

The herbicidal composition so prepared, for example, in the form of granules and flowable preparation, may be applied by scattering the composition as such on the surface of soil or in the soil or in aquatic medium so that the amount of the active ingredient applied is in a range of 0.3 g to 300 g per 10 ares of a farm field. When the herbicidal composition is prepared in the form of a wettable powder and emulsifiable concentrate, the herbicidal composition of this form is first diluted with water or an appropriate organic solvent and the so-diluted liquid preparation is then applied so that the amount of the active ingredient applied is in a range of 0.3 g to 300 g per 10 ares of a farm field.

In addition, it has been found that a number of the exemplified compounds among the compounds of the general formula (I) according to the first aspect of this invention can completely kill weeds of the paddy field and weeds of farm field at a rate of kill of weed of 100%, even when they are applied at a rate as low as 3 g to 30 g per 10 ares of the field and thus they can exhibit an excellent herbicidal activity.

Hereinafter, several examples of the production of the compound of the general formula (I) according to this invention will be described with reference to the following Examples and Referential Production Examples.

EXAMPLE 1

Production of 1-(2-chlorophenyl)-4-(N-isopropyl-N-2,4-difluorophenylcarbamoyl)-1,2,4-triazol-5-one (Compound No.35 of Table 1a)

To a solution of 1-(2-chlorophenyl)-1,2,4-triazol-5-one (2.0 g) in acetonitrile (50 ml) was added potassium carbonate (1.7 g). The resulting mixture was stirred for 30 minutes at room temperature, and N-isopropyl-N-2,4-difluorophenylcarbamoyl chloride (3.0 g) was added to the mixture, followed by stirring the resulting mixture for one hour at 80° C. The resulting reaction solution was then filtered to remove the inorganic salt as formed therefrom. Thereafter, the solvent was distilled out from the filtrate under reduced pressure. The residue obtained was dissolved in 80 ml of toluene, and the resulting solution was washed with water and then dried over anhydrous sodium sulfate. Thereafter, the solvent was distilled off from the solution. The residue so obtained was purified by silica gel chromatography to give 3.2 g of the titled target compound (at a yield of 80%). Melting point of 146 to 148° C.

EXAMPLE 2

Production of 1-(2-chlorophenyl)-4-(N-isopropyl-N-4-fluorophenylcarbamoyl)-1,2,4-triazol-5-one (Compound No.38 of Table 1a)

To a solution of 1-(2-chlorophenyl)-1,2,4-triazol-5-one (2.0 g) in pyridine (50 ml) was added N-isopropyl-N-fluorophenylcarbamoyl chloride (2.6 g). The resulting mixture was left to stand for 20 hours at room temperature. Pyridine was distilled off from the resulting reaction solution under reduced pressure. The resulting residue was dissolved in 80 ml of toluene, and the solution obtained was washed with 1N aqueous hydrochloric acid and then with water and dried over anhydrous sodium sulfate. The dried solution was distilled to remove the solvent therefrom, and the resulting residue was purified by silica gel chromatography to give 2.9 g of the titled target compound (at a yield of 77%). Melting point of 118 to 120° C.

EXAMPLE 3

Production of 1-phenyl-4-(N-isopropyl-N-phenyl-carbamoyl)-1,2,4-triazol-5-one (Compound No.1 of Table 1a)

To a solution of 1-phenyl-1,2,4-triazol-5-one (1.6 g) in pyridine (50ml) was added N-isopropyl-N-phenylcarbamoyl chloride (2.4 g). The resulting mixture was left to stand for 20 hours at room temperature. Pyridine was distilled off from the resulting reaction solution under reduced pressure. The resulting residue was dissolved in 80 ml of toluene, and the solution obtained was washed with 1N aqueous hydrochloric acid and then with water and dried over anhydrous sodium sulfate. The solvent was distilled off from the solution and the resulting residue was purified by silica gel chromatography to give 2.4 g of the titled target compound (at a yield of 77%). Melting point of 144 to 145° C.

EXAMPLE 4

Production of 1-(2-chlorophenyl)-4-(N-ethyl-N-2,4-difluorophenylcarbamoyl)-1,2,4-triazol-5-one (Compound No.26 of Table 1a)

To a solution of 1-(2-chlorophenyl)-1,2,4-triazol-5-one (2.0 g) in pyridine (50ml) was added N-ethyl-N-2,4-difluorophenylcarbamoyl chloride (2.8 g). The resulting mixture was left to stand for 20 hours at room temperature. Pyridine was distilled off from the resulting reaction solution under reduced pressure. The resulting residue was dissolved in 80 ml of toluene, and the solution obtained was washed with 1N aqueous hydrochloric acid and then with water and dried over anhydrous sodium sulfate. The solvent was distilled off from the solution and the resulting residue was purified by silica gel chromatography to give 3.0 g of the titled target compound (at a yield of 79%). Melting point of 110 to 111° C.

EXAMPLE 5

Production of 1-(2-chlorophenyl)-4-(N-ethyl-N-cyclohexylcarbamoyl)-1,2,4-triazol-5-one (Compound No.66 of Table 1a)

To a solution of 1-(2-chlorophenyl)-1,2,4-triazol-5-one (2.0 g) in pyridine (50 ml) was added N-ethyl-N-cyclohexylcarbamoyl chloride (2.0 g). The resulting mixture was left to stand for 20 hours at room temperature. Pyridine was distilled off from the resulting reaction solution under reduced pressure. The resulting residue was dissolved in 80 ml of toluene, and the solution obtained was washed with 1N aqueous hydrochloric acid and then with water and dried over anhydrous sodium sulfate. The solvent was distilled off from the solution and the resulting residue was purified by silica gel chromatography to give 3.0 g of the titled compound (at a yield of 84%, melting point of 105 to 106° C.).

EXAMPLE 6

Production of 1-(2-methylphenyl)-4-(N-isopropyl-N-2,4-difluorophenylcarbamoyl) -1,2, 4-triazol-5-one (Compound No.331 of Table 1a)

To a solution of 1-(2-methylphenyl)-1,2,4-triazol-5-one (1.89) in pyridine (50 ml) was added N-isopropyl-N-2,4-difluorophenylcarbamoyl chloride (3.0 g). The resulting mixture was left to stand for 20 hours at room temperature. Pyridine was distilled off from the resulting reaction solution under reduced pressure. The resulting residue was dissolved in 80 ml of toluene, and the solution obtained was washed with 1N aqueous hydrochloric acid and then with water and dried over anhydrous sodium sulfate. The solvent was distilled off from the solution and the resulting residue was purified by silica gel chromatography to give 3.1 g of the titled target compound (at a yield of 81%). Melting point of 106 to 107° C.

EXAMPLE 7

Production of 1-(2,4-dichlorophenyl)-4-(N-isopropyl-N-2,4-difluorophenylcarbamoyl)-1,2,4-triazol-5-one (Compound No.231 of Table 1a)

To a solution of 1-(2,4-dichlorophenyl)-1,2,4-triazol-5-one (2.3 g) in pyridine (50ml) was added N-isopropyl-N-2,4-difluorophenylcarbamoyl chloride (3.0 g). The resulting mixture was left to stand for 20 hours at room temperature. Pyridine was distilled off from the resulting reaction solution under reduced pressure. The resulting residue was dissolved in 80 ml of toluene, and the solution obtained was washed with 1N aqueous hydrochloric acid and then with water and dried over anhydrous sodium sulfate. The solvent was distilled off and the resulting residue was purified by silica gel chromatography to give 3.1 g of the titled target compound (at a yield of 71%). Melting point of 129 to 131° C.

EXAMPLE 8

Production of 1-(2-chloro-α-methylbenzyl)-4-(N-isopropyl-N-2,4-difluorophenylcarbamoyl)-1,2,4-triazol-5-one (Compound No.675 of Table 1c)

To a solution of 1-(2-chloro-α-methylbenzyl)-1,2,4-triazol-5-one (1.0 g) in acetonitrile (30 ml) was added potassium carbonate (0.8 g) . The resulting mixture was stirred for 30 minutes at room temperature and then N-isopropyl-N-2,4-difluorophenylcarbamoyl chloride (1.3 g) was added thereto. The resulting mixture was stirred for one hour at 80° C. The resulting reaction solution was then filtered to remove the inorganic salt as formed therefrom. Thereafter, the solvent was removed from the filtrate by distillation under reduced pressure. The residue obtained was dissolved in 50 ml of toluene, and the resulting solution was washed with water and then dried over anhydrous sodium sulfate. Thereafter, the solvent was distilled off from the solution. The residue so obtained was purified by silica gel chromatography to give 1.3 g of the titled target compound (at a yield of 68%). Melting point of 160 to 161° C.

EXAMPLE 9

Production of 1-benzyl-4-(N-isopropyl-N-2,4-difluorophenylcarbamoyl)-1,2,4-triazol-5-one (Compound No.656 of Table 1c)

1-benzyl-1,2,4-triazol-5-one (1.3 g) and N-isopropyl-N-2,4-difluorophenylcarbamoyl chloride (2.3 g) were added to pyridine (30 ml). The resulting mixture was stirred for one hour at room temperature and then left to stand over night. To the resulting reaction solution were added toluene (150 ml) and water (150 ml). Then, the resulting mixture was separated into two phases. The toluene layer obtained was further washed with 1N aqueous hydrochloric acid and with a saturated aqueous sodium chloride solution and subsequently dried over anhydrous sodium sulfate. The dried toluene solution was distilled under reduced pressure to remove the solvent, and the resulting residue was purified by silica gel chromatography to give 1.5 g of the titled target compound (at a yield of 54%). Melting point of 109 to 111° C.

REFERENTIAL PRODUCTION EXAMPLE 1

Preparation of 1-(2-chlorophenyl)-1,2,4-triazol-5-one 25 g of 2-chlorophenylhydrazine hydrochloride was dissolved in 230 ml of water. To the resulting solution, 29 g of an aqueous solution of 40% of glyoxylic acid was added dropwise under ice-cooling. The resulting mixture was stirred for 2 hours at a temperature of 10 to 20° C. and the powder thus deposited was recovered by filtration under suction and then washed with water. The resulting powder was dried under reduced pressure in a desiccator to obtain 27.2 g of a brown powder. 27.2 g of the powder so obtained was suspended in 400 ml of toluene, and 14 g of triethylamine was added dropwise to the resulting suspension, followed by adding dropwise 37.8 g of diphenylphosphoryl azide to it. The resulting mixture was stirred under heating for 4 hours at 70 to 80° C. and further for 2 hours at 100° C. The resulting reaction solution was allowed to cool and then extracted with 760 ml of 1N aqueous potassium hydroxide solution under cooling with ice-water. The alkaline aqueous layer obtained as the extract solution was made acidic by adding 160 g of a concentrated hydrochloric acid portionwise. The crystals thus deposited were separated by filtration and washed with water. The resulting crystals were dissolved in a mixed solvent of toluene and ethanol, and the solution obtained was subjected to azeotropic distillation under reduced pressure to remove water therefrom. The crystals so obtained were recrystallised from ethyl acetate to obtain 19.1 g of the titled target compound (at a yield of 70%). Melting point of 155 to 156° C.

REFERENTIAL PRODUCTION EXAMPLE 2

Preparation of 1-phenyl-1,2,4-triazol-5-one 12 g of phenylhydrazine hydrochloride was dissolved in 100 ml of water. To the resulting solution was added 15.3 g of an aqueous solution of 40% of glyoxylic acid dropwise under ice-cooling. The resulting mixture was stirred for 2 hours at a temperature of 10 to 20° C. The powder thus deposited was separated by filtration under suction and then washed with water. The resulting powder was dried under reduced pressure in a desiccator to obtain 12.9 g of a brown powder. 12.9 g of the powder thus obtained was suspended in 250 ml of toluene, and to the resulting suspension was added dropwise 7.9 g of triethylamine, followed by adding dropwise 21.7 g of diphenylphosphoryl azide. The resulting reaction mixture was stirred under heating for 2 hours at 70 to 80° C. and further for 1 hour at 100° C. The resulting reaction solution was allowed to cool and then extracted with 400 ml of 2N aqueous sodium hydroxide solution under cooling with ice-water. The alkaline aqueous layer obtained as the extract solution was made acidic by adding 90 g of a concentrated hydrochloric acid portionwise. The crystals thus deposited were recovered by filtration and washed with water. The resulting crystals were dissolved in a mixed solvent of toluene and ethanol, and the solution obtained was subjected to azeotropic distillation under reduced pressure to remove water therefrom. The crystals so obtained were recrystallised from ethyl acetate to obtain 9.1 g of the titled target compound (at a yield of 68%) Melting point of 182 to 183° C.

REFERENTIAL PRODUCTION EXAMPLE 3

Preparation of 1-(2-chloro-α-methylbenzyl)-1,2,4-triazol-5-one 4.5 g of 2-chloro-α-methylhydrazine hydrochloride was dissolved in 100 ml of water. To the resulting solution, 4.1 g of an aqueous solution of 40% of glyoxylic acid was added dropwise under ice-cooling. The resulting mixture was stirred for 2 hours at a temperature of 10 to 20° C. and then the powder thus deposited was recovered by filtration under suction and then washed with water. The resulting powder was dried under reduced pressure in a desiccator to obtain 4.7 g of a brown powder. 4.7 g of the powder obtained was suspended in 100 ml of toluene, and to the resulting suspension was then added dropwise 2.1 g of triethylamine, followed by adding dropwise 5.7 g of diphenylphosphoryl azide. The resulting reaction mixture was stirred under heating for 1 hour at 70 to 80° C. and further for 1 hour at 100° C. The resulting reaction solution was allowed to cool and then extracted with 100 ml of 2N aqueous potassium hydroxide solution under cooling with ice-water. The alkaline aqueous layer so obtained as the extract solution was made acidic by adding 25 g of a concentrated hydrochloric acid portionwise. The crystals thus deposited were separated by filtration and washed with water. The resulting crystals were dissolved in a mixed solvent of toluene and ethanol, and the solution obtained was subjected to azeotropic distillation under reduced pressure to remove water therefrom. The crystals so obtained were recrystallised from ethyl acetate to obtain 3.0 g of the titled target compound (at a yield of 65%). Melting point of 141 to 144° C.

REFERENTIAL PRODUCTION EXAMPLE 4

Preparation of 1-benzyl-1,2,4-triazol-5-one 16.2 g of benzylhydrazine dihydrochloride was dissolved in 300 ml of water. To the resulting solution, 15.4 g of an aqueous solution of 40% of glyoxylic acid was added dropwise under cooling with ice-water. The resulting mixture was stirred for 1 hour at a temperature of 10 to 20° C. and the powder thus deposited was recovered by filtration and washed with water. The resulting powder was dried under reduced pressure in a desiccator to obtain 9.9 g of a brown powder. 9.0 g of the powder obtained was suspended in 250 ml of toluene, and to the resulting suspension was added dropwise 5.1 g of triethylamine, followed by adding dropwise 13.9 g of diphenylphosphoryl azide. The resulting reaction mixture was stirred under heating for 1 hour at 70 to 80° C. and further for 1 hour at 100° C. The resulting reaction solution was allowed to cool and then extracted with 300 ml of 2N aqueous sodium hydroxide solution under cooling with ice-water. The resulting alkaline aqueous layer was made acidic by adding portionwise 60 g of a concentrated hydrochloric acid and then extracted with 150 ml of ethyl acetate. The resulting ethyl acetate layer (the extract solution) was washed with a saturated aqueous sodium chloride solution and then dried over anhydrous sodium sulfate. The resulting dried solution was distilled under reduced pressure to remove the solvent. The resulting residue was purified by silica gel chromatography to obtain 4.7 g of the titled target compound (at a yield of 53%) Melting point of 147 to 149° C.

Another representative particular examples of the 1-substituted-1,2,4-triazole which are represented by the general formulas (IIa), (IIb) and (IIc) given below and which were produced in the same manner as in the above Referential Production Examples 1 to 4 are shown in the following Tables 2-1, 2-2 and 2-3.

TABLE 2-1

General formula (IIa):

[Structure: X_n-phenyl-triazolone with N-H]

| $X_n$ | mp. |
| --- | --- |
| H | 182–183° C. |
| 2-Cl | 155–156° C. |
| 4-Cl | 256–257° C. |
| 2-F | 164–165° C. |
| 3-F | 166–168° C. |
| 4-F | 231–232° C. |
| 2-Br | 150–151° C. |
| 2,3-Cl$_2$ | 194–195° C. |
| 2,4-Cl$_2$ | 188–189° C. |
| 2,5-Cl$_2$ | 183–185° C. |
| 2,6-Cl$_2$ | 243–244° C. |
| 2-F,4-Cl | 208–209° C. |
| 2,4-F$_2$ | 231–232° C. |
| 2-Me | 148–149° C. |
| 3-Me | 183–184° C. |
| 4-Me | 211–212° C. |
| 2-Et | 149–151° C. |
| 2-n-Pr | 113–114° C. |
| 2-i-Pr | 153–154° C. |
| 2,3-(Me)$_2$ | 190–192° C. |
| 2,4-(Me)$_2$ | 146–148° C. |
| 2,5-(Me)$_2$ | 135–137° C. |
| 2,6-(Me)$_2$ | 167–168° C. |
| 2-Me,6-Et | 143–144° C. |
| 2-MeO | 127–128° C. |
| 4-MeO | 180–181° C. |
| 2-MeS | 136–138° C. |
| 2-CN | 169–171° C. |
| 4-CF$_3$ | 258–260° C. |
| 2-Me,3-Cl | 197–198° C. |
| 2-Me,4-Cl | 192–193° C. |
| 2-Me,5-Cl | 187–188° C. |
| 2-Me,6-Cl | 198–199° C. |
| 4-Me,2-Cl | 159–161° C. |
| 2-NO$_2$ | 181–182° C. |
| 2-NHCOMe | 262–263° C. |
| 2-NHCOCF$_3$ | 156–158° C. |
| 2,4,6-Cl$_3$ | 268–269° C. |

TABLE 2-2

General formula (IIb):

[Structure: A$^a$-N-triazolone-N-H]

where A$^a$ means

[naphthalenyl structure]

or

[tetrahydronaphthalenyl structure]

| A$^a$ | mp. |
| --- | --- |
| [naphthalenyl] | mp 188–189° C. |
| [tetrahydronaphthalenyl] | mp 191–192° C. |

TABLE 2-3

General formula (IIc):

[Structure: X_n-phenyl-(CH)k-R_3-triazolone-N-H]

| Xn | R$_3$ | k | mp. |
| --- | --- | --- | --- |
| H | H | 1 | 147–149° C. |
| 2-Cl | H | 1 | 162–164° C. |
| 2-Me | H | 1 | 166–168° C. |
| 2-Cl | Me | 1 | 141–144° C. |
| 2-Me | Me | 1 | 156–158° C. |

Furthermore, various and exemplary formulations of the herbicidal composition comprising the compound of the above general formula (I) according to this invention are now illustrated with reference to the following Examples 10 to 15, to which this invention is not limited in any way. It is feasible to incorporate in the exemplified formulations optional proportions of another different additives and also to formulate the exemplified formulations in any desired form. Compound No. shown in the following Examples indicates the compound number listed in Tables 1a, 1b and 1c given hereinbefore. In these Examples, "part" or "parts" are all given on the weight basis.

EXAMPLE 10 (Granules)

| | |
| --- | --- |
| Compound No. 1 | 1 part |
| Calcium ligninsulfonate | 1 part |
| Lauryl sulfate | 1 part |
| Bentonite | 30 parts |
| Talc | 67 parts |

The resultant mixture of the above ingredients was mixed with 15 parts of water and then kneaded in a kneader. The kneaded mixture was granulated in an extruder-type granulating machine, and the granules obtained were dried in a drying apparatus of fluidization-type. In this way, the granules containing 1% by weight of the active ingredient were prepared.

EXAMPLE 11 (Flowable preparation)

| | |
|---|---|
| Compound No. 35 | 20.0 parts |
| Di-2-ethylhexyl sulfosuccinate sodium salt | 2.0 parts |
| Polyoxyethylene nonylphenyl ether | 2.0 parts |
| Propylene glycol | 5.0 parts |
| Anti-foaming agent | 0.5 parts |
| Water | 70.5 parts |

The above ingredients were evenly mixed with each other and ground in a wet-type ball mill. In this way, a flowable preparation containing 20% by weight of the active ingredient was prepared.

EXAMPLE 12 (Dry flowable preparation)

| | |
|---|---|
| Compound No. 331 | 75 parts |
| Isovan No. 1 (an anionic surfactant, a commercial product of Kurare Isoprene Chemical Co., Japan) | 10 parts |
| Vanilex N (an anionic surfactant, a commercial product of Sanyo Kokusaku Pulp Co., Japan) | 5 parts |
| White carbon | 5 parts |
| Clay | 5 parts |

The above ingredients were evenly mixed with each other and finely ground in a grinding and mixing machine. In this way, a dry flowable preparation (a granular wettable powder) containing 75% by weight of the active ingredient was prepared.

EXAMPLE 13 (Wettable powder)

| | |
|---|---|
| Compound No. 231 | 15 parts |
| White carbon | 15 parts |
| Calcium ligninsulfonate | 3 parts |
| Polyoxyethylene nonylphenyl ether | 2 parts |
| Diatomaceous earth | 5 parts |
| Clay | 60 parts |

The above ingredients were evenly mixed with each other in a grinding and mixing machine. In this way, a wettable powder containing 15% by weight of the active ingredient was prepared.

EXAMPLE 14 (Emulsifiable concentrate)

| | |
|---|---|
| Compound No. 8 | 20 parts |
| Sorpor 700H (an emulsifier, a commercial product of Toho Chemical Industry Co., Japan) | 20 parts |
| Xylene | 60 parts |

The above ingredients were mixed with each other. In this way, an emulsifiable concentrate containing 20% by weight of the active ingredient was prepared.

EXAMPLE 15 (Powder)

| | |
|---|---|
| Compound No. 481 | 0.5 parts |
| White carbon | 0.5 parts |
| Calcium stearate | 0.5 parts |
| Clay | 50.0 parts |
| Talc | 48.5 parts |

The above ingredients were ground and mixed homogeneously with each other. In this way, a powder containing 0.5% by weight of the active ingredient was obtained.

It will be needless to say that all the herbicidal compositions comprising the compound of the above general formula (I) according to this invention may be formulated into different types of herbicidal fromulations, respectively, similarly to the formulation Examples shown in above.

Now, the following Test Examples 1 to 4 are shown in order to demonstrate the herbicidal effects of the compounds of the formula (I) according to this invention.

Test Example 1

Tests of the herbicidal effects of the compound on early watergrass and tests of phyto-toxicity of the compound to aquatic rice plant (the herbicidal treatment on pre-emergence of unwanted weeds and the herbicidal treatment conducted one day after the transplantation of aquatic rice plant).

Each of pots having a top surface area of 1/5000 ares was filled with a soil of the irrigated rice field. The soil in each pot was added with a volume of water and with a complex fertilizer (N:P:K=17:17:17) and then was puddled. In the surface layer of the watered soil were sown uniformly seeds of early watergrass to depth of 1 cm in the surface layer of the soil. In the soil in each pot, there were transplanted seedlings of aquatic rice plants (variety:Nihonbare) of 2.5-leaved stage. Each pot was then irrigated with water and the depth of the irrigating water on the soil surface was kept at about 3 cm. Each pot was subsequently controlled under the condition of glass greenhouse.

A diluted solution of a wettable powder was prepared by diluting with water to a predetermined concentration of the active ingredient such a wettable powder which had been formulated similarly to the procedure of Example 13 above. One day after the transplantation of the aquatic rice plant, the diluted solution prepared as above was dropwise added at a predetermined rate to the irrigating water in the pot to conduct the herbicidal treatment. 28 Days after the herbicidal treatments, the herbicidal effects of the tested compound on early watergrass and phyto-toxicity of the tested compound to aquatic rice plant were assessed, and the rate (percentages) of kill of the weeds was calculated according to the under-mentioned calculation equation. The test results obtained are shown in Table 3 below.

Rate (%) of kill of weeds=[1−(a/b)]×100 wherein a represents the dry weight (g) of weeds in treated plot and b represents the dry weight (g) of weeds in untreated plot.

Besides, phyto-toxicity of the tested compound to aquatic rice plant was assessed according to the following gradings of evaluation.

| Gradings of evaluation for the Phyto-toxicity to rice plant | Observed degrees of damage of rice plant |
| --- | --- |
| 5 | Complete kill |
| 4 | Great damage |
| 3 | Medium damage |
| 2 | Low damage |
| 1 | Very low damage |
| 0 | Null |

As a reference chemical, comparative compound A indicated hereinafter was used, and a wettable powder containing said comparative compound A was prepared in accordance with the procedure of Example 13 above. As a comparative test, the resultant diluted solution of the wettable powder was tested in the same manner as in the above tests for the compounds of this invention. The test results obtained are shown in Table 3 below. Compound No. shown in the following Table indicates the compound number listed in Tables 1a, 1b and 1c given hereinbefore.

TABLE 3

| Test Compound No. | Application rate of the active ingredient (g/10 ares) | Rate (%) of kill of weeds | Phyto-toxicity |
| --- | --- | --- | --- |
| 1 | 15 | 100 | 0 |
| 4 | 4 | 100 | 0 |
| 8 | 4 | 100 | 0 |
| 25 | 4 | 100 | 0 |
| 26 | 4 | 100 | 0 |
| 27 | 4 | 100 | 0 |
| 28 | 4 | 100 | 0 |
| 29 | 4 | 100 | 0 |
| 30 | 4 | 100 | 0 |
| 31 | 4 | 100 | 0 |
| 32 | 4 | 100 | 0 |
| 33 | 4 | 100 | 0 |
| 34 | 4 | 100 | 0 |
| 35 | 1 | 100 | 0 |
| 38 | 1 | 100 | 0 |
| 42 | 4 | 100 | 0 |
| 65 | 15 | 100 | 0 |
| 66 | 4 | 100 | 0 |
| 72 | 15 | 100 | 0 |
| 73 | 15 | 100 | 0 |
| 74 | 15 | 100 | 0 |
| 75 | 15 | 100 | 0 |
| 76 | 15 | 100 | 0 |
| 85 | 2 | 100 | 0 |
| 88 | 4 | 100 | 0 |
| 135 | 15 | 100 | 0 |
| 165 | 4 | 100 | 0 |
| 166 | 1 | 100 | 0 |
| 169 | 15 | 100 | 0 |
| 170 | 4 | 100 | 0 |
| 181 | 2 | 100 | 0 |
| 184 | 4 | 100 | 0 |
| 200 | 2 | 100 | 0 |
| 221 | 1 | 100 | 0 |
| 222 | 1 | 100 | 0 |
| 231 | 2 | 100 | 0 |
| 234 | 2 | 100 | 0 |
| 269 | 2 | 100 | 0 |
| 270 | 2 | 100 | 0 |
| 281 | 2 | 100 | 0 |
| 284 | 2 | 100 | 0 |
| 318 | 4 | 100 | 0 |
| 320 | 15 | 100 | 0 |
| 322 | 2 | 100 | 0 |
| 324 | 2 | 100 | 0 |
| 331 | 1 | 100 | 0 |
| 334 | 2 | 100 | 0 |

TABLE 3-continued

| Test Compound No. | Application rate of the active ingredient (g/10 ares) | Rate (%) of kill of weeds | Phyto-toxicity |
| --- | --- | --- | --- |
| 381 | 4 | 100 | 0 |
| 384 | 4 | 100 | 0 |
| 431 | 2 | 100 | 0 |
| 434 | 2 | 100 | 0 |
| 481 | 1 | 100 | 0 |
| 484 | 1 | 100 | 0 |
| 518 | 2 | 100 | 0 |
| 520 | 15 | 100 | 0 |
| 521 | 4 | 100 | 0 |
| 522 | 4 | 100 | 0 |
| 531 | 4 | 100 | 0 |
| 534 | 4 | 100 | 0 |
| 576 | 2 | 100 | 0 |
| 577 | 2 | 100 | 0 |
| 581 | 4 | 100 | 0 |
| 582 | 4 | 100 | 0 |
| 586 | 4 | 100 | 0 |
| 587 | 4 | 100 | 0 |
| 591 | 2 | 100 | 0 |
| 592 | 2 | 100 | 0 |
| 596 | 1 | 100 | 0 |
| 597 | 1 | 100 | 0 |
| 631 | 2 | 100 | 0 |
| 632 | 2 | 100 | 0 |
| 633 | 15 | 100 | 9 |
| 634 | 15 | 100 | 0 |
| 635 | 4 | 100 | 0 |
| 636 | 4 | 100 | 0 |
| 637 | 15 | 100 | 0 |
| 638 | 15 | 100 | 0 |
| 639 | 2 | 100 | 0 |
| 640 | 4 | 100 | 0 |
| 650 | 4 | 100 | 0 |
| 656 | 15 | 100 | 0 |
| 658 | 15 | 100 | 0 |
| 662 | 4 | 100 | 0 |
| 665 | 4 | 100 | 0 |
| 666 | 4 | 100 | 0 |
| 675 | 4 | 100 | 0 |
| 678 | 15 | 100 | 0 |
| Comparative Compound A | 100 | 60 | 3 |

Comparative Compound A used in this test Example was a tetrazolinone derivative of the formula

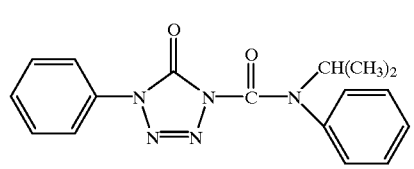

(A)

namely 1-phenyl-4-(N-isopropyl-N-phenylcarbamoyl)-tetrazolin-5-one which is disclosed in Japanese patent application Kokai No. 62-12767. (Comparative Compound A was also used similarly in the following Test Examples 2 to 4 below.)

Test Example 2

Tests of the herbicidal effects on early watergrass (Herbicidal treatments of unwanted weeds during the growing period of weed Each of pots having a top surface area of 1/5000 ares was filled with a soil of the irrigated rice field. The soil in each pot was added with a volume of water and with a complex fertilizer (N:P:K=17:17:17) and then was puddled. In the surface layer of the watered soil were sown uniformly seeds of early watergrass to depth of 1 cm in the surface layer of the soil.

Each pot was then irrigated with water and the depth of the irrigating water on the soil surface was kept at 3 cm. Each pot was subsequently controlled under the condition of glass greenhouse.

A diluted solution of a wettable powder was prepared by diluting with water to a predetermined concentration of the active ingredient such a wettable powder which had been formulated similarly to the procedure of Example 13 above. At the 1.5-leaved stage of the early watergrass growing in each pot, the diluted solution prepared as above was drop-wise added at predetermined rate to the irrigating water in the pot to conduct the herbicidal treatment.

21 Days after the herbicidal treatments, the herbicidal effects on early watergrass were investigated, and the rate (percentages) of kill of the weeds was assessed on the same gradings as that in Test Example 1. A wettable powder containing as a reference chemical comparative compound A was prepared in accordance with the procedure of Example 13 above. For a comparative test, the resultant diluted solution of said wettable powder was tested in the same manner as in the above tests for the compounds of this invention. The test results obtained are shown in Table 4 below. Compound No. shown in the following Table indicates the compound number listed in Tables 1a, 1b and 1c hereinbefore.

TABLE 4

| Test Compound No. | Application rate of the active ingredient (g/10 ares) | Rate (%) of kill of weeds |
| --- | --- | --- |
| 1 | 30 | 100 |
| 4 | 8 | 100 |
| 8 | 8 | 100 |
| 25 | 8 | 100 |
| 26 | 8 | 100 |
| 27 | 8 | 100 |
| 28 | 8 | 100 |
| 29 | 8 | 100 |
| 30 | 8 | 100 |
| 31 | 8 | 100 |
| 32 | 8 | 100 |
| 33 | 8 | 100 |
| 34 | 8 | 100 |
| 35 | 2 | 100 |
| 38 | 2 | 100 |
| 42 | 8 | 100 |
| 65 | 30 | 100 |
| 66 | 8 | 100 |
| 72 | 30 | 100 |
| 73 | 30 | 100 |
| 74 | 30 | 100 |
| 75 | 30 | 100 |
| 76 | 30 | 100 |
| 85 | 4 | 100 |
| 88 | 4 | 100 |
| 135 | 30 | 100 |
| 165 | 8 | 100 |
| 166 | 2 | 100 |
| 169 | 30 | 100 |
| 170 | 8 | 100 |
| 181 | 4 | 100 |
| 184 | 4 | 100 |
| 200 | 4 | 100 |
| 221 | 2 | 100 |
| 222 | 2 | 100 |
| 231 | 4 | 100 |
| 234 | 4 | 100 |
| 269 | 4 | 100 |
| 270 | 4 | 100 |
| 281 | 4 | 100 |
| 284 | 4 | 100 |
| 318 | 8 | 100 |
| 320 | 30 | 100 |
| 322 | 4 | 100 |
| 324 | 4 | 100 |
| 331 | 2 | 100 |
| 334 | 2 | 100 |
| 381 | 8 | 100 |
| 384 | 8 | 100 |
| 431 | 4 | 100 |
| 434 | 4 | 100 |
| 481 | 2 | 100 |
| 484 | 2 | 100 |
| 518 | 2 | 100 |
| 520 | 30 | 100 |
| 521 | 15 | 100 |
| 522 | 8 | 100 |
| 531 | 4 | 100 |
| 534 | 8 | 100 |
| 576 | 4 | 100 |
| 577 | 8 | 100 |
| 581 | 15 | 100 |
| 582 | 8 | 100 |
| 586 | 8 | 100 |
| 587 | 15 | 100 |
| 591 | 8 | 100 |
| 592 | 8 | 100 |
| 596 | 4 | 100 |
| 597 | 4 | 100 |
| 631 | 8 | 100 |
| 632 | 8 | 100 |
| 633 | 30 | 100 |
| 634 | 30 | 100 |
| 635 | 15 | 100 |
| 636 | 15 | 100 |
| 637 | 30 | 100 |
| 638 | 30 | 100 |
| 639 | 8 | 100 |
| 640 | 30 | 100 |
| 650 | 30 | 100 |
| 656 | 30 | 100 |
| 658 | 30 | 100 |
| 662 | 30 | 100 |
| 665 | 15 | 100 |
| 666 | 15 | 100 |
| 675 | 15 | 100 |
| 678 | 30 | 100 |
| Comparative Compound A | 100 | 50 |

Test Example 3

Tests of the herbicidal effects on weeds (common false pimpernel, Monochoria, Japanese bulrush) predominant in irrigated field of aquatic rice plant Each of pots having a top surface area of 1/5000 ares was filled with a soil of the rice field. The soil in each pot was added with a volume of water and with a complex fertilizer (N:P:K=17:17:17) and then puddled. 30 Seeds of weeds, that is, common false-pimpernel, Monochoria and Japanese bulrush were sown in separate pots, respectively, to a depth of 2 cm in the soil of these pots. Immediately after the sowing of seeds, each pot was irrigated with water and the depth of the irrigating water on the soil surface was kept at 2 cm. Each pot was subsequently managed in the green house. A wettable powder as formulated similarly to the procedure of Example 13 above was diluted with water to a predetermined concentration of the active ingredient, and the resultant diluted preparation of the herbicidal compound so prepared was dropwise added at a predetermimed rate to the pots at one day after the weed seed sowing.

21 Days after the herbicidal treatments made by the above application of the herbicidal compound, the rate (%) of kill of the weeds was assessed and evaluated in the same manner as in Test Example 1. Further, a wettable powder containing Comparative Compound A as a reference chemical was prepared in accordance with the procedure of Example 13 above and was tested in the same manner as the compound of this invention. The results obtained are shown in Table 5 below. Compound No. shown in the following Table indicates the compound number listed in Tables 1a–1c hereinbefore.

TABLE 5

| Test Compound No. | Application rate of the active ingredient (g/10 ares) | Rate (%) of kill of weeds predominant in irrigated field of aquatic rice plant | | |
|---|---|---|---|---|
| | | False pimpernel | Monochoria | Japanese bulrush |
| 1 | 15 | 100 | 95 | 95 |
| 4 | 4 | 100 | 100 | 100 |
| 8 | 4 | 100 | 100 | 100 |
| 25 | 4 | 100 | 100 | 100 |
| 26 | 4 | 100 | 100 | 100 |
| 27 | 4 | 100 | 100 | 100 |
| 28 | 4 | 100 | 100 | 100 |
| 29 | 4 | 100 | 100 | 100 |
| 30 | 4 | 100 | 100 | 100 |
| 31 | 4 | 100 | 100 | 100 |
| 32 | 4 | 100 | 100 | 100 |
| 33 | 4 | 100 | 100 | 100 |
| 34 | 4 | 100 | 100 | 100 |
| 35 | 2 | 100 | 100 | 100 |
| 38 | 2 | 100 | 100 | 100 |
| 42 | 4 | 100 | 100 | 100 |
| 65 | 15 | 100 | 90 | 90 |
| 66 | 4 | 100 | 100 | 100 |
| 72 | 15 | 100 | 90 | 95 |
| 73 | 15 | 100 | 90 | 95 |
| 74 | 15 | 100 | 90 | 95 |
| 75 | 15 | 95 | 100 | 100 |
| 76 | 15 | 90 | 90 | 100 |
| 85 | 2 | 100 | 100 | 100 |
| 88 | 4 | 100 | 100 | 100 |
| 135 | 15 | 90 | 90 | 90 |
| 165 | 4 | 100 | 90 | 90 |
| 166 | 2 | 100 | 100 | 100 |
| 169 | 15 | 90 | 90 | 100 |
| 170 | 4 | 100 | 100 | 90 |
| 181 | 2 | 100 | 100 | 100 |
| 184 | 4 | 100 | 100 | 100 |
| 200 | 2 | 100 | 100 | 100 |
| 221 | 2 | 100 | 95 | 100 |
| 222 | 2 | 100 | 100 | 100 |
| 231 | 2 | 100 | 100 | 100 |
| 234 | 2 | 100 | 100 | 100 |
| 269 | 4 | 100 | 100 | 100 |
| 270 | 4 | 100 | 100 | 100 |
| 281 | 2 | 100 | 100 | 100 |
| 284 | 2 | 100 | 100 | 100 |
| 318 | 4 | 95 | 90 | 100 |
| 320 | 15 | 100 | 90 | 95 |
| 322 | 2 | 100 | 100 | 100 |
| 324 | 2 | 100 | 100 | 100 |
| 331 | 2 | 100 | 100 | 100 |
| 334 | 2 | 100 | 100 | 100 |
| 381 | 4 | 100 | 100 | 100 |
| 384 | 4 | 100 | 100 | 100 |
| 431 | 4 | 100 | 100 | 100 |
| 434 | 4 | 100 | 100 | 100 |
| 481 | 2 | 100 | 100 | 100 |
| 484 | 2 | 100 | 100 | 100 |
| 518 | 4 | 100 | 100 | 100 |
| 520 | 15 | 90 | 95 | 90 |

TABLE 5-continued

| Test Compound No. | Application rate of the active ingredient (g/10 ares) | Rate (%) of kill of weeds predominant in irrigated field of aquatic rice plant | | |
|---|---|---|---|---|
| | | False pimpernel | Monochoria | Japanese bulrush |
| 521 | 4 | 100 | 95 | 100 |
| 522 | 4 | 100 | 100 | 95 |
| 531 | 4 | 100 | 100 | 100 |
| 534 | 4 | 100 | 100 | 100 |
| 576 | 4 | 100 | 100 | 100 |
| 577 | 4 | 100 | 100 | 100 |
| 581 | 4 | 100 | 100 | 100 |
| 582 | 4 | 100 | 95 | 100 |
| 586 | 4 | 100 | 100 | 100 |
| 587 | 4 | 95 | 100 | 95 |
| 591 | 4 | 100 | 100 | 100 |
| 592 | 4 | 100 | 100 | 100 |
| 596 | 2 | 100 | 100 | 100 |
| 597 | 2 | 100 | 100 | 100 |
| 631 | 4 | 100 | 100 | 100 |
| 632 | 4 | 95 | 100 | 90 |
| 633 | 15 | 95 | 95 | 90 |
| 634 | 15 | 95 | 95 | 95 |
| 635 | 4 | 100 | 90 | 90 |
| 636 | 4 | 100 | 95 | 90 |
| 637 | 15 | 90 | 90 | 90 |
| 638 | 15 | 90 | 90 | 90 |
| 639 | 4 | 100 | 100 | 100 |
| 640 | 4 | 100 | 100 | 100 |
| 650 | 4 | 100 | 100 | 100 |
| 656 | 15 | 95 | 95 | 95 |
| 658 | 15 | 95 | 100 | 95 |
| 662 | 4 | 100 | 100 | 100 |
| 665 | 4 | 100 | 100 | 100 |
| 666 | 4 | 100 | 100 | 100 |
| 675 | 4 | 100 | 100 | 100 |
| 678 | 15 | 95 | 95 | 100 |
| Comparative CompoundA | 100 | 70 | 70 | 40 |

Test Example 4

Test of herbicidal effects on weeds predominant in farm-field (non-irrigated) and tests of phyto-toxicity to crop plants 1) Tests of herbicidal effects on weeds in farm-field Each of biscuit pots having a top surface area of 1/5000 ares was filled with a farm-field soil (Alluvium loam). In the soil top layer of up to the 1 cm depth in each pot, the soil was evenly mixed with 50 seeds of each sort of weeds chosen from southern crabgrass, green foxtail, vervet leaf, livid amaranth and tufted knotweed. The soil top surface containing the sown seeds was pressed lightly in each pot. An emulsifiable concentrate as formulated similarly to the procedure of Example 14 above was diluted with water to prepare a diluted emulsion preparation of the herbicidal compound. 2 Days after the seed sowing, the diluted emulsion preparation was applied by spraying to the soil surface in each pot at such a rate that the amount of the emulsion preparation applied was 100 liters per 10 ares. This was equivalent to that the amount of the active ingredient applied was at a rate of 50 g of the active ingredient per 10 ares.

30 Days after the treatments with the emulsion preparation, the herbicidal effects were evaluated in terms of the rate (%) of kill of weeds which was calculated according to the same gradings as shown in Test Example 1 above.

2) Tests of phyto-toxicity to crop plants

Each of biscuit pots having a top surface area of 1/10,000 ares was filled with a farm-field soil (Alluvium loam), and in the soil of these separete pots were sown seeds of various crop plants (namely, 5 seeds of soybean, 5 seeds of maize, 10 seeds of sugar beet, 10 seeds of rape, 5 seeds of cotton, 10 seeds of wheat and 10 seeds of barley). The soil surface layer containing the sown seeds was pressed lightly in each pot. An emulsifiable concentrate as formulated similarly to Example 14 above was diluted with water to prepare a diluted emulsion preparation. One day after the seed sowing, the diluted emulsion preparation was applied by spraying to the soil surface in each pot at such a rate that the amount of the emulsion preparation applied was 100 liters per 10 ares. This was equivalent to that the amount of the active ingredient applied was at a rate of 50 g per 10 ares.

30 Days after the treatments with the emulsion preparation, the degree of phyto-toxicity to various crop plants was assessed according to the gradings of evaluation same as those given in Test Example 1 above.

The results obtained are shown in Table 6 below. Compound No. shown in the following Table indicates the compound number listed in Tables 1a–1c hereinbefore.

In both the tests (1) of the herbicidal effects and the tests (2) of the phyto-toxicity, a comparative emulsifiable concentrate containing said Comparative Compound A as a reference chemical was prepared in accordance with the procedure of Example 14 above and was tested in the same manner as the compound of this invention.

TABLE 6

| Test Compound No. | Rate (%) of kill of weeds in farm-field | | | | | Phyto-toxicity to crop plants | | | | | | |
|---|---|---|---|---|---|---|---|---|---|---|---|---|
| | Southern crabgrass | Green foxtail | Vervet leaf | Livid amaranth | Tufted knotweed | Soy bean | Maize | sugar beet | Rape | Wheat | Barley | Cotton |
| 1 | 90 | 100 | 90 | 90 | 90 | 0 | 0 | 0 | 0 | 0 | 0 | 0 |
| 4 | 100 | 100 | 90 | 90 | 95 | 1 | 1 | 0 | 0 | 0 | 0 | 0 |
| 8 | 100 | 100 | 90 | 90 | 90 | 0 | 1 | 0 | 0 | 0 | 0 | 0 |
| 25 | 100 | 100 | 90 | 90 | 90 | 0 | 1 | 1 | 0 | 0 | 0 | 0 |
| 26 | 100 | 100 | 90 | 90 | 90 | 1 | 0 | 0 | 0 | 0 | 0 | 0 |
| 27 | 100 | 100 | 90 | 90 | 90 | 0 | 0 | 0 | 0 | 0 | 0 | 0 |
| 28 | 100 | 100 | 90 | 90 | 90 | 0 | 0 | 0 | 0 | 0 | 0 | 0 |
| 29 | 100 | 100 | 90 | 90 | 90 | 0 | 0 | 1 | 0 | 0 | 0 | 0 |
| 30 | 100 | 100 | 95 | 95 | 90 | 0 | 1 | 0 | 0 | 0 | 0 | 0 |
| 31 | 100 | 100 | 95 | 90 | 90 | 0 | 1 | 1 | 0 | 0 | 1 | 0 |
| 32 | 100 | 100 | 90 | 90 | 90 | 0 | 1 | 1 | 0 | 0 | 0 | 1 |
| 33 | 100 | 100 | 95 | 90 | 90 | 0 | 1 | 0 | 0 | 0 | 0 | 0 |
| 34 | 100 | 100 | 95 | 90 | 90 | 0 | 1 | 1 | 0 | 0 | 0 | 0 |
| 35 | 100 | 100 | 100 | 95 | 90 | 0 | 0 | 0 | 0 | 0 | 0 | 0 |
| 38 | 100 | 100 | 100 | 100 | 95 | 0 | 0 | 1 | 0 | 0 | 0 | 0 |
| 42 | 100 | 100 | 95 | 90 | 90 | 0 | 0 | 0 | 0 | 0 | 0 | 1 |
| 65 | 95 | 100 | 90 | 90 | 90 | 0 | 1 | 1 | 0 | 0 | 0 | 0 |
| 66 | 100 | 100 | 90 | 90 | 90 | 0 | 1 | 0 | 1 | 0 | 0 | 0 |
| 72 | 90 | 95 | 90 | 90 | 90 | 1 | 0 | 1 | 0 | 0 | 0 | 0 |
| 73 | 95 | 100 | 90 | 90 | 90 | 1 | 0 | 0 | 0 | 1 | 0 | 0 |
| 74 | 95 | 100 | 90 | 90 | 90 | 0 | 0 | 1 | 0 | 0 | 0 | 0 |
| 75 | 95 | 100 | 90 | 90 | 95 | 0 | 0 | 1 | 0 | 0 | 0 | 0 |
| 76 | 95 | 95 | 100 | 100 | 95 | 0 | 0 | 0 | 1 | 0 | 1 | 0 |
| 85 | 100 | 100 | 95 | 90 | 90 | 0 | 0 | 0 | 0 | 0 | 0 | 0 |
| 88 | 100 | 100 | 95 | 90 | 90 | 0 | 0 | 1 | 0 | 0 | 0 | 0 |
| 135 | 95 | 95 | 95 | 100 | 90 | 0 | 0 | 0 | 0 | 1 | 0 | 0 |
| 165 | 100 | 100 | 100 | 95 | 90 | 0 | 1 | 0 | 0 | 1 | 0 | 0 |
| 166 | 100 | 100 | 90 | 90 | 95 | 0 | 1 | 0 | 0 | 1 | 1 | 0 |
| 169 | 100 | 100 | 90 | 95 | 95 | 0 | 1 | 0 | 0 | 0 | 0 | 0 |
| 170 | 100 | 100 | 90 | 95 | 95 | 0 | 0 | 0 | 0 | 1 | 1 | 0 |
| 181 | 100 | 100 | 95 | 90 | 90 | 0 | 0 | 0 | 0 | 0 | 0 | 0 |
| 184 | 100 | 100 | 100 | 90 | 90 | 0 | 1 | 0 | 0 | 0 | 0 | 0 |
| 200 | 100 | 100 | 100 | 95 | 90 | 0 | 1 | 0 | 1 | 0 | 1 | 0 |
| 221 | 100 | 100 | 100 | 90 | 90 | 0 | 1 | 1 | 0 | 1 | 1 | 0 |
| 222 | 100 | 100 | 100 | 95 | 95 | 0 | 1 | 0 | 0 | 1 | 1 | 0 |
| 231 | 100 | 100 | 95 | 90 | 90 | 1 | 0 | 0 | 0 | 1 | 0 | 0 |
| 234 | 100 | 100 | 100 | 90 | 90 | 0 | 0 | 0 | 0 | 0 | 0 | 0 |
| 269 | 100 | 100 | 95 | 95 | 95 | 0 | 0 | 1 | 0 | 1 | 1 | 0 |
| 270 | 100 | 100 | 95 | 90 | 90 | 0 | 0 | 1 | 0 | 0 | 1 | 1 |
| 281 | 100 | 100 | 100 | 90 | 90 | 0 | 1 | 0 | 0 | 0 | 0 | 0 |
| 284 | 100 | 100 | 95 | 90 | 90 | 0 | 0 | 0 | 0 | 0 | 0 | 0 |
| 318 | 100 | 100 | 90 | 90 | 90 | 0 | 1 | 0 | 1 | 0 | 0 | 0 |
| 320 | 90 | 90 | 90 | 90 | 90 | 0 | 1 | 0 | 0 | 1 | 1 | 0 |
| 322 | 100 | 100 | 100 | 90 | 90 | 1 | 1 | 0 | 0 | 1 | 0 | 0 |
| 324 | 100 | 100 | 90 | 90 | 95 | 1 | 1 | 0 | 0 | 1 | 0 | 0 |
| 331 | 100 | 100 | 95 | 90 | 90 | 0 | 0 | 1 | 0 | 0 | 0 | 0 |
| 334 | 100 | 100 | 95 | 90 | 90 | 0 | 1 | 0 | 1 | 0 | 0 | 0 |
| 381 | 100 | 100 | 95 | 90 | 90 | 0 | 0 | 0 | 0 | 0 | 0 | 0 |
| 384 | 100 | 100 | 95 | 90 | 90 | 0 | 1 | 0 | 1 | 0 | 0 | 0 |
| 431 | 100 | 100 | 90 | 90 | 90 | 0 | 0 | 1 | 0 | 0 | 0 | 0 |
| 434 | 100 | 100 | 95 | 90 | 90 | 0 | 0 | 0 | 0 | 1 | 0 | 0 |
| 481 | 100 | 100 | 95 | 90 | 90 | 0 | 1 | 0 | 1 | 0 | 0 | 0 |
| 484 | 100 | 100 | 100 | 95 | 90 | 1 | 1 | 0 | 0 | 0 | 0 | 0 |
| 518 | 100 | 95 | 95 | 90 | 95 | 0 | 1 | 1 | 0 | 1 | 1 | 0 |
| 520 | 95 | 95 | 90 | 95 | 95 | 1 | 1 | 0 | 0 | 1 | 0 | 1 |
| 521 | 100 | 100 | 100 | 100 | 100 | 0 | 1 | 0 | 1 | 0 | 1 | 0 |

TABLE 6-continued

| Test Compound No. | Rate (%) of kill of weeds in farm-field | | | | | Phyto-toxicity to crop plants | | | | | | |
|---|---|---|---|---|---|---|---|---|---|---|---|---|
| | Southern crabgrass | Green foxtail | Vervet leaf | Livid amaranth | Tufted knotweed | Soy bean | Maize | sugar beet | Rape | Wheat | Barley | Cotton |
| 522 | 100 | 100 | 95 | 95 | 95 | 0 | 1 | 1 | 0 | 1 | 1 | 0 |
| 531 | 100 | 100 | 90 | 90 | 90 | 0 | 0 | 0 | 0 | 0 | 0 | 0 |
| 534 | 100 | 100 | 90 | 90 | 90 | 0 | 0 | 0 | 0 | 0 | 0 | 0 |
| 576 | 100 | 100 | 95 | 90 | 90 | 0 | 0 | 0 | 1 | 1 | 0 | 0 |
| 577 | 100 | 100 | 95 | 90 | 90 | 0 | 0 | 0 | 1 | 1 | 0 | 0 |
| 581 | 100 | 100 | 90 | 90 | 90 | 0 | 0 | 0 | 1 | 0 | 1 | 1 |
| 582 | 100 | 100 | 90 | 90 | 95 | 0 | 1 | 1 | 0 | 1 | 0 | 0 |
| 586 | 100 | 100 | 90 | 90 | 100 | 0 | 1 | 1 | 0 | 1 | 0 | 0 |
| 587 | 100 | 100 | 95 | 95 | 100 | 1 | 0 | 0 | 0 | 1 | 0 | 0 |
| 591 | 100 | 100 | 100 | 95 | 100 | 0 | 1 | 0 | 0 | 0 | 1 | 0 |
| 592 | 100 | 100 | 95 | 100 | 100 | 0 | 1 | 0 | 0 | 0 | 0 | 0 |
| 596 | 100 | 100 | 90 | 100 | 100 | 1 | 0 | 0 | 0 | 0 | 0 | 0 |
| 597 | 100 | 100 | 95 | 90 | 90 | 0 | 1 | 0 | 0 | 0 | 1 | 0 |
| 631 | 100 | 100 | 90 | 90 | 90 | 0 | 1 | 0 | 0 | 0 | 1 | 0 |
| 632 | 100 | 100 | 90 | 95 | 90 | 0 | 0 | 0 | 0 | 1 | 1 | 0 |
| 633 | 100 | 90 | 90 | 90 | 100 | 1 | 0 | 0 | 0 | 1 | 1 | 1 |
| 634 | 100 | 100 | 90 | 90 | 95 | 0 | 1 | 1 | 0 | 0 | 0 | 0 |
| 635 | 100 | 100 | 95 | 95 | 100 | 1 | 0 | 0 | 0 | 0 | 1 | 0 |
| 636 | 100 | 100 | 95 | 95 | 95 | 0 | 0 | 0 | 1 | 1 | 0 | 0 |
| 637 | 100 | 90 | 90 | 90 | 90 | 0 | 1 | 0 | 0 | 1 | 0 | 0 |
| 638 | 100 | 95 | 90 | 90 | 90 | 0 | 1 | 1 | 0 | 1 | 0 | 0 |
| 639 | 100 | 100 | 95 | 95 | 100 | 0 | 0 | 1 | 1 | 0 | 0 | 0 |
| 640 | 100 | 100 | 95 | 95 | 100 | 0 | 0 | 1 | 1 | 0 | 0 | 0 |
| 650 | 100 | 100 | 90 | 90 | 95 | 0 | 0 | 0 | 1 | 0 | 0 | 0 |
| 656 | 100 | 90 | 90 | 90 | 95 | 0 | 1 | 1 | 0 | 1 | 0 | 0 |
| 658 | 100 | 95 | 90 | 90 | 90 | 0 | 1 | 1 | 0 | 1 | 0 | 0 |
| 662 | 100 | 100 | 90 | 95 | 95 | 0 | 0 | 1 | 0 | 0 | 0 | 0 |
| 665 | 100 | 100 | 90 | 95 | 95 | 1 | 0 | 1 | 0 | 1 | 0 | 0 |
| 666 | 100 | 100 | 90 | 90 | 100 | 0 | 1 | 1 | 0 | 1 | 0 | 0 |
| 675 | 100 | 100 | 95 | 95 | 100 | 0 | 0 | 0 | 1 | 1 | 1 | 0 |
| 678 | 100 | 95 | 90 | 95 | 100 | 0 | 0 | 0 | 0 | 1 | 0 | 0 |
| Comparative Compound A | 70 | 70 | 70 | 60 | 40 | 3 | 2 | 3 | 3 | 0 | 0 | 0 |

Industrial Availability

As described in the above, the new, herbicidal 1-substituted-4-carbamoyl-1,2,4-triazol-5-one derivatives according to this invention have an excellent herbicidal activity and can achieve a complete kill of various sorts of weeds in both the irrigated field of aqatic rice plant and the farm-fields even at a lower application rate of the compound, and also they have excellent selectivity between useful crop plants and unwanted weeds. Accordingly, the new compound of this invention is very useful as a selective herbicide.

What is claimed is:

1. A 1-substituted-4-carbamoyl-1,2,4-triazol-5-one derivative represented by the general formula (I)

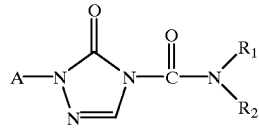

(I)

wherein:

(i) A is an unsubstituted or substituted phenyl group represented by the formula

in which X may be the same or different and is a halogen atom, a lower alkyl group, a lower haloalkyl group, a lower alkoxy group, a lower haloalkoxy group, cyano group, nitro group, methylthio group, methylsulfinyl group, methylsulfonyl group, phenoxy group, acetylamino group or trifluoroacetylamino group, and n is 0 or an integer of 1 to 5, or (ii) A is 1-naphthyl group of the formula

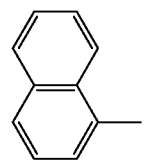

or 5,6,7,8-tetrahydro-1-naphthyl group of the formula

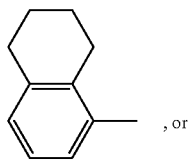

, or (iii) A is an unsubstituted or substituted benzyl group or phenethyl group represented by the formula

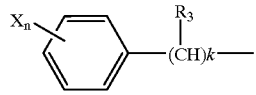

in which X and n have the same meanings as defined above, $R_3$ is hydrogen atom or methyl group and k denotes an integer of 1 to 2;
$R_1$ is a lower alkyl group, a lower alkenyl group, a lower alkynyl group or a lower cycloalkyl group; and
$R_2$ is a lower alkyl group, a lower cycloalkyl group or an unsubstituted or substituted phenyl group having the formula

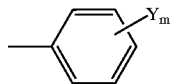

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with a halogen atom; or $R_2$ is an unsubstituted or substituted pyridyl group having the formula

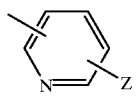

in which Z is hydrogen atom or chlorine atom.

2. A derivative as claimed in claim 1, wherein the derivative of the general formula (I) is a 1-phenyl-4-(N,N-di-substituted carbamoyl)-1,2,4-triazol-5-one derivative represented by the general formula (Ia)

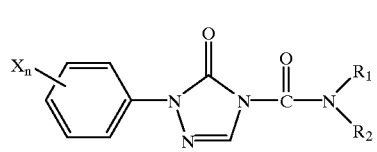

(Ia)

wherein:
X has the same meaning as defined in claim 1, wherein X may be the same or different and is a halogen atom, a lower alkyl group, a lower haloalkyl group, a lower alkoxy group, a lower haloalkoxy group, cyano group, nitro group, methylthio group, methylsulfinyl group, methylsulfonyl group, phenoxy group, acetylamino group or trifluoroacetylamino group;

n is 0 or an integer of 1 to 5; and
$R_1$ and $R_2$ have the same meanings as defined in claim 1, wherein $R_1$ is a lower alkyl group, a lower alkenyl group, a lower alkynyl group or a lower cycloalkyl group, and $R_2$ is a lower alkyl group, a lower cycloalkyl group or an unsubstituted or substituted phenyl group having the formula

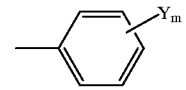

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with a halogen atom; or $R_2$ is an unsubstituted or substituted pyridyl group having the formula

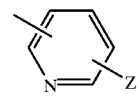

in which Z is hydrogen atom or chlorine atom.

3. A derivative as claimed in claim 2, wherein the derivative of the general formula (Ia) is a 1-phenyl-4-(N,N-di-substituted carbamoyl)-1,2,4-triazol-5-one derivative represented by the general formula (Ia-1)

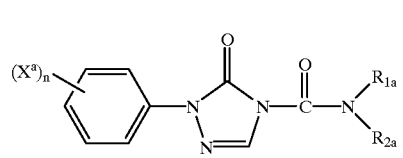

(Ia-1)

where $R_{1a}$ is a lower alkyl group, $R_{2a}$ is a mono-halo- or di-halo-substituted phenyl group, $X^a$ is a halogen atom, a lower alkyl group or a lower haloalkyl group, and n is 0 or an integer of 1 to 2.

4. A derivative as claimed in claim 2, wherein the derivative of the general formula (Ia) is a 1-phenyl-4-(N, N-di-substituted carbamoyl)-1,2,4-triazol-5-one derivative represented by the general formula (Ia-1-1)

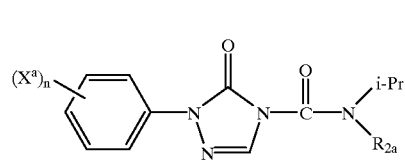

(Ia-1-1)

where i-Pr means isopropyl group, $R_{2a}$ is a mono-halo- or di-halo-substituted phenyl group, $X^a$ is a halogen atom, a lower alkyl group or a lower haloalkyl group, and n is 0 or an integer of 1 to 2.

5. A derivative as claimed in claim 4, wherein the derivative of the general formula (Ia-1-1) is a 1-phenyl-4-(N,N-di-substituted carbamoyl)-1,2,4-triazol-5-one derivative represented by the general formula (Ia-1-2)

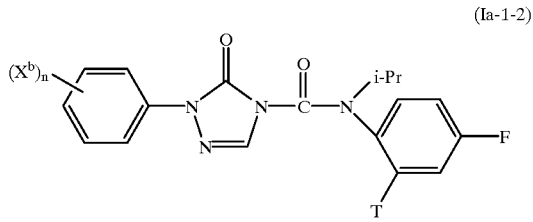

(Ia-1-2)

where i-Pr means isopropyl group, T is hydrogen atom or fluorine atom, $X^b$ may be the same or different and is chlorine atom.

6. A derivative as claimed in claim 5, wherein the derivative of the general formula (Ia-1-2) is:

1-phenyl-4-(N-isopropyl-N-4-fluorophenyl-carbamoyl)-1,2,4-triazol-5-one, 1-phenyl-4-(N-isopropyl-N-2,4-difluorophenyl-carbamoyl)-1,2,4-triazol-5-one, 1-(2-chlorophenyl)-4-(N-isopropyl-N-4-fluorophenyl-carbamoyl)-1,2,4-triazol-5-one, 1-(2-chlorophenyl)-4-(N-isopropyl-N-2,4-difluorophenyl-carbamoyl)-1,2,4-triazol-5-one, 1-(3-chlorophenyl)-4-(N-isopropyl-N-4-fluorophenyl-carbamoyl)-1,2,4-triazol-5-one, 1-(3-chlorophenyl)-4-(N-isopropyl-N-2,4-difluorophenyl-carbamoyl)-1,2,4-triazol-5-one, 1-(2-fluorophenyl)-4-(N-isopropyl-N-4-fluorophenyl-carbamoyl)-1,2,4-triazol-5-one, 1-(2-fluorophenyl)-4-(N-isopropyl-N-2,4-difluorophenyl-carbamoyl)-1,2,4-triazol-5-one, 1-(2,4-difluorophenyl)-4-(N-isopropyl-N-4-fluorophenyl-carbamoyl)-1,2,4-triazol-5-one, 1-(2,4-difluorophenyl)-4-(N-isopropyl-N-2,4-difluorophenyl-carbamoyl)-1,2,4-triazol-5-one, 1-(2-fluoro-4-chlorophenyl)-4-(N-isopropyl-N-4-fluorophenyl-carbamoyl)-1,2,4-triazol-5-one, 1-(2-fluoro-4-chlorophenyl)-4-(N-isopropyl-N-2,4-difluorophenyl-carbamoy)-1,2,4-triazol-5-one, 1-(2-methylphenyl)-4-(N-isopropyl-N-4-fluorophenyl-carbamoyl)-1,2,4-triazol-5-one, 1-(2-methylphenyl)-4-(N-isopropyl-N-2,4-difluorophenyl-carbamoyl)-1,2,4-triazol-5-one, 1-(2,3-dimethylphenyl)-4-(N-isopropyl-N-4-fluorophenyl-carbamoyl)-1,2,4-triazol-5-one, 1-(2,3-dimethylphenyl)-4-(N-isopropyl-N-2,4-difluorophenyl-carbamoyl)-1,2,4-triazol-5-one, 1-(2-chloro-4-methylphenyl)-4-(N-isopropyl-N-4-fluorophenyl-carbamoyl)-1,2,4-triazol-5-one, 1-(2-chloro-4-methylphenyl)-4-(N-isopropyl-N-2,4-difluorophenyl-carbamoyl)-1,2,4-triazol-5-one.

7. A derivative as claimed in claim 2, wherein the derivative of the general formula (Ia) is a 1-phenyl-4-(N,N-di-substituted carbamoyl)-1,2,4-triazol-5-one derivative represented by the general formula (Ia-2)

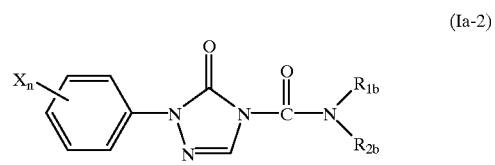

(Ia-2)

where X and n have the same meanings as defined in claim 2, $R_{1b}$ is a lower alkyl group, and $R_{2b}$ is a lower cycloalkyl group.

8. A derivative as claimed in claim 7, which is a 1-phenyl-4-(N,N-di-substituted carbamoyl)-1,2,4-triazol-5-one derivative of the general formula (Ia-2) where X is chlorine atom, fluorine atom, methyl group, ethyl group, trifluoromethyl group or trifluoromethyloxy group, n is 0 or an integer of 1 to 2, $R_{1b}$ is methyl group, ethyl group, n-propyl group or isopropyl group, and $R_{2b}$ is cyclopropyl group, cyclopentyl group or cyclohexyl group.

9. A derivative as claimed in claim 1, wherein the derivative of the general formula (I) is a 1-naphthyl-4-(N,N-di-substituted carbamoyl)-1,2,4-triazol-5-one derivative represented by the general formula (Ib)

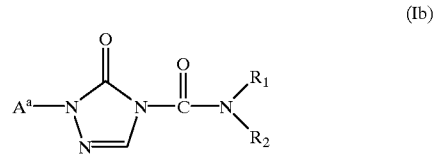

(Ib)

in which
$A^a$ is 1-naphthyl group of the formula

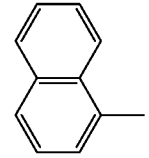

or 5,6,7,8-tetrahydro-1-naphthyl group of the formula

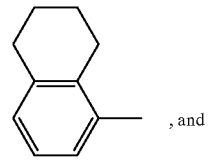

, and $R_1$ and $R_2$ have the same meanings as defined in claim 1, wherein $R_1$ is a lower alkyl group, a lower alkenyl group, a lower alkynyl group or a lower cycloalkyl group, and $R_2$ is a lower alkyl group, a lower cycloalkyl group or an unsubstituted or substituted phenyl group having the formula

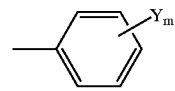

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with a halogen atom; or $R_2$ is an unsubstituted or substituted pyridyl group having the formula

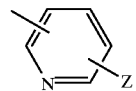

in which Z is hydrogen atom or chlorine atom.

10. A derivative as claimed in claim 9, which is a 1-naphthyl-4-(N,N-di-substituted carbamoyl)-1,2,4-triazol-5-one derivative represented by the general formula (Ib) where $R_1$ is a lower alkyl group and $R_2$ is a mono-halo- or di-halo-substituted phenyl group.

11. A derivative as claimed in claim 1, wherein the derivative of the general formula (I) is a 1-aralkyl-4-(N,N-di-substituted carbamoyl)-1,2,4-triazol-5-one derivative represented by the general formula (Ic)

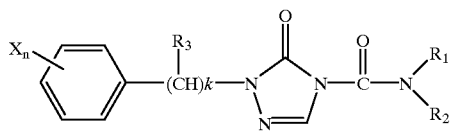

in which:
X has the same meaning as defined in claim 1, wherein X may be the same or different and is a halogen atom, a lower alkyl group, a lower haloalkyl group, a lower alkoxy group, a lower haloalkoxy group, cyano group, nitro group, methylthio group, methylsulfinyl group, methylsulfonyl group, phenoxy group, acetylamino group or trifluoroacetylamino group;
n is 0 or an integer of 1 to 5;
$R_1$ and $R_2$ have the same meanings as defined in claim 1, wherein $R_1$ is a lower alkyl group, a lower alkenyl group, a lower alkynyl group or a lower cycloalkyl group, and $R_2$ is a lower alkyl group, a lower cycloalkyl group or an unsubstituted or substituted phenyl group having the formula

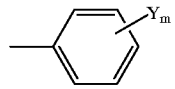

in which m is 0 or an integer of 1 to 5 and Y may be the same or different and is a halogen atom, a lower alkyl group, a lower haloalkyl group, a lower alkoxy group, a lower haloalkoxy group or cyano group; or $R_2$ is a benzyl group of which benzene ring may be substituted with a halogen atom; or $R_2$ is an unsubstituted or substituted pyridyl group having the formula

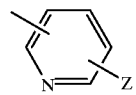

in which Z is hydrogen atom or chlorine atom; $R_3$ is hydrogen atom or methyl group; and k is an integer of 1 or 2.

12. A derivative as claimed in claim 11, wherein the derivative of the general formula (Ic) is a 1-aralkyl-4-(N,N-di-substituted carbamoyl)-1,2,4-triazol-5-one derivative represented by the general formula (Ic-1)

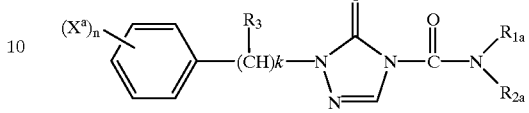

where $R_{1a}$ is a lower alkyl group, $R_{2a}$ is a mono-halo- or di-halo-substituted phenyl group, $X^a$ is a halogen atom, a lower alkyl group or a lower haloalkyl group, n is 0 or an integer of 1 to 2 and k is an integer of 1 or 2.

13. A derivative as claimed in claim 12, wherein the derivative of the general formula (Ic-1) is a 1-aralkyl-4-(N,N-di-substituted carbamoyl)-1,2,4-triazol-5-one derivative represented by the general formula (Ic-1-1)

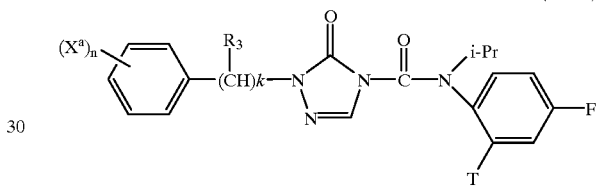

in which i-Pr means isopropyl group, T is hydrogen atom or fluorine atom, $X^b$ may be the same or different and is chlorine atom, bromine atom, fluorine atom, methyl group, ethyl group or trifluoromethyl group, n is 0 or an integer of 1 to 2, $R_3$ is hydrogen atom or methyl group and k is an integer of 1 or 2.

14. A herbicidal composition comprising as an active ingredient a 1-substituted-4-carbamoyl-1,2,4-triazol-5-one derivative represented by the general formula (I)

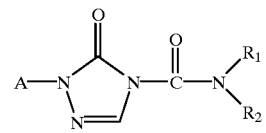

wherein A, $R_1$ and $R_2$ have the same meanings as defined in claim 1.

15. A herbicidal composition as claimed in claim 14, which comprises as an active ingredient a 1-phenyl-4-carbamoyl-1,2,4-triazol-5-one derivative of the general formula (Ia).

16. A herbicidal composition as claimed in claim 14, which comprises as an active ingredient a 1-naphthyl-4-carbamoyl-1,2,4-triazol-5-one derivative of the general formula (Ib).

17. A herbicidal composition as claimed in claim 14, which comprises as an active ingredient a 1-aralkyl-4-carbamoyl-1,2,4-triazol-5-one derivative of the general formula (Ic).

* * * * *